(12) United States Patent
Alenfalk et al.

(10) Patent No.: US 7,871,998 B2
(45) Date of Patent: Jan. 18, 2011

(54) DIPHENYLAZETIDINONE DERIVATIVES POSSESSING CHOLESTEROL ABSORPTION INHIBITORY ACTIVITY

(75) Inventors: Susanne Alenfalk, Mölndal (SE); Mikael Dahlström, Mölndal (SE); Fana Hunegnaw, Mölndal (SE); Staffan Karlsson, Mölndal (SE); Malin Lemurell, Mölndal (SE); Ann-Margret Lindqvist, Mölndal (SE); Tore Skjäret, Mölndal (SE); Ingemar Starke, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 1015 days.

(21) Appl. No.: 10/596,731

(22) PCT Filed: Dec. 21, 2004

(86) PCT No.: PCT/SE2004/001960

§ 371 (c)(1),
(2), (4) Date: Nov. 16, 2006

(87) PCT Pub. No.: WO2005/061452

PCT Pub. Date: Jul. 7, 2005

(65) Prior Publication Data

US 2008/0064676 A1  Mar. 13, 2008
US 2010/0099657 A2  Apr. 22, 2010

(30) Foreign Application Priority Data

Dec. 23, 2003 (GB) .................................. 0329780.1
Jul. 21, 2004 (SE) .................................... 0401907
Nov. 15, 2004 (SE) .................................... 0402785

(51) Int. Cl.
C07D 205/08 (2006.01)
A61K 31/397 (2006.01)
A61P 31/10 (2006.01)
A61P 25/28 (2006.01)
A61P 3/10 (2006.01)

(52) U.S. Cl. .............................. 514/210.02; 540/360
(58) Field of Classification Search ................. 540/360; 514/210.02
See application file for complete search history.

(56) References Cited

U.S. PATENT DOCUMENTS

| | | | |
|---|---|---|---|
| 5,306,817 A | 4/1994 | Thiruvengadam et al. | |
| 5,631,365 A | 5/1997 | Rosenblum et al. | |
| 5,633,246 A | 5/1997 | McKittrick et al. | |
| 5,661,145 A | 8/1997 | Davis | |
| 5,739,321 A | 4/1998 | Wu et al. | |
| 5,744,467 A | 4/1998 | McKittrick et al. | |
| 5,756,470 A | 5/1998 | Yumibe et al. | |
| 5,767,115 A | 6/1998 | Rosenblum et al. | |
| 5,846,966 A | 12/1998 | Rosenblum et al. | |
| 5,886,171 A | 3/1999 | Wu et al. | |
| 5,919,672 A | 7/1999 | Homann et al. | |
| RE37,721 E | 5/2002 | Rosenblum et al. | |
| 7,235,543 B2 | 6/2007 | Burnett et al. | |
| 7,368,562 B2 | 5/2008 | Burnett et al. | |
| 7,470,678 B2 * | 12/2008 | Starke et al. ........... | 514/210.09 |
| 2002/0137690 A1 | 9/2002 | Ghosai et al. | |
| 2003/0119428 A1 | 6/2003 | Davis et al. | |
| 2003/0119757 A1 | 6/2003 | Davis | |
| 2004/0018060 A1 | 1/2004 | Knezek et al. | |
| 2004/0018061 A1 | 1/2004 | Jansson | |
| 2004/0254369 A1 | 12/2004 | Framroze | |
| 2005/0096307 A1 | 5/2005 | Graziano | |
| 2005/0267049 A1 | 12/2005 | Goulet et al. | |
| 2006/0046996 A1 | 3/2006 | Aoki et al. | |
| 2006/0069080 A1 | 3/2006 | Veltri | |
| 2007/0049748 A1 | 3/2007 | Uppala et al. | |

(Continued)

FOREIGN PATENT DOCUMENTS

EP  524595  1/1993
EP  1413331  9/2001

(Continued)

OTHER PUBLICATIONS

McKittrick et al., "Synthesis of C3 heteroatom-substituted azetidinones that display potent cholesterol absorption inhibitory activity," (1998) 41(5):752-759.

(Continued)

*Primary Examiner*—Mark L Berch
(74) *Attorney, Agent, or Firm*—Pepper Hamilton LLP

(57) ABSTRACT

Compounds of formula (I): (wherein variable groups are as defined within) pharmaceutically acceptable salts, solvates, solvates of such salts and prodrugs thereof and their use as cholesterol absorption inhibitors for the treatment of hyperlipidaemia are described. Processes for their manufacture and pharmaceutical compositions containing them are also described.

15 Claims, No Drawings

U.S. PATENT DOCUMENTS

| | | | |
|---|---|---|---|
| 2007/0078098 A1 | 4/2007 | DeVita et al. | |
| 2007/0129540 A1 | 6/2007 | Framroze | |
| 2007/0142304 A1 | 6/2007 | Alenfalk et al. | |
| 2007/0155674 A1 | 7/2007 | Burnett et al. | |
| 2007/0155675 A1 | 7/2007 | Burnett et al. | |
| 2008/0064676 A1 | 3/2008 | Alenfalk et al. | |
| 2008/0070890 A1* | 3/2008 | Burnett et al. | 514/210.05 |
| 2009/0069285 A1* | 3/2009 | Lemurell et al. | 514/210.02 |
| 2010/0048529 A1* | 2/2010 | Dahlstrom et al. | 514/210.02 |
| 2010/0048530 A1* | 2/2010 | Dahlstrom et al. | 514/210.15 |
| 2010/0125059 A1* | 5/2010 | Nakano et al. | 514/210.02 |

FOREIGN PATENT DOCUMENTS

| | | |
|---|---|---|
| EP | 0792264 | 2/2002 |
| EP | 1362855 | 11/2003 |
| WO | 9302048 | 2/1993 |
| WO | 9414433 | 7/1994 |
| WO | 9417038 | 8/1994 |
| WO | 9501961 | 1/1995 |
| WO | 9508532 | 3/1995 |
| WO | 9526334 | 10/1995 |
| WO | 9535277 | 12/1995 |
| WO | 9609827 | 4/1996 |
| WO | 9616037 | 5/1996 |
| WO | 9619450 | 6/1996 |
| WO | 9716424 | 5/1997 |
| WO | 9716455 | 5/1997 |
| WO | 9745406 | 12/1997 |
| WO | 0020623 | 4/2000 |
| WO | 0034240 | 6/2000 |
| WO | 0038725 | 7/2000 |
| WO | 0060107 | 10/2000 |
| WO | 0063703 | 10/2000 |
| WO | 0250027 | 6/2002 |
| WO | 0250060 | 6/2002 |
| WO | 0250068 | 6/2002 |
| WO | 0250090 | 6/2002 |
| WO | 02018432 | 7/2002 |
| WO | 02058685 | 8/2002 |
| WO | 02058696 | 8/2002 |
| WO | 02058731 | 8/2002 |
| WO | 02058732 | 8/2002 |
| WO | 02058733 | 8/2002 |
| WO | 02058734 | 8/2002 |
| WO | 02066464 | 8/2002 |
| WO | 02072104 | 9/2002 |
| WO | 02079174 | 10/2002 |
| WO | 02096415 | 12/2002 |
| WO | 03026643 | 4/2003 |
| WO | 03026644 | 4/2003 |
| WO | 03088962 | 10/2003 |
| WO | 2004000803 | 12/2003 |
| WO | 2004000804 | 12/2003 |
| WO | 2004000805 | 12/2003 |
| WO | 2004005247 | 1/2004 |
| WO | 2004010948 | 2/2004 |
| WO | 2004010993 | 2/2004 |
| WO | 2004014947 | 2/2004 |
| WO | 2004043456 | 5/2004 |
| WO | 2004043457 | 5/2004 |
| WO | 2004081002 | 9/2004 |
| WO | 2004099132 | 11/2004 |
| WO | 2004107958 | 12/2004 |
| WO | 2005000353 | 1/2005 |
| WO | 2005021495 | 3/2005 |
| WO | 2005042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005033100 | 7/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |
| WO | 2004005247 | 11/2007 |

OTHER PUBLICATIONS

Notice of allowance dated Jul. 31, 2008 for U.S. Appl. No. 10/519,897.

Office Action dated Feb. 28, 2008 for U.S. Appl. No. 10/519,897.

Notice of allowance dated Aug. 28, 2007 for U.S. Appl. No. 10/519,897.

Office Action dated May 1, 2007 for U.S. Appl. No. 10/519,897.

Vaccaro et al., "Carboxy-substituted 2-azetidinones as cholesterol absorption inhibitors," Bioorganic & Medicinal Chemistry Letters (1998) 8:319-322.

Clader et al., "2-Azetidinone Cholesterol Absorption Inhibitors: Structure-Activity Relationships on the HeterocyclicNucleus," J. Med Chem (1996) 39:3684-3693.

McKittrick et al., Stereoselective synthesis and biological activity of cis azetidinones as cholesterol absorptioninhibitors, Bioorganic & Medicinal Chemistry Letters (1996) 6(16):1947-1950.

Burnett et al., "2-Azetidinones as Inhibitors of Cholesterol Absorption," J. Med Chem (1994) 12:1733-1736.

Castaner et al., "Ezetimibe Hypolipidemic, Cholesterol absorption inhibitor," Drugs of the Future (2000) 25(7):679-685.

Vaccaro et al., "Sugar-substituted 2-azetidinone cholesterol absorption inhibitors: Enhanced potency by modification ofthe sugar," Bioorganic & Medicinal Chemistry Letters (1998) 8:313-318.

Fu et al., "Process for preparing Ezetimibe intermediate by an acid enhanced chemo- and enantioselective CBScatalyzed ketone reduction," Tetrahedron Letters (2003) 44:801-804.

Kirkup et al., "(i)-SCH 57939: synthesis and pharmacological properties of a potent, metabolically stable cholesterolabsorption inhibitor," Bioorganic & Medicinal Chemistry Letters (1996) 6(17):2069-2072.

Rosenblum et al., "Discovery of 1-(4-fluorophenyl)-(3R)[3-(4-fluorophenyl)-(3S)-hydroxypropyl]-(4S)-(4-hydroxyphenyl)-2-azetidinone (SCH 58235): a designed, potent, orally active inhibitor of cholesterol absorption.," J. Med Chem (1998) 41:973-980.

Wu et al., "A Novel One-Step Diastereo- and Enantioselective Formation of trans-Azetidinones and Its Application tothe Total Synthesis of Cholesterol Absorption Inhibitors," J. Org. Chem (1999) 64:3714-3718.

Dugar et al., "Gamma-lactams and related compounds as cholesterol absorption inhibitors: homologs of the beta-lactam cholesterol absorption inhibitor SCH 48461," Bioorganic & Medicinal Letters (1995) 5(24):2947-2952.

Mounsey et al., "Diet may slow progression of diabetic nephropathy," The Journal of Family Practice (2003) 52 (9):672-673.

Sobieszczyk et al., "Acute pulmonary embolism: don't ignore the platelet," Circulation (2002) 106(14):1748-1749.

van Heek et al., "Comparison of the activity and disposition of the novel cholesterol absorption inhibitor, SCH58235, and its glucuronide, SCH60663," Br. J. Pharmacol (2000) 129(8):1748-1754.

Yang et al., "Allelic Variants in Long-QT Disease Genes in Patients With Drug-Associated Torsades de Pointes,"Circulation (2002) 105(16):1943-1948.

Zaks et al., Enzymatic glucuronidation of a novel cholesterol absorption inhibitor, Sch 58235, Appl BiochemBiotechnol. (1998) 73(2-3):205-214.

Clader "The discovery of ezetimibe: a view from outside the receptor," J Med Chem (2004 47(1):1-9.

Altmann et al., "Niemann-pick C1 like 1 protein is critical for intestinal cholesterol absorption," Science(2004) 303:1201-1204.

Notice of copending applications (2pp), 2008.

Journal of the American College of Cardiology (2000) 35(1):252A.

Kvaerno et al., "Synthesis and in vitro evaluation of inhibitors of intestinal cholesterol absorption," J Med Chem (2005) 48(19):6035-6053.

Burnett "Beta-lactam cholesterol absorption inhibitors," Curr Med Chem (2004) 11:1873-1887.

Seedorf et al., "Cholesterol absorption inhibitor ezetimibe blocks uptake of oxidized LDL in human macrophages," Biochem Biophys Research Commun (2004) 320(4):1337-1341.

Kvaerno et al., "An in vitro assay for evaluation of small-molecule inhibitors of cholesterol absorption," (2004) 43 (35):4653-4656.

Clader "Ezetmibe and other azetidinone cholesterol absorption inhibitors," Curr Topics in Med Chem (2005) 5 (3):243-256.

Carcia-Calvo et al., "The target of ezetimibe is Niemann-Pick C1-Like 1 (NPC1L1)," PNAS (2005) 102(23):8132-8137.

Ritter et al., "Heterocyclic ring scaffolds as small-molecule cholesterol absorption inhibitors," Org Biomol Chem (2005) 3:3514-3523.

Albert "Chemical aspects of selective toxicity," Nature (1958) 182(4633):421-423.

McKittrick et al., "Synthesis of C3 heteroatom-substituted azetidinones that display potent cholesterol absorption inhibitory activity," J Med Chem (1998) 41(5):752-759.

Office Action dated Jul. 15, 2009 received in copending U.S. Appl. No. 10/596,725.

Office Action dated Jun. 10, 2010 received in copending U.S. Appl. No. 11/993,033.

Office Action dated Jun. 7, 2010 received in copending U.S. Appl. No. 11/993,463.

Office Action dated Jun. 9, 2010 received in copending U.S. Appl. No. 11/993,466.

* cited by examiner

DIPHENYLAZETIDINONE DERIVATIVES POSSESSING CHOLESTEROL ABSORPTION INHIBITORY ACTIVITY

CROSS-REFERENCE TO RELATED APPLICATIONS

This application is the U.S. National Stage filing of International Application Serial No. PCT/SE2004/001960 filed Dec. 21, 2004, which claims priority to Swedish Application Serial No. 0402785-0 filed Nov. 15, 2004, and to Swedish Application Serial No. 0401907-1 filed Jul. 21, 2004, and to Great Britain Application Serial No. 0329780.1 filed Dec. 23, 2003, each of which is incorporated herein by reference in its entirety.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 113-446).

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear. The original hypothesis has been that cholesterol is crossing the intestine by unspecific diffusion. But more recent studies are suggesting that there are specific transporters involved in the intestinal cholesterol absorption. (See for instance New molecular targets for cholesterol-lowering therapy Izzat, N, N., Deshazer, M. E. and Loose-Mitchell D. S. JPET 293:315-320, 2000.)

A clear association between reduction of total cholesterol and (LDL) cholesterol and decreased instance of coronary artery disease has been established, and several classes of pharmaceutical agents are used to control serum cholesterol. There major options to regulate plasma cholesterol include (i) blocking the synthesis of cholesterol by agents such as HMG-CoA reductase inhibitors, for example statins such as simvastatin and fluvastatin; which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Even with the current diverse range of therapeutic agents, a significant proportion of the hypercholesterolaemic population is unable to reach target cholesterol levels, or drug interactions or drug safety preclude the long term use needed to reach the target levels. Therefore there is still a need to develop additional agents that are more efficacious and are better tolerated.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, WO 04/043457, WO 04/081002, U.S. Pat. Nos. 5,756,470, 5,767,115, US 20040180860, US20040180861 and US RE37721.

The present invention is based on the discovery that certain 2-azetidinone derivatives surprisingly inhibit cholesterol absorption. Such properties are expected to be of value in the treatment of disease states associated with hyperlipidaemic conditions. The compounds of the present invention are not disclosed in any of the above applications and we have surprisingly found that the compounds of the present invention possess beneficial efficacious, metabolic and toxicological profiles that make them particularly suitable for in vivo administration to a warm blooded animal, such as man. In particular certain compounds of the present invention have a low degree of absorption compared to compounds of the prior art whilst retaining their ability to inhibit cholesterol absorption.

Accordingly there is provided a compound of formula (I):

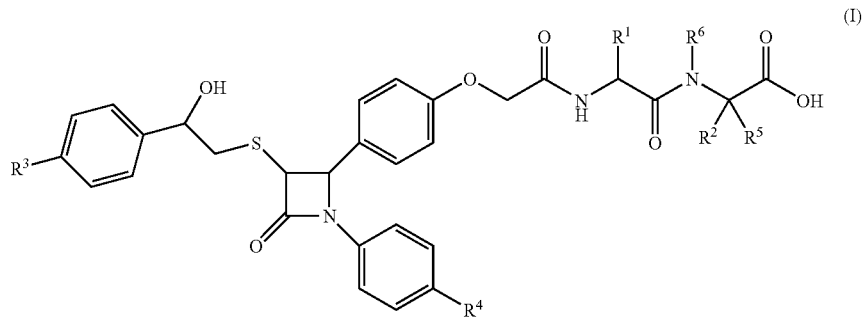

wherein:

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N-($C_{1-6}$alkyl)amino, N,N-($C_{1-6}$alkyl)$_2$-amino, $C_1$-$C_6$ alkyl-carbonylamino $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;

$R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, $(C_1$-$C_4)_3$Si, N -($C_{1-6}$alkyl)amino, N,N-($C_{1-6}$alkyl)$_2$-amino, $C_1$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl or $C_{1-6}$alkoxy;

$R^3$ is hydrogen, alkyl, halo, $C_{1-6}$alkoxy or $C_{1-6}$ alkyls-;

$R^4$ is hydrogen, $C_{1-6}$ alkyl, halo or $C_{1-6}$alkoxy;

$R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

or a pharmaceutically acceptable salt, solvate, solvate of such a salt or a prodrug thereof; with the proviso that said compound is not 3-(R)-4-(R)-1-(phenyl)-3-[2-(4-fluorophenyl)-2-hydroxyethylsulphanyl]-4-[4-(N-{N-[(R)-1-(carboxy)-2-(hydroxy)ethyl]carbamoylmethyl}carbamoylmethoxy) phenyl]azetidin-2-one; or 3-(R)-4-(R)-1-(phenyl)-3-[2-(4-fluorophenyl)-2-hydroxyethylsulphanyl]-4-{4-[N-((R)-α-{N-[(S)-1-(carboxy)-2-(hydroxy)ethyl]carbamoyl}benzyl) carbamoylmethoxy]phenyl}azetidin-2-one.

In one aspect of the invention it is provided for a compound of formula I2:

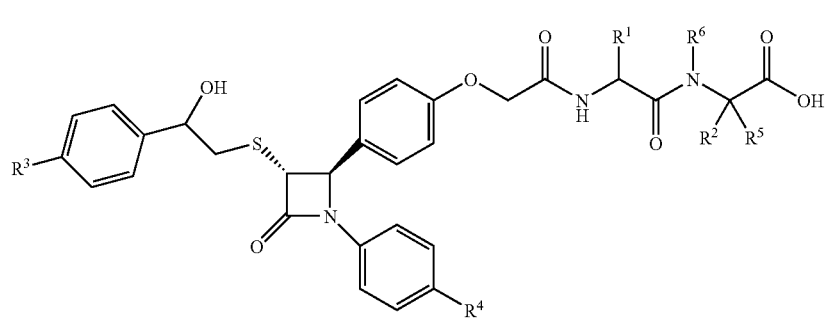

wherein variable groups are defined above as for formula (I). What is said further for formula (I) will, apart from the process schemes below, apply also to formula (I2).

In one aspect of the invention $R^1$ is hydrogen. According to another aspect of the invention, $R^2$ is hydrogen, a branched or unbranched $C_{1-6}$alkyl, $C_{3-6}$cycloalkyl or aryl; wherein said $C_{1-6}$alkyl may be optionally substituted by one or more hydroxy, amino, $C_{1-6}$alkylS(O)$_a$ wherein a is 0-2, $C_{3-6}$cycloalkyl or aryl; and wherein any aryl group may be optionally substituted by hydroxy. According to a further aspect of the invention, $R^3$ is hydrogen, methoxy, or alkyl, for instance a $C_1$-$C_2$alkyl, i.e. methyl or ethyl, for instance methyl, or a halogen, for instance chlorine or fluorine.

According to yet another aspect of the invention $R^4$ is hydrogen or halo, for instance chlorine or fluorine. According to a further aspect of the invention, $R^6$ is hydrogen, aryl$C_{1-6}$ or $R^6$ and $R^2$ form a ring with 3-6 carbon atoms.

According to one aspect of the invention $R^1$ is hydrogen, $R^2$ is a branched or unbranched $C_{1-4}$alkyl, optionally substituted by a $C_{3-6}$cycloalkyl, $R^3$ and $R^4$ are halo, $R^5$ is hydrogen or $C_{1-6}$ alkyl, and $R^6$ is hydrogen.

The invention further provides for one or more compounds chosen from:

N-{[4-((2R,3R)-1-(4-fluorophenyl)-3-{[2-(4-fluorophenyl)-2-hydroxyethyl]thio}-4-oxoazetidin-2-yl)phenoxy] acetyl}glycyl-N-$^6$-acetyl-D-lysine;

1-(4-Fluorophenyl)-3-(R)-[2-(4-fluorophenyl)-2-hydroxyethylthio]-4-(R)-{4-[N-{N-[2-(phenyl)-1-(R)-(carboxy) ethyl]carbamoylmethyl}carbamoylmethoxy] phenyl}azetidin-2-one;

N-{[4-((2R,3R)-1-(4-fluorophenyl)-3-([2-(4-fluorophenyl)-2-hydroxyethyl]thio}-4-oxoazetidin-2-yl)phenoxy] acetyl}glycyl-D-valine;

N-{[4-((2R,3R)-1-(4-fluorophenyl)-3-{[2-(4-fluorophenyl)-2-hydroxyethyl]thio}-4-oxoazetidin-2-yl)phenoxy] acetyl}glycyl-D-tyrosine;

N-{[4-((2R,3R)-1-(4-fluorophenyl)-3-{[2-(4-fluorophenyl)-2-hydroxyethyl]thio}-4-oxoazetidin-2-yl)phenoxy] acetyl}glycyl-D-prolinel N-{[4-((2R,3R)-1-(4-fluorophenyl)-3-{[2-(4-fluorophenyl)-2-hydroxyethyl]thiol-4-oxoazetidin-2-yl)phenoxy] acetyl}glycyl-D-lysine;

N-{[4-((2R,3R)-1-(4-fluorophenyl)-3-([2-hydroxy-2-(4-methoxyphenyl)ethyl]thio}-4-oxoazetidin-2-yl)phenoxy] acetyl}glycyl-D-valine;

N-{[4-((2R,3R)-1-(4-fluorophenyl)-3-{[2-(4-fluorophenyl)-2-hydroxyethyl]thio}-4-oxoazetidin-2-yl)phenoxy] acetyl}glycyl-2-butylnorleucine;

N-{[4-((2R,3R)-1-(4-Fluorophenyl)-3-([2-(4-fluorophenyl)-2-hydroxyethyl]thio}-4-oxoazetidin-2-yl)phenoxy] acetyl}glycyl-5-methyl-L-cysteine;

N-{[4-((2R,3R)-1-(4-chlorophenyl)-3-([2-(4-chlorophenyl)-2-hydroxyethyl]thio}-4-oxoazetidin-2-yl)phenoxy] acetyl}glycyl-3-cyclohexyl-D-alanine;

N-{[4-((2R,3R)-1-(4-fluorophenyl)-3-{[2-(4-fluorophenyl)-2-hydroxyethyl]thio}-4-oxoazetidin-2-yl)phenoxy] acetyl}glycyl-3-cyclohexyl-D-alanine;

N-{[4-((2R,3R)-1-(4-fluorophenyl)$_{73}$-{[2-(4-fluorophenyl)-2-hydroxyethyl]thio}-4-oxoazetidin-2-yl)phenoxy] acetyl}glycyl-4-methyl]eucine;

N-{[4-((2R,3R)-1-(4-Fluorophenyl)-3-{[2-(4-fluorophenyl)-2-hydroxyethyl]thio}-4-oxoazetidin-2-yl)phenoxy] acetyl}-L-alanyl-D-valine;

N-{[4-((2R,3R)-1-(4-fluorophenyl)-3-{[2-hydroxy-2-(4-methylphenyl)ethyl]thio}-4-oxoazetidin-2-yl)phenoxy]acetyl}glycyl-D-valine;

N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-D-valine;

N-{[4-((2R,3R)-1-(4-chlorophenyl)-3-{[2-(4-chlorophenyl)-2-hydroxyethyl]thio-4-oxoazetidin-2-yl)phenoxy]acetyl}glycyl-3-methyl-D-valine;

N-{[4-((2R,3R)-1-(4-fluorophenyl)-3-{[2-(4-fluorophenyl)-2-hydroxyethyl]thio)-4-oxoazetidin-2-yl)phenoxy]acetyl}glycyl-3-(2-naphthyl)-D-alanine;

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-methyl-D-valine;

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-(3R,4S,5R)-3,4,5,6-tetrahydroxy-D-norleucine;

N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl-N, 2-dimethylalanine;

N-({4-[(2R,3R)-1-(4-Fluorophenyl)-3-({2-hydroxy-2-[4-(methylthio)phenyl]ethyl}thio)-4-xoazetidin-2-yl]phenoxy}acetyl)glycyl-3-methyl-D-valine;

N-{[4-((2R,3R)-1-(4-fluorophenyl)-3-{[2-(4-fluorophenyl)-2-hydroxyethyl]thio 3-4 oxoazetidin-2-yl)phenoxy]acetyl}glycyl-S-(4-methylbenzyl)-D-cysteine;

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(tert-butyl)-D-cysteine;

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-b,b-dimethyl-D-phenylalanine.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

The term "aryl" refers to a 4-10 membered aromatic mono or bicyclic ring containing 0 to 5 heteroatoms independently selected from nitrogen, oxygen or sulphur. Examples of aryls include phenyl, pyrrolyl, furanyl, imidazolyl, triazolyl, tetrazolyl, pyrazinyl, pyrimidinyl, pyridazinyl, pyridyl, isoxazolyl, oxazolyl, 1,2,4 oxadiazolyl, isothiazolyl, thiazolyl, 1,2,4-triazolyl, thienyl, naphthyl, benzofuranyl, benzimidazolyl, benzthienyl, benzthiazolyl, benzisothiazolyl, benzoxazolyl, benzisoxazolyl, 1,3-benzodioxolyl, indolyl, pyridoimidazolyl, pyrimidoimidazolyl, quinolyl, isoquinolyl, quinoxalinyl, quinazolinyl, phthalazinyl, cinnolinyl and naphthyridinyl. Particularly "aryl" refers to phenyl, thienyl, pyridyl, imidazolyl or indolyl. The term "aryl" includes both unsubstituted and substituted aromatic rings.

Examples of "$C_{1-6}$alkoxy" include methoxy, ethoxy and propoxy. Examples of "$C_{1-6}$alkylS(O)$_a$ wherein a is 0 to 2" include methylthio, ethylthio, methylsulphinyl, ethylsulphinyl, mesyl and ethylsulphonyl. Examples of "N-($C_{1-6}$alkyl)amino" include methylamino and ethylamino. Examples of "N,N-($C_{1-6}$alkyl)$_2$-amino" include di-N-methylamino, di-(N-ethyl)amino and N-ethyl-N-methylamino. "$C_{3-6}$cycloalkyl" refers to cyclopropyl, cyclobutyl, cyclopentyl and cyclohexyl.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4 position of the benzoyl ring.

A suitable value for an in vivo hydrolysable amide of a compound of the formula (I), or other compounds disclosed herein, containing a carboxy group is, for example, a N-$C_{1-6}$alkyl or N,N-di-$C_{1-6}$alkyl amide such as N-methyl, N-ethyl, N-propyl, N)N-dimethyl, N-ethyl-N-methyl or N,N-diethyl amide.

Some compounds of the formula a) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula a) can exist in solvated as well as unsolvated forms such as, for example, hydrated forms. It is to be understood that the invention encompasses all such solvated forms which possess cholesterol absorption inhibitory activity.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1) reacting a compound of formula (II):

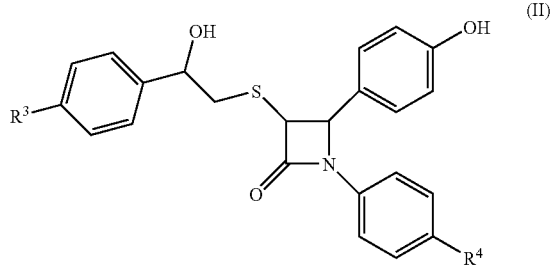

(II)

with a compound of formula (III):

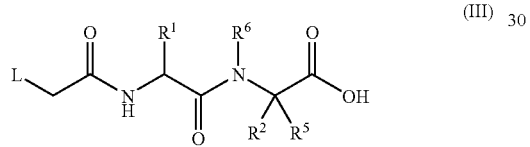

(III)

wherein L is a displaceable group;

Process 2) reacting an acid of formula (IV):

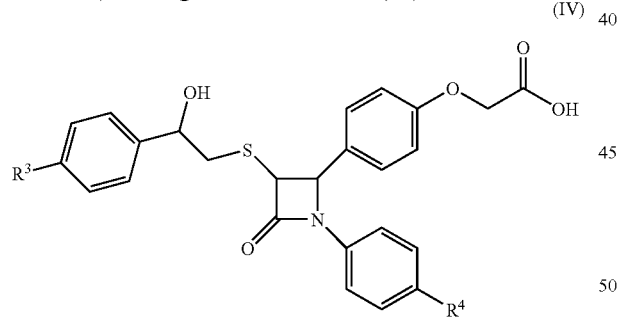

(IV)

or an activated derivative thereof; with an amine of formula (V):

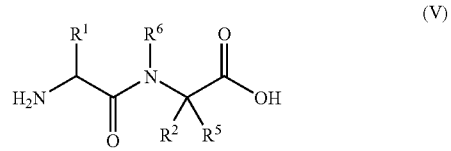

(V)

Process 3): reacting an acid of formula (VI):

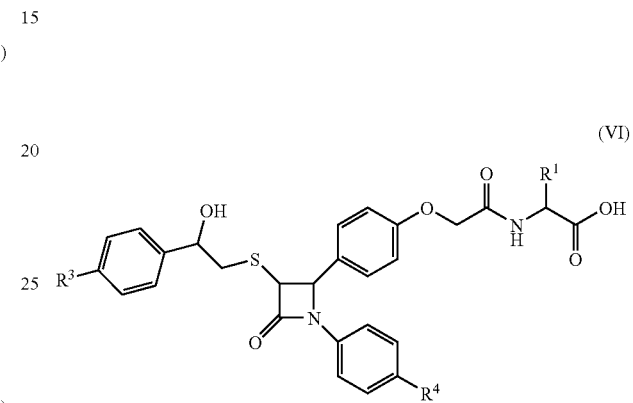

(VI)

or an activated derivative thereof, with an amine of formula (VII):

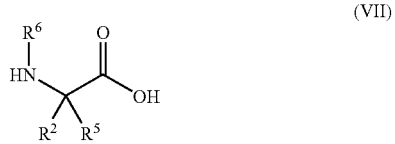

(VII)

Process 4): reducing a compound of formula (VIII):

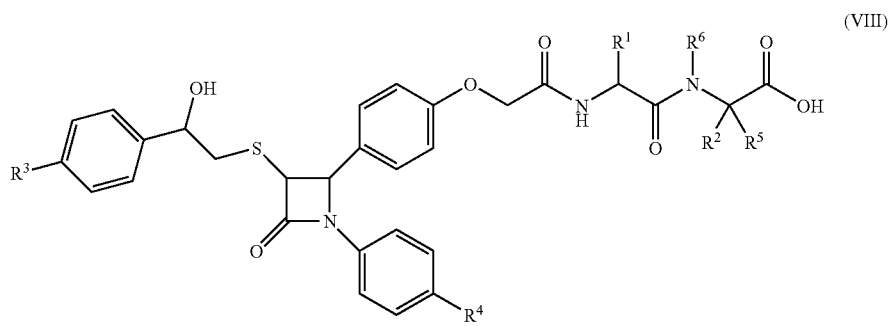

(VIII)

Process 5): reacting a compound of formula (IX):

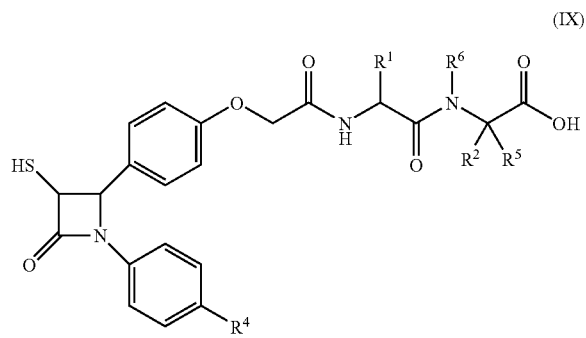

(IX)

with a compound of formula (X):

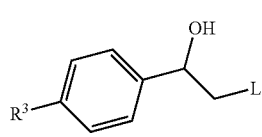

(X)

wherein L is a displaceable group;

Process 6): reacting a compound of formula (XI):

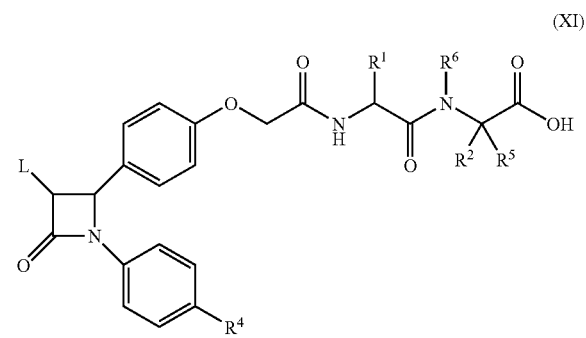

(XI)

wherein L is a displaceable group; with a compound of formula (XII):

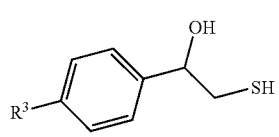

(XII)

Process 7): De-esterifying a compound of formula (XIII)

wherein the group C(O)OR is an ester group;

and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II) may be prepared according to the following scheme:

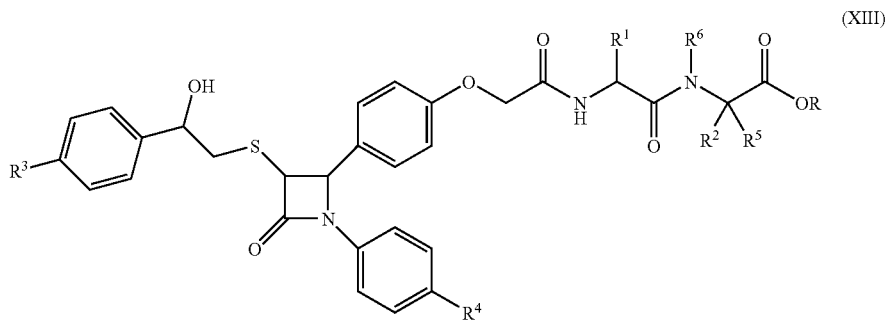

(XIII)

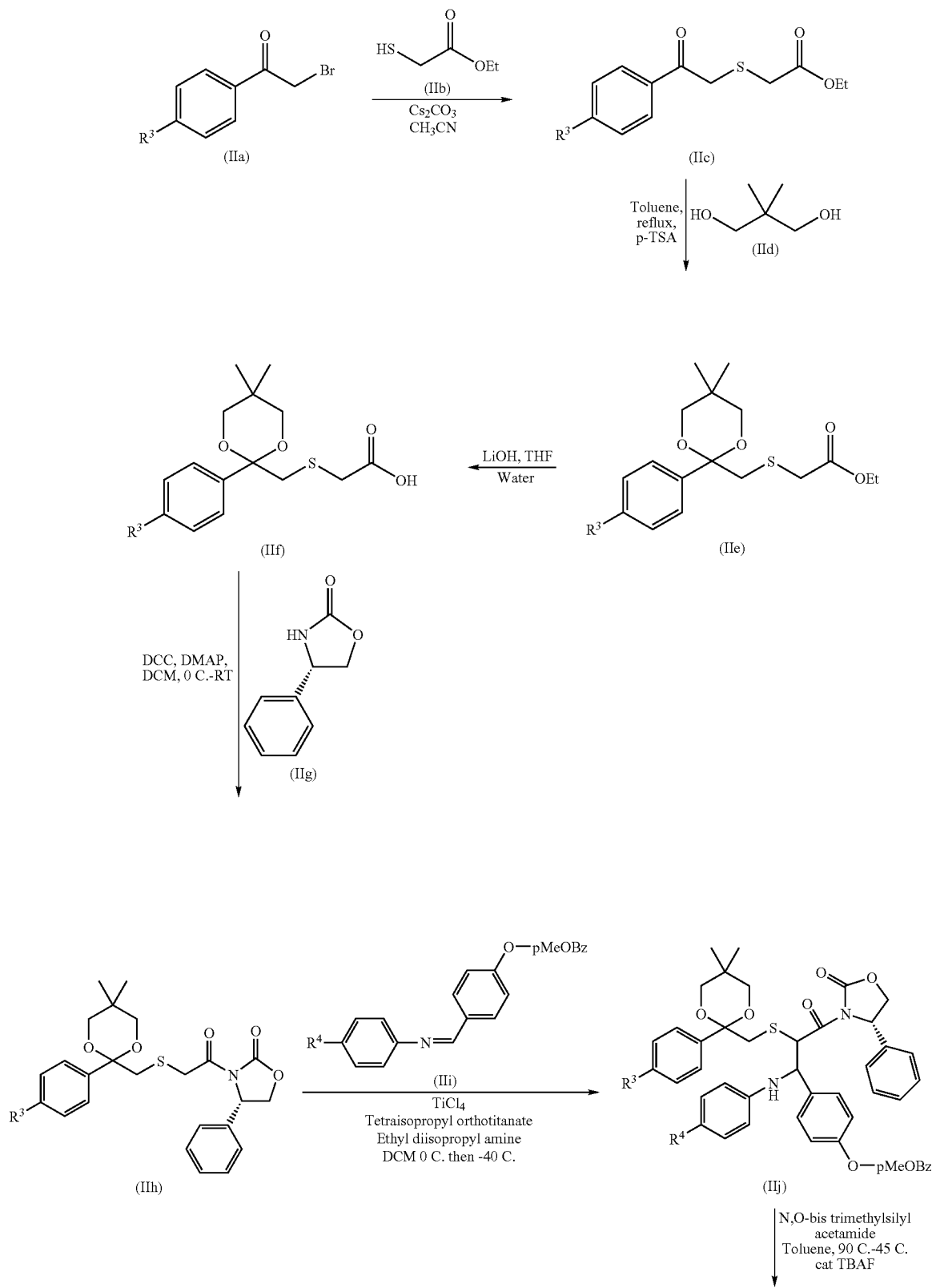
Scheme 1

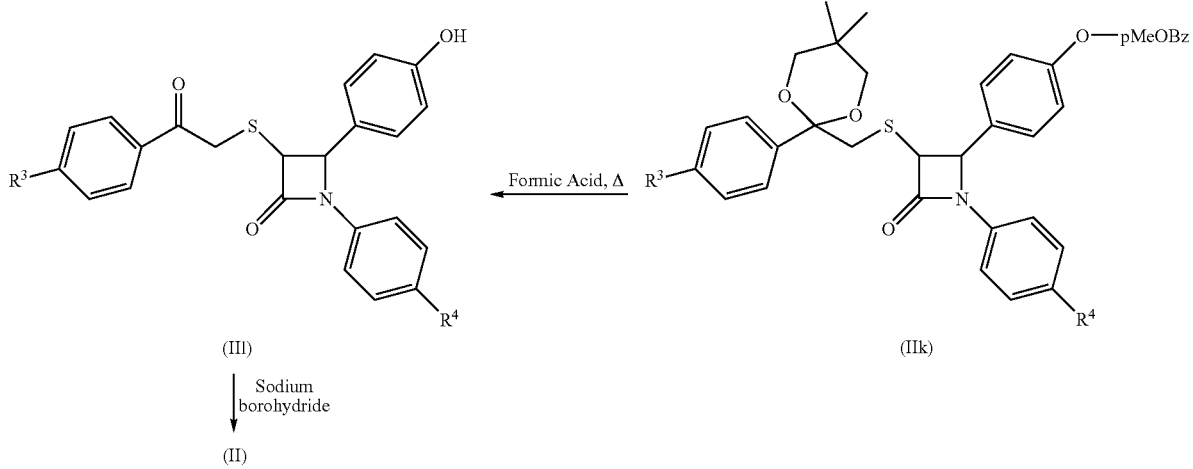

(III) → (IIk) Formic Acid, Δ

Sodium borohydride ↓

(II)

wherein pMeOBz is para methoxy benzyl.

Compounds of formula (IIb), (IId), (IIg) and (III) are commercially available compounds, or they are known in the literature, or they are prepared by standard processes known in the art.

Another aspect of the present invention provides a process for preparing a compound of formula (I2) or a pharmaceutically acceptable salt, solvate, solvate of such a salt or a prodrug thereof which process (wherein variable groups are, unless otherwise specified, as defined in formula (I)) comprises of:

Process 1) reacting a compound of formula (II2):

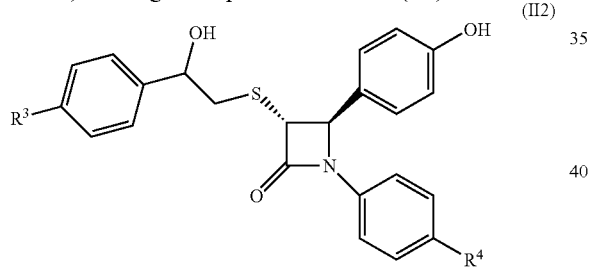

(II2)

with a compound of formula (III):

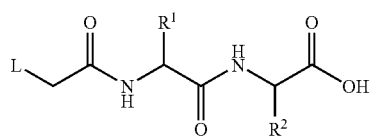

(III)

wherein L is a displaceable group;

Process 2) reacting an acid of formula (IV2):

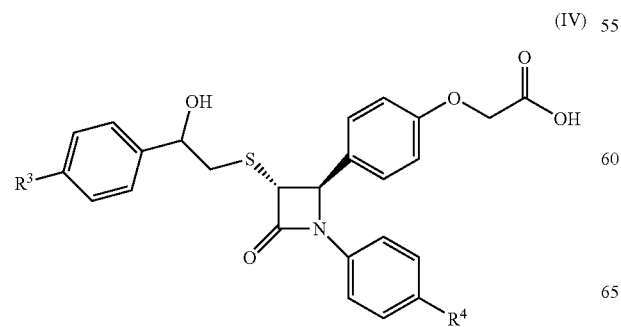

(IV)

or an activated derivative thereof; with an amine of formula (V):

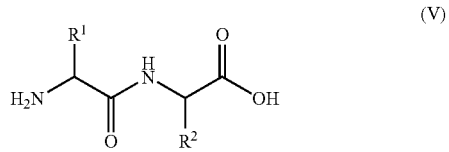

(V)

Process 3): reacting an acid of formula (VI2):

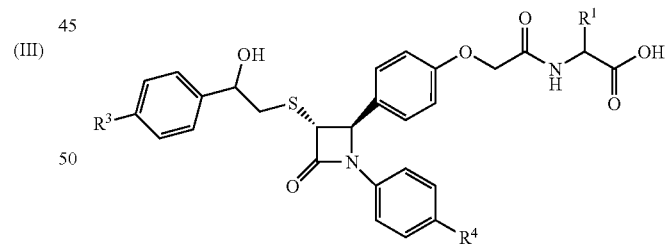

(VI2)

or an activated derivative thereof, with an amine of formula (VII):

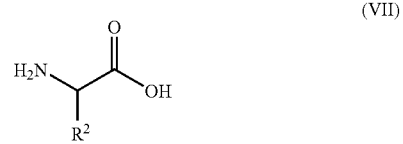

(VII)

Process 4): reducing a compound of formula (VIII2):
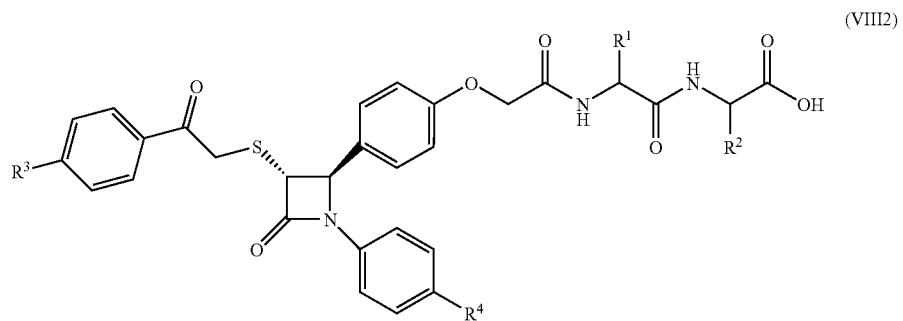
Process 5): reacting a compound of formula (IX2):
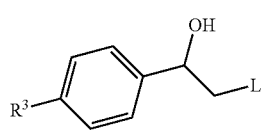
with a compound of formula (X):
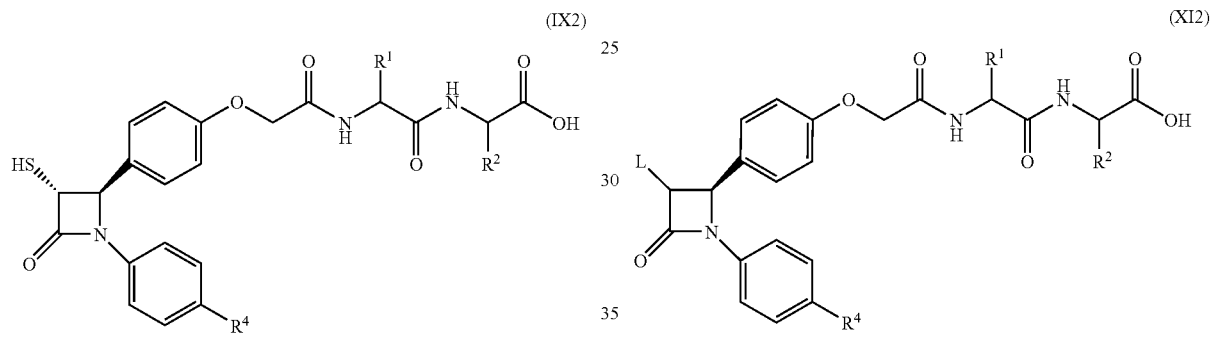
Process 6): reacting a compound of formula (XI2):
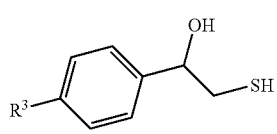
wherein L is a displaceable group; with a compound of formula (XII):
wherein L is a displaceable group;
Process 7): De-esterifying a compound of formula (XIII2)
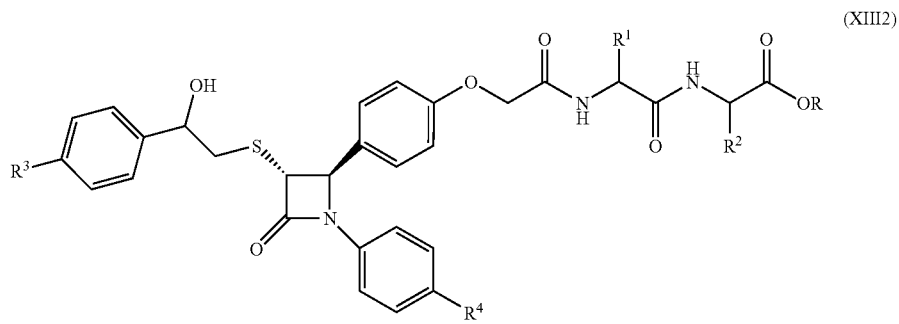

wherein the group C(O)OR is an ester group;
and thereafter if necessary or desirable:
i) converting a compound of the formula (I2) into another compound of the formula (I2);
ii) removing any protecting groups;
iii) forming a pharmaceutically acceptable salt, solvate, solvate of such a salt or a prodrug; or
iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B 1. Alternatively they can be prepared by the following reactions.

Process 1): Alcohols of formula (II2) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II2) may be prepared according to the following scheme:

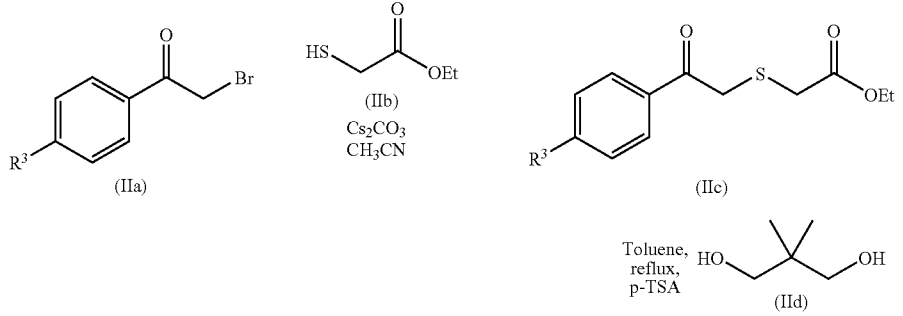

Scheme 1

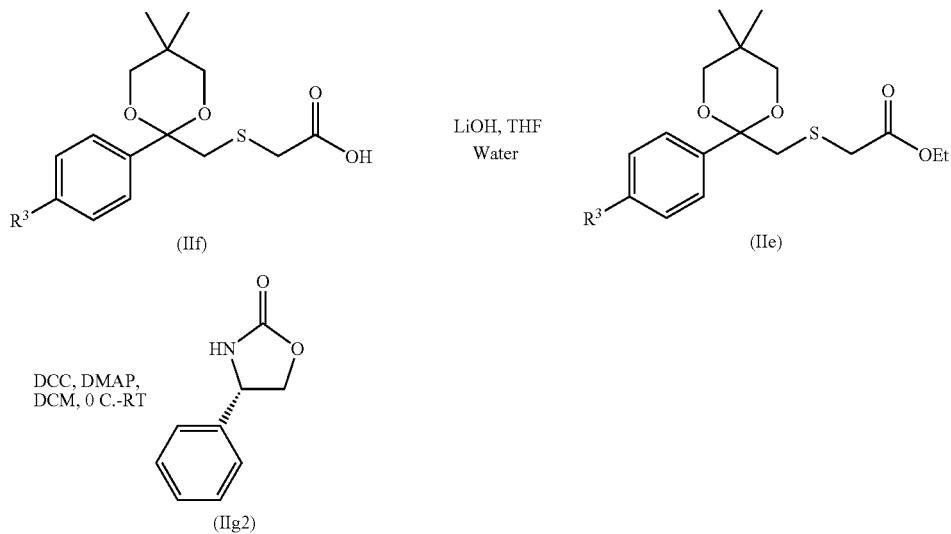

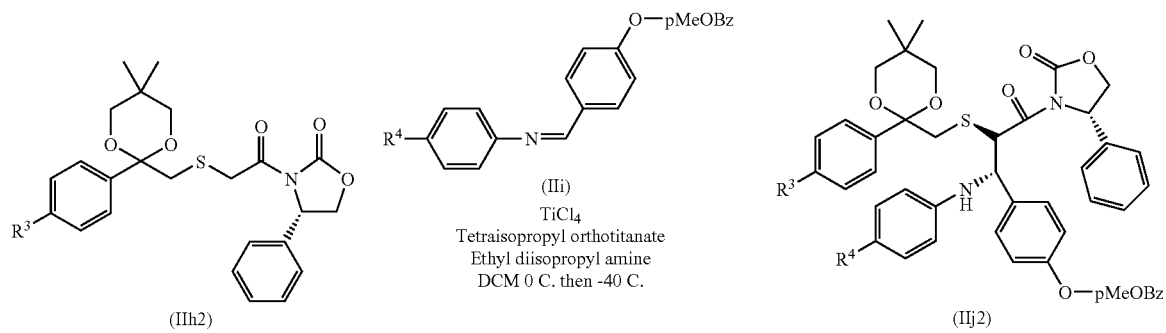
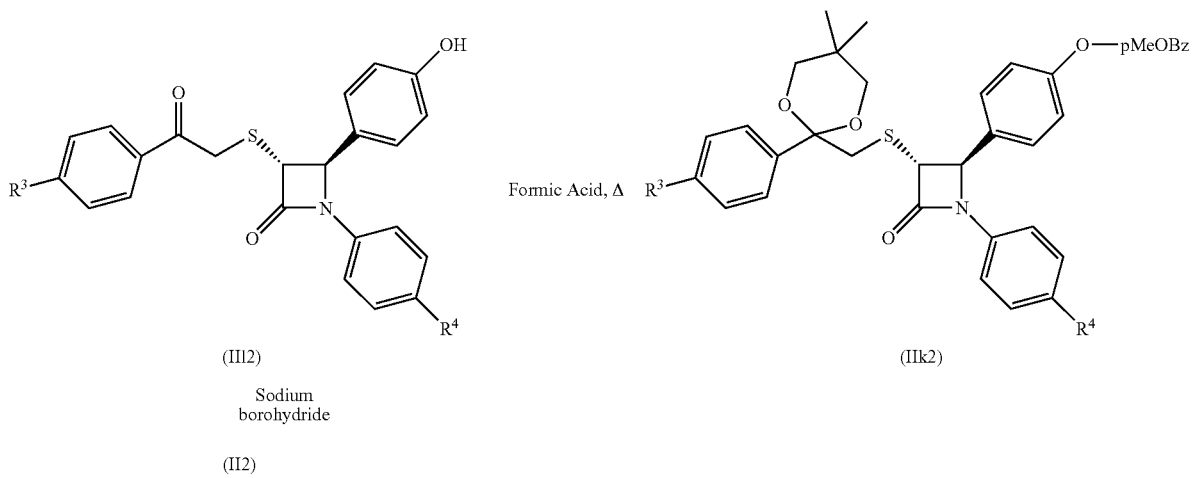
wherein pMeOBz is para methoxy benzyl.
Compounds of formula (Ib), (IId), (Iig2) and (III2) are commercially available compounds, or they are known in the literature, or they are prepared by standard processes known in the art.
A compound of formula (III) may also be reacted with a compound of formula (X).
Compounds of formula (XIV) may be prepared according to the following route:
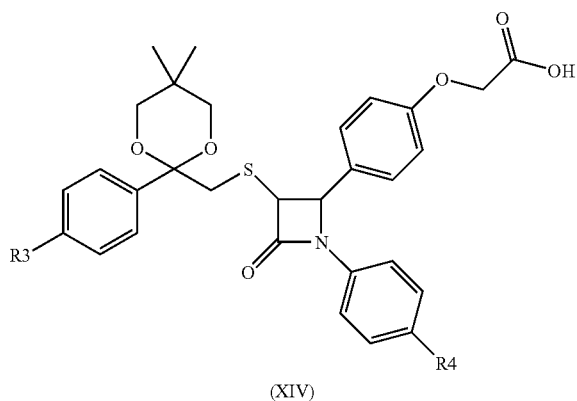

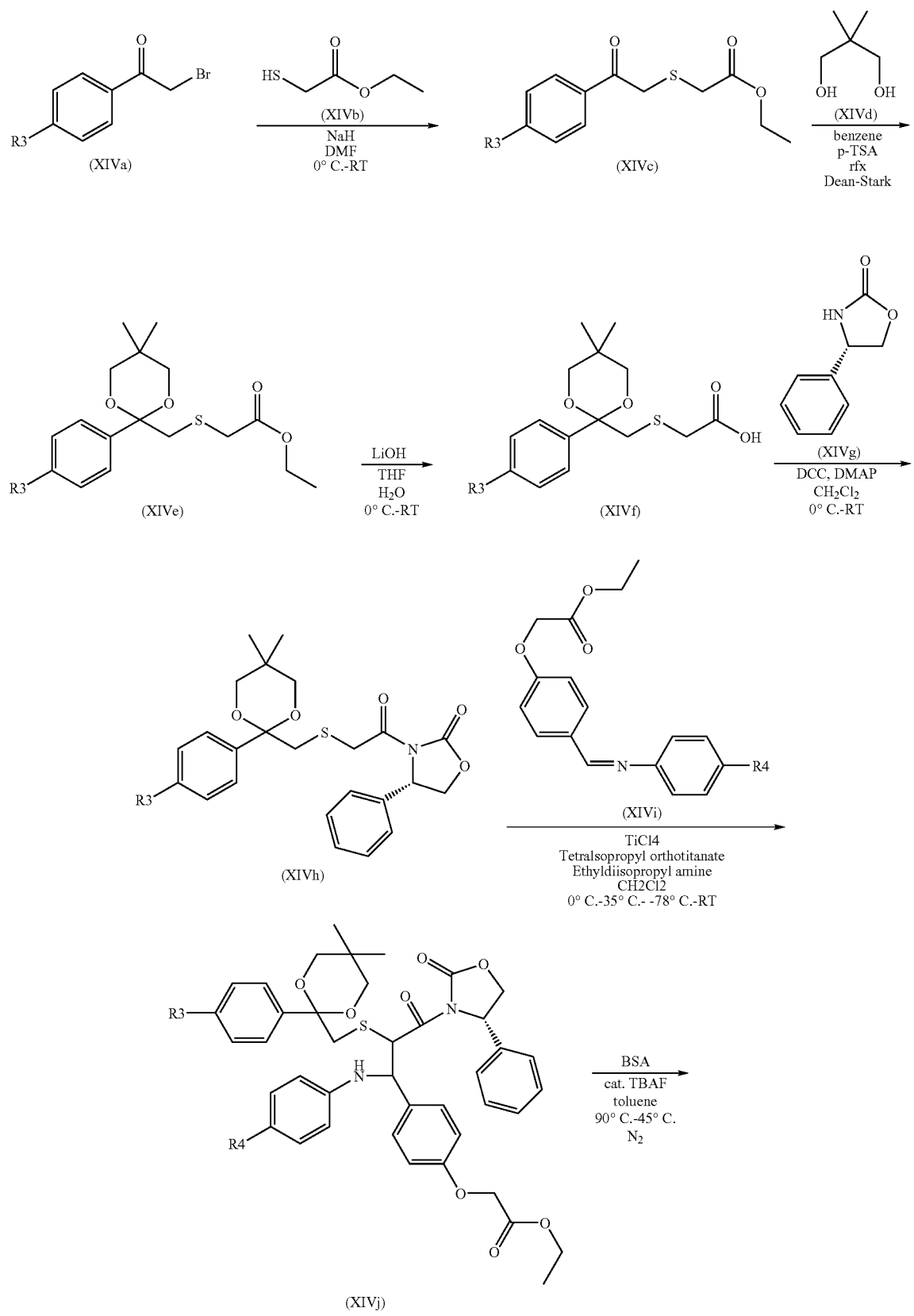

-continued
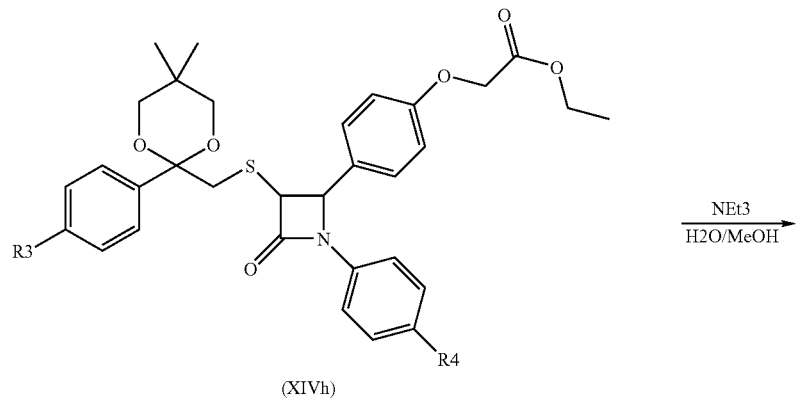
(XIVh)
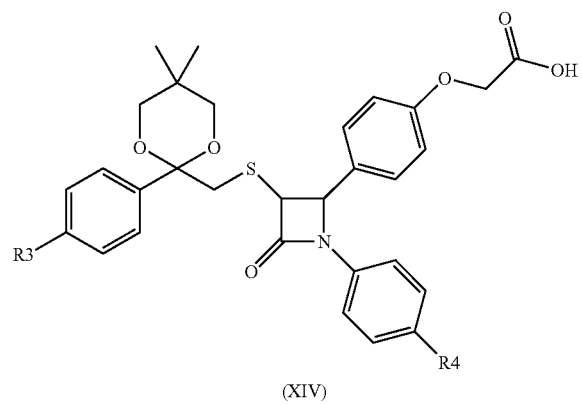
(XIV)
Compounds of formula XIVI may be prepared by the following route:
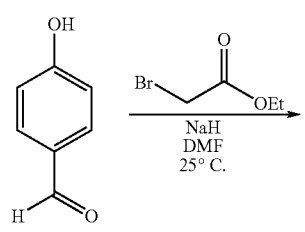
-continued
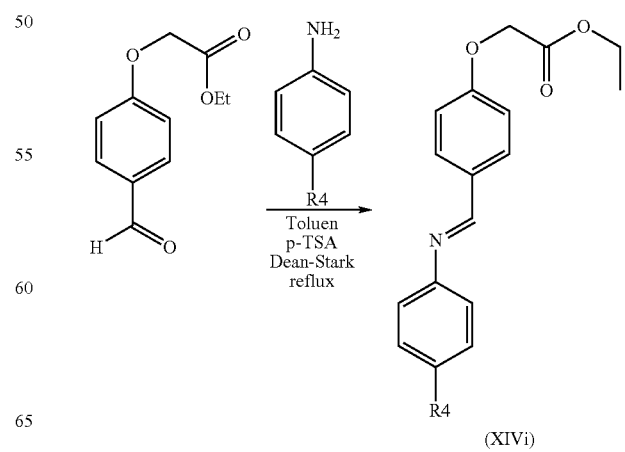
(XIVi)

A compound of formula (III2) may also be reacted with a compound of formula (XIV2).
Compounds of formula (XIV2) may be prepared according to the following route:
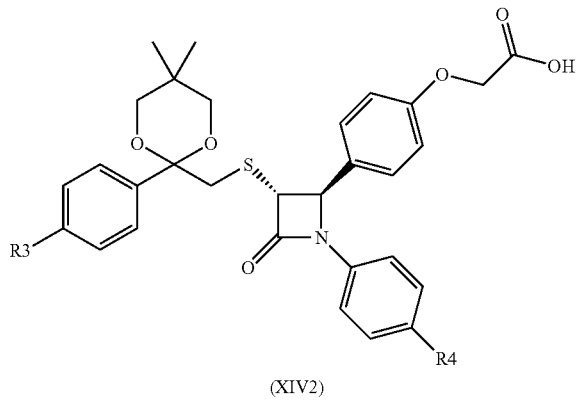
(XIV2)
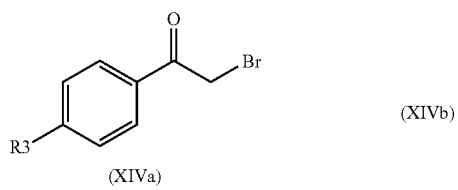
(XIVa)
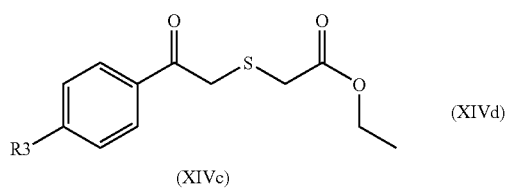
(XIVc)
(XIVb)
(XIVd)
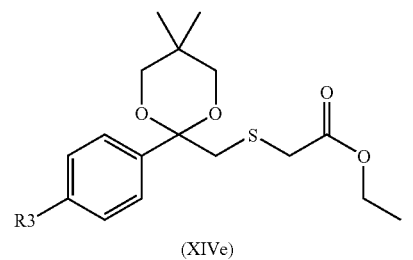
(XIVe)
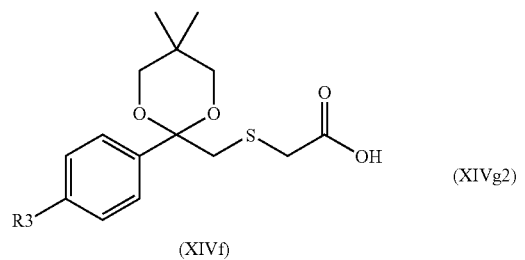
(XIVf)
(XIVg2)
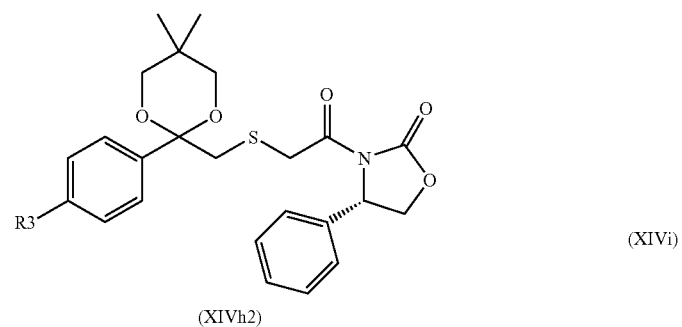
(XIVh2)
(XIVi)

-continued
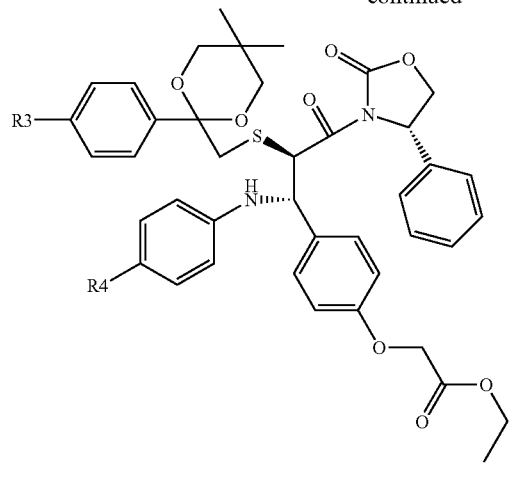
(XIVj2)
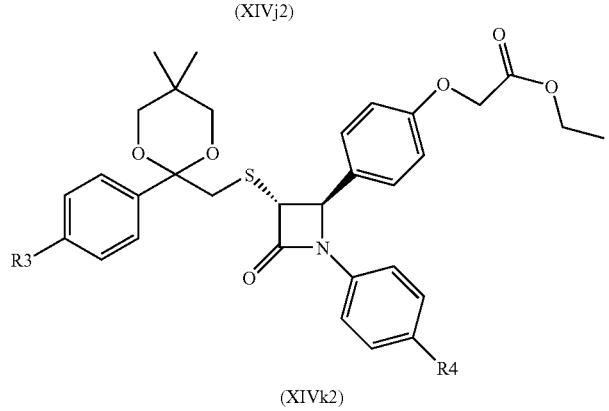
(XIVk2)
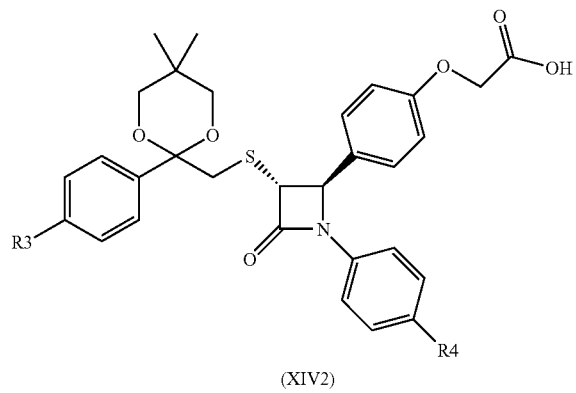
(XIV2)
Compounds of formula XIVl may be prepared by the following route:
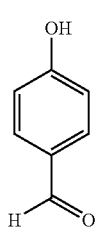 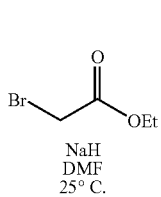 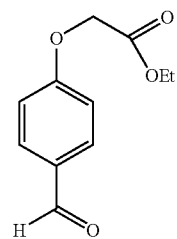
NaH
DMF
25° C.
-continued
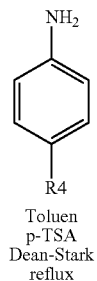
Toluen
p-TSA
Dean-Stark
reflux

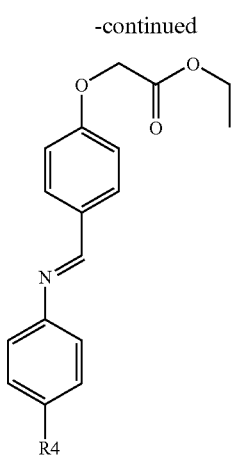

For XIV and XIV2 both, the following applies:

Process 2) and Process 3): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Acids of formula (IV) and (VI) may be prepared from compounds of formula (II) by reacting them with the appropriate, optionally protected, side chain using the conditions of Process 1). Alternatively, acids of formula (V) and (VI) may be prepared by a modification of Scheme I.

Amines of formula (V) and (VII) are commercially available compounds, or they are known in the literature, or they are prepared by standard processes known in the art.

Process 4): Reduction of compounds of formula (VIII) could be performed with a hydride reagent such as sodium borohydride in a solvent such as methanol at temperatures suitable between −20-40° C.

Compounds of formula (VIII) can be prepared from compounds of formula (III), by deprotecting the benzyl group and performing Process 1. Alternatively compound (IIk) could be debenzylated, Process 1 could be performed and the resulting compound deprotected to reveal the ketone.

Process 5) and Process 6): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IX) and (XI) may be prepared by an appropriate modification of Scheme 1.

Compounds of formula (X) and (XII) are commercially available compounds, or they are known in the literature, or they are prepared by standard processes known in the art.

Process 7): Esters of formula (XIII) may be deprotected under standard conditions such as those described below, for example a methyl or ethyl ester may be deprotected with sodium hydroxide in methanol at room temperature.

Compounds of formula (XIII) may be prepared by a modification of any of the processes described herein for the preparation of compounds of formula (I).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

The invention further provides for a compound of the formula (XV) or hydrolysable esters or amides thereof:

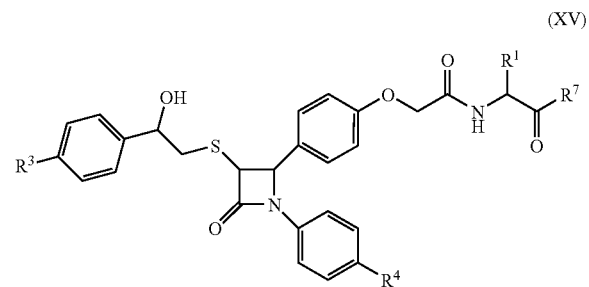

(XV)

wherein $R^7$ is an hydroxy group or a $C_{1-3}$ alkoxy group. $R^1$, $R^3$ and $R^4$ are as defined above regarding formula (I). A compound of formula (XV) may be an intermediate to formula (I).

As stated hereinbefore the compounds defined in the present invention possess cholesterol absorption inhibitory activity. These properties may be assessed, using the following biological tests.

In vivo Testing of Cholesterol Absorption Inhibitors (A)

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Six hours after the $^{14}$C-cholesterol gavage blood samples were taken via the tail and plasma prepared to determine how much cholesterol were absorbed. 24 hours after the gavage of $^{14}$C-cholesterol the mice were bled and plasma were prepared for analysis. Faeces were collected for 24 hours to assess absorption efficiency.

In vivo Testing of Cholesterol Absorption Inhibitors (B).

C57BL/6 female mice were maintained on regular chow diet and housed in individual cages to collect faeces. Mice were fasted for 3 hours and then gavaged with vehicle or compound. One to ten hours later the mice were gavaged with radiolabelled cholesterol. Six hours after the $^{14}$C-cholesterol gavage blood sample was taken via the tail and plasma prepared to determine how much cholesterol was absorbed. 24 hours after the gavage of $^{14}$C-cholesterol the mice were bled and plasma analysed for radioactivity. Faeces were also collected for 24 hours to assess absorption efficiency.

References
1. E. A. Kirk, G. L. Moe, M. T. Caldwell, J. Å. Lernmark, D. L. Wilson, R. C. LeBoeuf. Hyper- and hypo-responsiveness to dietary fat and cholesterol among inbred mice: searching for level and variability genes. J. Lipid Res. 1995 36:1522-1532.
2. C. P. Carter, P. N. Howles, D. Y. Hui. Genetic variation in cholesterol absorption efficiency among inbred strains of mice. J. Nutr. 1997 127:1344-1348.
3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Administration of 5 μmol/kg of Example 96 gave 87% inhibition of $^{14}$C-cholesterol absorption (procedure A). Administration of 5 μmol/kg of Example 94 gave 89% inhibition of $^{14}$C-cholesterol absorption (procedure A).

Administration of 0.2 μmol/kg of Example 91 gave 58% inhibition of $^{14}$C-cholesterol absorption (procedure A). Administration of 0.2 μmol/kg of Example 85 gave 47% inhibition of $^{14}$C-cholesterol absorption (procedure A).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. A unit dose form such as a tablet or capsule will usually contain, for example 1-250 mg of active ingredient. Preferably a daily dose in the range of 1-50 mg/kg, particularly 0.1-10 mg/kg is employed. In another aspect a daily dose in the rage of 0.01-20 mg/kg is employed. In one aspect of the invention the daily dose of a compound of formula (I) is less than or equal to 100 mg. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral-vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina.

The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzheimer's Disease.

Compounds of formula (I), or a pharmaceutically acceptable salt, solvate, solvate of such a salt or a prodrug thereof may also have value in the treatment or prevention of cholesterol associated tumors. Therefore in a further aspect of the invention, there is provided a compound of formula (I), or a pharmaceutically acceptable salt, solvate, solvate of such a salt or a prodrug thereof, for use in the treatment or prevention of cholesterol associated tumors.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. A suitable squalene synthesis inhibitor is squalestatin 1 and a suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitavastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier. According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a Apo A-1 Mimetic Peptide.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt, solvate, solvate of such a salt or a prodrug thereof. Suitable compounds possessing IBAT inhibitory activity for use in combination with compounds of the present invention have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 00/35889, WO 01/34570, WO 00/38725, WO 00/38726, WO 00/38727, WO 00/38728, WO 00/38729, WO 00/47568, WO 00/61568, WO 01/66533, WO 01/68096, WO 01/68637, WO 02/08211, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 864 582, EP 869 121 and EP 1 070 703 and the contents of these patent applications are incorporated herein by reference. Particularly the named examples of these patent applications are incorporated herein by reference. More particularly claim 1 of these patent application are incorporated herein by reference.

Other suitable classes of IBAT inhibitors for use in combination with compounds of the present invention are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity for use in combination with compounds of the present invention is (3R,5R)-3-butyl-3-ethyl-1,1-dioxido-5-phenyl-2,3,4,5-tetrahydro-1,4-benzothiazepin-8-yl O-D-glucopyranosiduronic acid (EP 864 582).

A further suitable compound possessing IBAT inhibitory activity for use in combination with compounds of the present invention is S-8921 (EP 597 107).

A further suitable IBAT inhibitor for use in combination with compounds of the present invention is the compound:

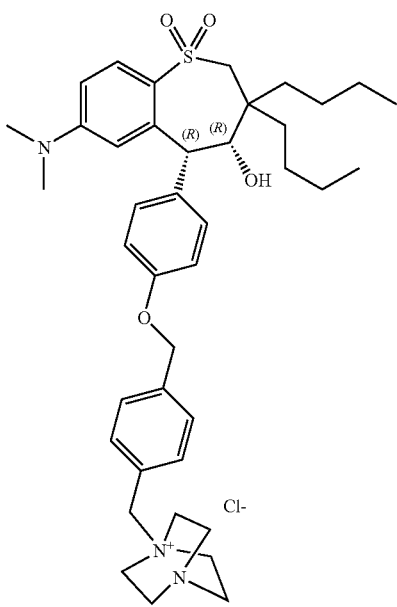

WO 99/32478

A particular IBAT inhibitor for use in combination with compounds of the present invention is selected from any one of Examples 1-120 of WO 02/50051, or a pharmaceutically acceptable salt, solvate, solvate of such a salt or a prodrug thereof, and the compounds of Examples 1-120 are incorporated herein by reference. Claims 1-15 of WO 02/50051 are also incorporated herein by reference. A particular MBAT inhibitor selected from WO 02/50051 for use in combination with compounds of the present invention is selected from any one of:

1,1-dioxo-3,3-dibutyl-5-phenyl-7-methylthio-8-(N-{(R)-1'-phenyl-1'-[N'-(carboxymethyl) carbamoyl]methyl) carbamoylmethoxy)-2,3,4,5-tetrahydro-1,5-benzothiazepine;

1,1-dioxo-3,3-dibutyl-5-phenyl-7-methylthio-8-(N-((R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N-(2-sulphoethyl)carbamoyl]methyl) carbamoylihethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl) carbamoylmethoxy)-2,3,4,5-tetrahydro-1,5-benzothiazepine; 1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl) carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1, 5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N"-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{-[N'-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-[(R)-α-(N'-{2-[(hydroxy)(methyl)phosphoryl] ethyl}carbamoyl)benzyl]carbamnoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N[(R)-α-(N-{2-[(methyl)(ethyl) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl] benzyl}carbamoylmethoxy)-2,3,4,5-tetrahydro-1,5-benzothiazepine; and 1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular IBAT inhibitor selected from WO 03/020710 for use in combination with compounds of the present invention is selected from any one of:

1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-((S)-1-carbamoyl-2-hydroxyethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(hydroxycarbamoyl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(N'-pyrimidin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N-((R)-α-({N'-[2-(N'-pyridin-2-ylureido)ethyl]carbamoyl benzyl)carbamoylmethoxy]-2,3,4,5-tetrahydro-1,5-benzothiazepine;

1,1-dioxo-3-butyl-3-ethyl-5-phenyl-7-methylthio-8-(N'-{(R)-α-[N'-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(3,4-dihydroxyphenyl)-2-methoxyethyl]carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N-{(R)-α-[N'-(2-aminoethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(piperidin-4-ylmethyl) carbamoyl]benzyl}carbamoylmethoxy)-2,3,4,5-tetrahydro-1,5-benzothiazepine; or 1,1-dioxo-3-butyl-3-ethyl-5-phenyl-7-methylthio-8-(N-{(R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular MBAT inhibitor selected from WO 03/022825 for use in combination with compounds of the present invention is selected from any one of:

1,1-dioxo-3(R)-3-butyl-3-ethyl-5-(R)-5-phenyl-8-[N-((R)-α-carboxybenzyl) carbamoylmethoxy]-2,3,4,5-tetrahydro-1,4-benzothiazepine;

1,1-dioxo-3(S)-3-butyl-3-ethyl-5-(S)-5-phenyl-8-[N-((R)-α-carboxybenzyl) carbamoylmethoxy]-2,3,4,5-tetrahydro-1,4-benzothiazepine;

1,1-dioxo-3-(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3-(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-(S)-3-ethyl-3-butyl-4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]-4-hydroxybenzyl) carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

A particular IBAT inhibitor for use in combination with compounds of the present invention is selected from any one of Examples 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular IBAT inhibitor selected from WO 03/022830 for use in combination with compounds of the present invention is selected from any one of:

1,1-dioxo-3-butyl-3-ethyl-4-hydroxy-5-phenyl-7-(N-{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N-{(R)-α-[N-(2-sulphoethyl)carbamoyl]-4-ydroxybenzyl}carbamoylmethylthio)-2,3,4,5-tetrahydrobenzothiepine ammonia salt 1,1-dioxo-3-butyl-3-ethyl-4-hydroxy-5-phenyl-7-{N-[α-(carboxy)-2-fluorobenzyl]arbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]arbamoylmethylthio}-2, 3,4,5-tetrahydrobenzothiepine or a pharmaceutically acceptable salt, solvate, solvate of such a salt or a prodrug thereof.

A particular IBAT inhibitor for use in combination with compounds of the present invention is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular IBAT inhibitor selected from WO 03/022286 for use in combination with compounds of the present invention is selected from any one of:

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl) carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl]-4-hydroxybenzyl}carbaamoylmethoxy)-2,3,4,5-tetrahydro-1,2,5-benzothiadiazepine; and 1,1-dioxo-3,3-dibutyl-5-phenyl-7-methylthio-8-[N-{(R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/091232, or a pharmaceutically acceptable salt, solvate, solvate of such a salt or a prodrug thereof, and the compounds of Examples 1-7 are incorporated herein by reference. Claims 1-10 of WO 03/091232 are also incorporated herein by reference. A particular IBAT inhibitor selected from WO 03/091232 for use in combination with compounds of the present invention is selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxy-hexyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxy-hexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-{(R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-{N-[(R)-α-(N-{2-(S)-[N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N-((R)-α-N-[2-(3,4,5-trihydroxyphenyl)ethyl]carbamoyl}benzyl)carbamoylmethoxy]-2,3,4,5-tetrahydro-1,2,5-benzothiadiazepine; and 1,1-Dioxo-3,3-dibutyl-5-phenyl-7-methylthio-8-(N-{(R)-α-[N-(2-(R)-3-(S)$_4$-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solate, solvate of such a salt or a prodrug thereof.

Further suitable compounds possessing IBAT inhibitory activity for use in combination with compounds of the present invention are disclosed in WO 031106482.

Suitable IBAT inhibitors as disclosed in WO 03/106482 for use in combination with compounds of the present invention are selected from any one of:

1,1-dioxo-3,3-dibutyl-5-phenyl-7-methylthio-8-(N-{(R)-α-[N'-((S)-1-carboxyethyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxybutyl) carbamoyl]benzyl carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl) carbamoyl]-4-hydroxybenzyl}carbaamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl) carbamoyl]-4-hydroxybenzyl}carbaamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl) carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl)carbamoylmethoxy)-2,3,4,5-tetrahydro-1,5-benzothiazepine; or 1,1-dioxo-3,3-dibutyl-5-phenyl-7-methylthio-8-(N'-(R)-α-[N'-((S)-1-carboxyethyl) carbamoyl]benzyl}carbamoylmethoxy)-2,3,4,5-tetrahydro-1,5-benzothiazepine.

or a pharmaceutically acceptable salt, solvate, solvate of such a salt or a prodrug thereof.

Further suitable IBAT inhibitors for use in combination with compounds of the present invention are those disclosed in WO 04/076430.

In a particular aspect of the invention an EBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an IBAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an BAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) an IBAT inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an IBAT inhibitor, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and an EBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO03/051821, WO03/051822, WO03/051826, PCT/GB03/02584, PCT/GB03/02591, PCT/GB03/02598, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, NN622/Ragaglitazar, BMS 298585, BRL49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) a PPAR alpha and/or gamma agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an agonists to the receptor HM74A (nicotinic acid receptor). HM74A agonists may be nicotine acid derivates. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

Therefore, in an additional feature of the invention, there is provided a combination of a compound of formula (I), or a pharmaceutically acceptable salt, solvate, solvate of such a salt or a prodrug thereof and a nicotinic acid derivative or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a nicotinic acid derivative, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captoprilglutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolapnrlat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat);

an angiotensin II receptor antagonist (for example candesartan, candesartan cilexetil, losartan, valsartan, irbesartan, tasosartan, telmisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alpha/beta andrenergic blocker;

an andrenergic stimulant (for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil);

anti-coagulants (selected from argatroban, bivalirudin, dalteparin sodium, desirudin, dicumarol, lyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xernilofiban, monoclonal antibody 7E3 and sibrafiban)

platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)

hemorrheologic agents (for example pentoxifylline);

lipoprotein associated coagulation inhibitors;

Factor VIIa inhibitors;

Factor Xa inhibitors;

low molecular weight heparins (for example enoxaparin, nardroparin, dalteparin, certroparin, parnaparin, reviparin and tinzaparin);

squalene synthase inhibitors;

squalene epoxidase inhibitors;

liver X receptor (LXR) agonists for example GW-3965 and those described in WO00224632, WO00103705, WO02090375 and WO00054759 (claim 1 and the named examples of these four application are incorporated herein by reference);

microsomal triglyceride transfer protein inhibitors for example implitapide and those described in WO03004020, WO03002533, WO02083658 and WO 00242291 (claim 1 and the named examples of these four application are incorporated herein by reference);

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

Many of the intermediates described herein are novel and are thus provided as a further feature of the invention. For example compounds of formula (VI) show cholesterol absorption inhibitory activity when tested in the above referenced in vitro test assay and are thus claimed as a further feature of the invention.

Thus in a further feature of the invention, there is provided a compound of formula (VI), or a pharmaceutically acceptable salt, solvate, solvate of such a salt or a prodrug thereof, with the proviso that said compound is not 3-(R)-4-(R)-1-(phenyl)-3-[2-(4-fluorophenyl)-2-ydroxyethylsulphanyl]-4-{4-[N-(carboxymethyl)carbamoylmethoxy]phenyl}azetidin-2-one.

Therefore according to a further aspect of the invention there is provided a pharmaceutical composition which comprises a compound of formula (VI), or a pharmaceutically acceptable salt, solvate, solvate of such a salt or a prodrug thereof in association with a pharmaceutically-acceptable diluent or carrier, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to an additional aspect of the present invention there is provided a compound of the formula (VI), or a pharmaceutically acceptable salt, solvate, solvate of such a salt or a prodrug thereof, for use in a method of prophylactic or therapeutic treatment of a warm-blooded animal, such as man, with the proviso that said compound is not 3-(R)-4-(R)-1-(phenyl)-3-[2-(4-fluorophenyl)-2-hydroxyethylsulphanyl]-4-{4-[N-(carboxymethyl) carbamoylmethoxy]phenyl}azetidin-2-one.

Thus according to this aspect of the invention there is provided a compound of the formula (VI), or a pharmaceutically acceptable salt, solvate, solvate of such a salt or a prodrug thereof, for use as a medicament, with the proviso that said compound is not 3-(R)-4-(R)-1-(phenyl)-3-[2-(4-fluorophenyl)-2-hydroxyethylsulphanyl]){4-[N-(carboxymethyl) carbamoylmethoxy]phenyl}azetidin-2-one.

According to another feature of the invention there is provided the use of a compound of the formula (VI), or a pharmaceutically acceptable salt, solvate, solvate of such a salt or a prodrug thereof, in the manufacture of a medicament for use in the production of a cholesterol absorption inhibitory effect in a warm-blooded animal, such as man, with the proviso that said compound is not 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to another feature of the invention there is provided the use of a compound of the formula (VI), or a pharmaceutically acceptable salt, solvate, solvate of such a salt or a prodrug thereof, in the manufacture of a medicament for use in the treatment of hyperlipidaemic conditions in a warm-blooded animal, such as man, with the proviso that said compound is not 3-$(R)_4$-(R)-1-(phenyl)-3-[2-(4-fluorophenyl)-2-hydroxyethylsulphanyl]-4-{4-[N-(carboxymethyl)carbamoylmethoxy]phenyl}azetidin-2-one.

According to a further feature of this aspect of the invention there is provided a method for producing a cholesterol absorption inhibitory effect in a warm-blooded animal, such as man, in need of such treatment which comprises administering to said animal an effective amount of a compound of formula (VI), or a pharmaceutically acceptable salt, solvate, solvate of such a salt or a prodrug thereof, with the proviso that said compound is not 3-$(R)_4$-(R)-1-(phenyl)-3-[2-(4-fluorophenyl)-2-hydroxyethylsulphanyl]-4-(4-[N-(carboxymethyl)carbamoylmethoxy]phenyl}azetidin-2-one.

According to a further feature of this aspect of the invention there is provided a method of treating hyperlipidemic conditions in a warm-blooded animal, such as man, in need of such treatment which comprises administering to said animal an effective amount of a compound of formula (VI), or a pharmaceutically acceptable salt, solvate, solvate of such a salt or a prodrug thereof, with the proviso that said compound is not 3-$(R)_4$-(R)-1-(phenyl)-3-[2-(4-fluorophenyl)-2-hydroxyethylsulphanyl]-4-{4-[N-(carboxymethyl) carbamoylmethoxy]phenyl}azetidin-2-one.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;

(iii) column chromatography (by the flash procedure) was performed on Silica gel 40-63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MD spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets;

Mass spectra were recorded on one of the following instruments: LCT, QTOF, ZQ Mass spectrometer, all from Waters.

LC-MS:

Separation was performed using Agilent 1100 Series Modules or Waters 1525 pump on a Synergi MAX-RP (Phenomenex) C12 3×50 mm 4 μm with gradient elution.

Samples were injected using Waters 2700 Sample Manager.

Mobile phases:

Generic gradients were applied from 5% to 95% acetonitrile.

Buffers containing 10 mM ammonium acetate or 5 mM ammonium formiate/5 mM formic acid were used.

The mass spectra were recorded with a Waters ZQ2000 or Waters ZMD equipped with an electrospray interface, swithing positive and negative ionization mode. UV spectra were collected by a Aglent 1100 PDA or Waters 2996 DAD and the evaporative light scattering (ELS) signal by a Sedere Sedex 55 or 75.

Data collection and evaluation were performed using the MassLynx software.

Accurate mass data were determined using either a LCT or QTOF MS (Waters) with leucine enkephaline (m/z 556.2771) as lockmass. Unless otherwise stated the mass ion quoted is (MH+).

Unless further details are specified in the text, analytical high performance liquid chromatography (HPLC) was performed on Prep LC 2000 (Waters), Cromasil $C_8$, 7 μm, (Akzo Nobel); MeCN and de-ionised water 10 mM ammonium acetate as mobile phases, with suitable composition;

(vii) intermediates were not generally fully characterised and purity was assessed by thin layer chromatography (TLC), HPLC, infra-red (IR), MS or NMR analysis;
(viii) where solutions were dried sodium sulphate was the drying agent; and
(ix) the following abbreviations may be used hereinbefore or hereinafter:—
DCM dichloromethane;
DMF N,N-dimethylformamide;
TBTU o-Benzotriazol-1-yl-N,N,N',N'-tetramethyluronium tetrafluoroborate;
EtOAc ethyl acetate;
MeCN acetonitrile;
TFA trifluoroacetic acid;
DMAP 4-(dimethylamino)pyridine;
BSA N,O-Bis(trimethylsilyl)acetamide; and
TBAF tetrabutylammonium fluoride;
NMM N-methyl morpholine;
TFA triethylamine;
DBN 1,5-diazabicyclo-[4,3,0]-non-5-ene.

Example 1

(2R)-[(N-{[4-((2R,3R)-1-(4-fluorophenyl)-3-([2-(4-fluorophenyl)-2-hydroxyethyl]thio)-4-oxoazetidin-2-yl)phenoxy]acetyl}glycyl)amino](phenyl)acetic acid N-{[4-((2R,3R)-1-(4-fluorophenyl)-3-{[2-(4-fluorophenyl)-2-oxoethyl]thio}-4-oxoazetidin-2-yl)phenoxy]acetyl}glycine (44 mg, 0.081 mmol), N-methylmorpholine (18 ul, 0.16 mmol), tert-butyl (2R)-amino(phenyl)acetate (23 mg, 0.11 mmol) and TBTU (36 mg, 0.11 mmol) were added to methylene chloride (3 ml) and the reaction mixture was stirred at ambient temperature for 1.5 h. The mixture was purified by column chromatography on silica gel using methylene chloride/ethylacetate (1/1) as eluent. The resulting intermediate ester was dissolved in formic acid (2 ml) and the mixture was stirred overnight at 45° C. The solvent was evaporated under reduced pressure and was co-evaporated with toluene. The residue was dissolved in methanol (2 ml) and NaBH4 10 mg, 0.26 mmol) was added. The reaction mixture was stirred at ambient temperature for 15 min. A small amount of amnmnoniumacetate buffer was added and the methanol was evaporated off. The residue was purified by preparativ HPLC using acetonitril/ammonium acetat buffer (45:55) as eluent. The collected fractions were lyophilized to obtain 39 mg (71%, 3 steps) of the title compound. ($^1$H-NMR, 400 MHz, CD$_3$OD): 1.8-2.0 (m, 2H), 3.75 (d, 2H), 4.3 (d, 1H), 4.55 (s, 2H), 4.65-4.80 (m, 2H), 5.05 (d, 1H), 7.0-7.4 (m, 17H), 7.95 (dd, 1H) 8.25 (t, 1H)

Example 2

N-{[4-((2R,3R)-1-(4-fluorophenyl)-3-{[2-(4-fluorophenyl)-2-hydroxyethyl]thiol-4-oxoazetidin-2-yl)phenoxy]acetyl}glycyl-N$^6$-acetyl-D-lysine N-{[4-((2R,3R)-1-(4-fluorophenyl)-3-{[2-(4-fluorophenyl)-2-oxoethyl]thio}-4-oxoazetidin-2-yl)phenoxy]acetyl}glycine (20 mg, 0.037 mmol), N-methylmorpholine (18 ul, 0.16 mmol) and TBTU (13 mg, 0.041 mol) were added to CH$_2$Cl$_2$ (2 ml) and the reaction mixture was stirred at 30° C. for, 1.5 h. To the mixture were N$^6$-acetyl-D-lysine (14 mg, 0.074 mmol) and DMF (5 drops) added and the mixture was stirred at ambient temperature. overnight. The solvent was evaporated under reduced pressure and methanol (2 ml) and NaBH4 (30 mg, 0.79 mmol) were added to the residue. The reaction mixture was stirred at ambient temperature for 1 h. A small amount of ammoniumacetate buffer was added and the methanol was evaporated off. The residue was purified by preparativ HPLC using acetonitril/ammonium acetat buffer (40:60) as eluent. The collected fractions were lyophilized, solved in tert-butanol and lyophilized again to obtain 4 mg (15% 2 steps) of the title compound. ($^1$H-NMR, 400 MHz, DMSO-d$_6$): 1.2-1.8 (m, 1H), 2.85-2.95 (m, 2H), 3.7-3.8 (m, 2H), 4.0-4.1 (bs, 1H), 4.25-4.3 (m, 1H), 4.5 (s, 2H), 4.7-4.8 (m, 1H), 5.05 (dd, 1H), 6.95-7.4 (m, 12H), 7.7-7.8 (m, 1H), 7.95-8.05 (m, 1H, 8.25-8.3 (m, 1H)

Example 3

N-{[4-((2R,3R)-1-(4-fluorophenyl)-3-{[2-(4-fluorophenyl)-2-hydroxyethyl]thio}-4-xoazetidin-2-yl)phenoxy]acetyl}-D-alanyl-D-phenylalanine N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-alanine (12 mg, 0.022 mmol), tert-butyl D-phenylalaninate hydrochloride (7 mg, 0.028 mmol) and 4-methylmorpholine (7 mg, 0.065 mmol were dissolved in 0.5 ml DCM. The mixture was stirred at room temperature for 5 minutes. TBTU (9 mg, 0.028 mmol) was added and the reaction mixture was stirred overnight and then purified on silica (2 g), first with DCM and then with DCM:MeOH, 10:1 as eluent. The fractions containing the product were concentrated and formic acid (1 ml) was added and the solution was stirred overnight. The formic acid was evaporated whereafter residual formic acid was removed by addition of toluene and evaporation. The residue was stirred in methanol: triethylamine, 40:1, (2 ml) for 2.5 days (hydrolysis of the formed formic acid ester), the mixture was concentrated and the residue was purified by preparative HPLC using a gradient from 20% to 100% CH3CN in 0.1% ammonium acetate buffer as eluent. Freeze-drying gave 7.3 mg (48%) of the title product. M/z: 702.3 (M–1), NMR (DMSO, 400 MHz): 1.18 (d, 3H), 2.85-2.96 (m, 3H), 3.00-3.07 (m, 1H), 4.05-4.12 (m, 1H), 4.19-4.32 (m, 2H), 4.48 (dd, 2H), 4.68-4.76 (m, 1H), 5.0-5.07 (m, 1H), 6.89-6.95 (m, 2H), 7.05-7.17 (m, 10H), 7.19-7.25 (m, 2H), 7.30-7.36 (m, 4H), 7.65-7.75 (m, 1H), 8.12-8.18 (m, 1H).

Example 4

N²-[(2R)-2-({[4-((2R,3R)-1-(4-fluordphenyl)-3-{[2-(4-fluorophenyl)-2-hydroxyethyl]thio]-4-oxoazetidin-2-yl)phenoxy]acetyl}amino)-2-phenylacetyl]-D-lysine (2R)-({([4-((2R,3R)-1-(4-fluorophenyl)-3-{[2-(4-fluorophenyl)-2-hydroxyethyl]thio}-4-oxoazetidin-2-yl)phenoxy]acetyl}amino)(phenyl)acetic acid (10 mg, 0.016 mmol), tert-butyl N⁶-(tert-butoxycarbonyl)-D-lysinate hydrochloride (7 mg, 0.021 mmol) and N-methylmorpholine (5 mg, 0.048 mmol) were dissolved in DCM (0.5 ml). The mixture was stirred and after 5 min TBTU (7 mg, 0.021) was added and the reaction mixture was stirred for two hours. The product was purified on a silica plug with DCM:MeOH, 100:5 as the eluent. Formic acid (0.5 ml) was added to the purified product and the mixture was stirred two hours at 40° C. and then at ambient temperature overnight. The formic acid was removed under reduced pressure and toluene was added whereafter the solvent was removed. The residue was dissolved in MeOH and a small amount of triethylamine and stirred overnight at ambient temperature. The product was purified by preparative HPLC (CH3CN/0.1% ammonium acetate 20:80-100:0). The fractions containing the product were lyophilized and 4.0 mg (33%) of the title compound was obtained. M/z: 745.4 (M−1). NMR (DMSO, 400 MHz): 1.19-2.30 (m, 2H), 1.30-1.40 (m, 2H), 1.40-1.52 (m, 2H), 1.52-1.68 (m, 2H), 2.63-2.75 (m, 2H), 2.83-2.95 (m, 2H), 3.7-3.8 (m, 1H), 4.28 (dd, 1H), 4.60 (dd, 2H), 4.68-4.76 (m, 1H), 5.04 (dd, 1H), 5.48 (d, 1H), 6.95 (d, 2H), 7.05-7.17 (m, 4H), 7.19-7.28 (m, 5H), 7.30-7.40 (m, 6H), 7.88 (d, 1H), 8.55 (d, 1H).

Example 5

N-{[4-((2R,3R)-1-(4-fluorophenyl)-3-{[2-(4-fluorophenyl)-2-hydroxyethyl]thiol-4-oxoazetidin-2-yl)phenoxy]acetyl}-L-tryptophyl-D-phenylalanine N-{[4-((2R,3R)-1-(4-Fluorophenyl)-3-{[2-(4-fluorophenyl)-2-hydroxyethyl]thio}-4-oxoazetidin-2-yl)phenoxy]acetyl}-L-tryptophan (0.015 g, 0.022 mmol) was dissolved in CH₂Cl₂ (2 ml). H-D-Phe-OTBU hydrochloride (0.007 g, 0.027 mmol) and N-Methylmorpholine (0.007 g, 0.067 mmol) were added. After 10 minutes TBTU (0.009 g, 0.029 mmol) was added. The reaction mixture was stirred at room temperature for 2 h. The mixture was then passed through a short pad of silica gel and eluted with EtOAc/CH₂Cl₂ 25/75. The pure fractions were collected and concentrated. The resulting tert-butyl ester was hydrolysed by the addition of formic acid (0.5 ml) followed by stirring at room temperature overnight. The resulting product was concentrated and dissolved in 2 ml of MeOH. Et3N (0.1 ml) was added in order to hydrolyze the formulated product. The mixture was allowed to stir overnight. The solvent was evaporated and the residue was purified by preparative HPLC using a gradient of 20-60% CH₃CN in 0.1 M NH₄OAc buffer as mobile phase. Freeze-drying afforded the title product (0.004 g, 22%) as a colourless solid. M/z: 817.3 (M−1). ¹H NMR (CD₃CN, 400 MHz) δ 2.82-3.20 (m, 6H), 4.07-4.15 (m, 1H), 4.29-4.39 (m, 2H), 4.54-4.89 (m, 4H), 6.74-7.53 (m, 22H), 9.14-9.20 (m, 1H).

Example 6

N-((2R)-2-{[(4-{(2R,3R)-3-[(2-hydrozy-2-phenylethyl)thio]-4-oxo-1-phenylazetidin-2-yl}phenoxy)acetyl]amino}-2-phenylacetyl)glycine

[4-((2R,3R)-3-{[(5,5-Dimethyl-2-phenyl-1,3-dioxan-2-yl)methyl]thiol]-4-oxo-1-phenylazetidin-2-yl)phenoxy]acetic acid (0.050 g, 0.094 mmol) was dissolved in CH₂Cl₂ (5 ml). tert-Butyl N-[(2R)-2-amino-2-phenylacetyl]glycinate (0.030 g, 0.112 mmol) and N-methylmorpholine (0.028 g, 0.281 mmol) were added. After 5 minutes TBTU (0.039 g, 0.122 mmol) was added. After 1 h, HPLC showed a full conversion to the corresponding tert-butylester. The reaction mixture was purified by chromatography on silica gel and eluted with EtOAc/CH₂Cl₂ (25/75). Pure fractions were collected and concentrated. The residue was dissolved in 3 ml CH₂Cl₂ and 1 ml trifluoroacetic acid was added. The reaction mixture was allowed to stir at room temperature for 2 h after which the resulting acid was concentrated in vacuo. The remaining TFA was removed through co-evaporation with toluene (2 ml). The acid was dissolved in 3 ml of MeOH and sodiumborohydride (10 mg, 0.264 mmol) was added. After 5 minutes, HPLC showed a full conversion to the corresponding alcohol. The reaction was quenched by the addition of 1 ml of 0.1M NH₄OAc buffer followed by concentration of the mixture. Purification by preparative HPLC of the residue using a gradient of 20-60% CH₃CN in 0.1 M NH₄OAc buffer as mobile phase and lyophilisation afforded the title product (0.032 g, 54%) as a colourless solid. M/z: 638.5 (M−1). ¹H NMR [(CD₃)₂SO), 400 MHz] δ 2.90-2.94 (m, 2H), 3.45-3.65 (m, 2H), 4.25-4.27 (m, 1H), 4.59 (d, 1H), 4.64 (d, 1H), 4.68-4.75 (m, 1H), 5.02-5.05 (m, 1H), 5.57 (d, 1H), 6.94-7.41 (m, 19H), 8.28 (s, br, 1H), 8.55 (d, 1H).

Example 7

N-[(4-{(2R,3R)-3-[(2-hydroxy-2-phenylethyl)thio]-4-oxo-1-phenylazetidin-2-yl}phenoxy)acetyl]glycyl-D-phenylalanine N-[(4-{(2R,3R)-4-Oxo-3-[(2-oxo-2-phenylethyl)thio]-1-phenylazetidin-2-yl}phenoxy)acetyl]glycine was dissolved in CH₂Cl₂ (3 ml). (R)-Phenylalanine tert-butyl ester hydrochloride (0.012 g, 0.045 mmol) and N-methylmorpholine (0.011 g, 0.113 mmol) were added. After 5 minutes TBTU (0.016 g, 0.049 mmol) was added. After 1 h, full conversion to the corresponding tert-butyl ester was obtained. The reaction mixture purified by chromatography on silica gel and eluted with EtOAc/CH₂Cl₂ 25/75. Pure fractions were collected and concentrated. The residue was dissolved in 3 ml CH₂Cl₂ and 0.5 ml trifluoroacetic acid and the reaction was allowed to stir at room temperature overnight. The resulting acid was concentrated and dissolved in 3 ml of MeOH. Sodiumborohydride (0.010 g, 0.264 mmol) was added. Full conversion to the corresponding alcohol was obtained after 5 minutes. The reaction was quenched by the addition of 1 ml of 0.1M NH₄OAc buffer. Concentration followed by preparative HPLC using a gradient of 20-60% CH₃CN in 0.1M NH₄OAc buffer as mobile phase afforded the title product (0.021 g, 84%) as a colourless solid after freeze-drying. M/z: 652.3 (M−1). ¹H NMR [(CD₃)₂SO), 400 MHz] δ 2.85-3.05 (m, 4H), 3.62-3.80 (m, 2H), 4.18-4.35 (m, 2H), 4.48 (d, 1H), 4.51 (d, 1H), 4.68-4.78 (m, 1H), 4.99-5.03 (m, 1H), 6.93-7.35 (m, 19H), 7.65-7.80 (m, 1H), 8.23-8.29 (m, 1H).

Example 8

N-[(2R)-2-({[4-((2R,3R)-1-(4-fluorophenyl)-3-{[2-(4-fluorophenyl)-2-hydroxyethyl]thio}-4-oxoazetidin-2-yl)phenoxy]acetyl}amino)-2-phenylacetyl]-L-alanine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.040 g, 0.065 mmol) was dissolved in $CH_2Cl_2$ (5 ml). tert-Butyl L-alaninate hydrochloride (0.014 g, 0.078 mmol) and N-methyl-morphiline (0.020 g, 0.195 mmol) were added. After 5 minutes TBTU (0.027 g, 0.084 mmol) was added. The reaction was allowed to stir for 1 h after which the resulting tert-butyl ester was purified by chromatography on silica gel and eluted with $EtOAc/CH_2Cl_2$ 25/75. Pure fractions were concentrated and dissolved in $CH_2Cl_2$ (4 ml) and trifluoroacetic acid (0.5 ml). After 1.5 h at room temperature, full conversion to the corresponding acid was obtained. The reaction mixture was concentrated and the residue of TFA was removed by co-evaporation with toluene (3 ml). The crude acid was dissolved in MeOH (3 ml) and $NaBH_4$-(0.010 g, 0.260 mmol) was added. Full conversion to the corresponding alcohol was obtained after 5 minutes. The reaction was quenched by the addition of 0.1M $NH_4OAc$ buffer (1 ml). The mixture was concentrated and the residue was purified by preparative HPLC using a gradient of 20-50% $CH_3CN$ in 0.1M $NH_4OAc$ buffer as mobile phase. Freeze-drying afforded the title compound (0.020 g, 45%) as a colourless solid. M/z: 688.4 (M−1). $^1$H NMR [$(CD_3)_2SO$], 400 MH] δ 2.30-2.35 (m, 3H), 2.86-2.94 (m, 2H), 3.15-3.31 (m, 1H), 4.26-4.28 (m, 1H), 4.59 (d, 1H), 4.64 (d, 1H), 4.70-4.76 (m, 1H), 5.04-5.07 (m, 1H), 5.46 (d, 1H), 6.94-7.36 (m, 17H), 8.43-8.55 (m, 2H).

Example 9

N-[(2R)-2-({[4-((2R,3R)-1-(4-fluorophenyl)-3-{[2-(4-fluorophenyl)-2-hydroxyethyl]thio}-4-oxoazetidin-2-yl)phenoxy]acetyl}amino)-2-phenylacetyl]-D-alanine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.040 g, 0.065 mmol) was dissolved in $CH_2Cl_2$ (5 ml). tert-Butyl D-alaninate hydrochloride (0.014 g, 0.078 mmol) and N-methyl-morphiline (0.020 g, 0.195 mmol) were added. After 5 minutes TBTU (0.027 g, 0.084 mmol) was added. The reaction was allowed to stir overnight and the resulting tert-butyl ester was purified on silica gel and eluted with $EtOAc/CH_2Cl_2$ (25/75). The pure fractions were concentrated. The residue was dissolved in $CH_2Cl_2$ (4 ml) and trifluoroacetic acid (0.5 ml). After 1.5 h at room temperature, full conversion to the corresponding acid was obtained. The reaction mixture was concentrated and the remaining TFA was removed through co-evaporation with toluene (3 ml). The crude acid was dissolved in MeOH (3 ml) and $NaBH_4$ (0.010 g, 0.260 mmol) was added. Full conversion to the corresponding alcohol was obtained after 5 minutes. The reaction was quenched by the addition of 0.1M $NH_4OAc$ buffer (1 ml). The mixture was concentrated and the residue was purified by preparative HPLC using a gradient of 20-50% $CH_3CN$ in 0.1M $NH_4OAc$ buffer as mobile phase. Freeze-drying gave the title compound (0.024 g, 54%) as a colourless solid. M/z: 688.6 (M−1). $^1$H NMR [$(CD_3)_2SO$], 400 MHz] δ 1.10-1.24 (m, 3H), 2.89-2.94 (m, 2H), 3.99-4.08 (m, 1H), 4.26-4.30 (m, 1H), 4.60 (d, 1H), 4.64 (d, 1H), 4.70-4.78 (m, 1H), 5.02-5.08 (m, 1H), 5.53-5.56 (d, 1H), 6.94-7.40 (m, 17H), 8.39-8.59 (m, 2H).

Example 10

(2R)-{[(2R)-2-({[4-((2R,3R)-1-(4-fluorophenyl)-3-{[2-(4-fluorophenyl)-2-hydroxyethyl]thio}-4-oxoazetidin-2-yl)phenoxy]acetyl}amino)-2-phenylacetyl]amino}(phenyl)acetic acid (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.040 g, 0.065 mmol) was dissolved in $CH_2Cl_2$ (5 ml) and tert-butyl (2R)-amino(phenyl)acetate (0.016 g, 0.078 mmol) and N-methyl-morphiline (0.020 g, 0.195 mmol) were added. After 5 minutes TBTU (0.027 g, 0.084 mmol) was added. The reaction was allowed to stir at room temperature for 3 h after which the resulting tert-butyl ester was purified on silica gel and eluted with $EtOAc/CH_2Cl_2$ 25/75. Pure fractions were concentrated. The residue was dissolved in $CH_2Cl_2$ (3 ml) and TFA (0.5 ml). The reaction mixture was allowed to stir overnight at room temperature. The resulting acid was concentrated and the remaining trace of TFA was removed by co-evaporation with toluene (3 ml). The acid was dissolved in MeOH (3 ml) and NaBH (0.010 g, 0.260 mmol) was added. After 5 minutes, full conversion to the corresponding alcohol was obtained. The reaction was quenched by the addition of 1 ml of 0.1M $NH_4OAc$ buffer. Concentration followed by purification on preparative HPLC using a gradient of 20-50% $CH_3CN$ in 0.1M $NH_4OAc$ buffer as mobile phase and freeze-drying of the pure fractions afforded the title compound (0.034 g, 70%) as a colourless solid. M/z: 750.4 (M−1). $^1$H NMR [$(CD_3)_2SO$], 400 MHz] δ 2.88-2.94 (m, 2H), 4.23-4.29 (m, 1H), 4.56-4.65 (m, 2H), 4.70-4.78 (m, 1H), 4.91-5.06 (m, 2H), 5.65-5.75 (m, 1H), 6.93-7.42 (m, 22H), 8.54-8.69 (m, 2H).

Example 11

(2S)-{[(2R)-2-({[4-((2R,3R)-1-(4-fluorophenyl)-3-{[2-(4-fluorophenyl)-2-hydroxyethyl]thio}-4-oxoazetidin-2-yl)phenoxy]acetyl}amino)-2-phenylacetyl]amino}(phenyl)acetic acid (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.040 g, 0.065 mmol) was dissolved in $CH_2Cl_2$ (5 ml). tert-Butyl (2S)-amino(phenyl)acetate (0.016 g, 0.078 mmol) and N-methyl-morphiline (0.020 g, 0.195 mmol) were added. After 5 minutes, TBTU (0.027 g, 0.084 mmol) was added. The reaction mixture was stirred at room temperature for 3 h. The resulting tert-butyl ester was purified on silica gel and eluted with $EtOAc/CH_2Cl_2$ (25/75). The pure fractions were concentrated. The residue was dissolved in $CH_2Cl_2$ (3 ml) and TFA (0.5 ml). The reaction mixture was stirred overnight at room temperature. The resulting acid was concentrated and the remaining trace of TFA was removed by co-evaporation with toluene (3 ml). The acid was dissolved in MeOH (3 ml) and NaBH (0.010 g, 0.260 mmol) was added. After 5 minutes, full conversion to the corresponding alcohol was obtained. The reaction was quenched by the addition of 1 ml of 0.1M $NH_4OAc$ buffer. Concentration followed by purification on preparative HPLC using a gradient of 20-50% $CH_3CN$ in 0.1M $NH_4OAc$ buffer as mobile phase and freeze-drying of the pure fractions afforded the title compound (0.037 g, 76%) as a colourless solid. M/z: 750.6 (M–1). $^1$H NMR [(CD$_3$)$_2$SO), 400 MHz] δ 2.87-2.94 (m, 2H), 4.25-4.28 (m, 1H), 4.58-4.78 (m, 3H), 5.01-5.07 (m, 2H), 5.65-5.74 (m, 1H), 6.94-7.39 (m, 22H), 8.53-8.72 (m, 2H).

Example 12

N-[(2R)-2-({[4-((2R,3R)-1-(4-fluorophenyl)-3-{[2-(4-fluorophenyl)-2-hydroxyethylthio}-4-oxoazetidin-2-yl)phenoxy]acetyl}amino)-2-phenylacetyl]-D-serine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.040 g, 0.065 mmol), tert-butyl O-(tert-butyl)-D-serinate hydrochloride (0.020 g, 0.078 mmol) and N-methyl-morpholine (0.020 g, 0.195 mmol) were dissolved in CH$_2$Cl$_2$ (5 ml) at room temperature. After 5 minutes, TBTU (0.027 g, 0.084 mmol) was added. After 1 h, full conversion to the corresponding tert-butyl ester was obtained. The reaction mixture was purified on silica gel and eluted with EtOAc/CH$_2$Cl$_2$ (25/75). Pure fractions were collected and concentrated. The residue was dissolved in 3 ml CH$_2$Cl$_2$ and 1 ml TFA. The reaction mixture was stirred for 1.5 h and concentrated. The remaining trace of TFA was azeotropically removed by co-evaporation with toluene (3 ml). The crude acid was dissolved in MeOH (3 ml) and NaBH$_4$ (0.010 g, 0.260 mmol) was added. Full conversion to the corresponding alcohol was obtained after 5 minutes. The reaction was quenched by the addition of 0.1M NH$_4$OAc buffer (2 ml). Purification on preparative HPLC using a gradient of 20-50% CH$_3$CN in 0.1M NH$_4$OAc buffer as mobile phase followed by freeze-drying of the pure fractions afforded the title compound (0.032 g, 71%) as a colourless solid. M/z: 704.7 (M–1). $^1$H NMR [(CD$_3$)$_2$SO), 400 MHz] δ 2.88-2.94 (m, 2H), 3.42-3.46 (m, 1H), 3.58-3.61 (m, 1H), 3.85-3.90 (m, 1), 4.26-4.29 (m, 1H), 4.59 (d, 1H), 4.64 (d, 1H), 4.70-4.77 (m, 1H), 5.04-5.07 (m, 1H), 5.57-5.65 (m, 1H), 6.95-7.41 (m, 17H), 8.08-8.20 (m, 1H), 8.53-8.56 (m, 1H).

Example 13

N-[(2R)-2-({[4-((2R,3R)-1-(4-fluorophenyl)-3-{[2-(4-fluorophenyl)-2-hydroxyethy]thio}-4-oxoazetidin-2-yl)phenoxy]acetyl}amino)-2-phenylacetyl]-L-threonine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.030 g, 0.049 mmol), tert-butyl O-(tert-butyl)-L-threoninate (0.014 g, 0.058 mmol) and N-methyl-morpholine (0.015 g, 0.146 mmol) were dissolved in CH$_2$Cl$_2$ (4 ml). After 5 minutes, TBTU (0.020 g, 0.063 mmol) was added. Full conversion to the corresponding tert-butyl ester was obtained after 1 h. The reaction mixture was purified on silica gel and eluted with EtOAc/CH$_2$Cl$_2$ (25/75). Pure fractions were collected and concentrated. The residue was dissolved in 3 ml CH$_2$Cl$_2$ and 1 ml TFA and the mixture was stirred for 1.5 h. The resulting acid was concentrated. The remaining trace of TFA was azeotropically removed by co-evaporation with toluene (3 ml). The crude acid was dissolved in MeOH (3 ml) and NaBH$_4$ (0.007 g, 0.195 mmol) was added. Full conversion to the corresponding alcohol was obtained after 5 minutes. The reaction was quenched by the addition of 0.1M NH$_4$OAc buffer (2 ml). Purification by preparative HPLC using a gradient of 20-50% CH$_3$CN in 0.1M NH$_4$OAc buffer as eluent followed by freeze-drying of the pure fractions afforded the title compound (0.025 g, 71%) as a colourless solid. M/z: 721.1. $^1$H NMR [(CD$_3$)$_2$SO), 400 M/z] δ 0.69 (d, 3H), 2.88-2.93 (m, 2H), 3.79-3.85 (m, 1H), 3.96-4.01 (m, 1H), 4.27-4.30 (m, 1H), 4.60 (d, 1H), 4.64 (d, 1H), 4.71-4.79 (m, 1H), 5.02-5.08 (m, 1H), 5.65-5.69 (m, 1H), 6.95-7.42 (m, 17H), 8.01-8.09 (m, 1H), 8.51-8.59 (m, 1H).

Example 14

N$^2$-[(2R)-2-({[4-((2R,3R)-1-(4-fluorophenyl)-3-{[2-(4-fluorophenyl)-2-hydroxyethy]thio}-4-oxoazetidin-2-yl)phenoxy]acetyl}amino)-2-phenylacetyl]-L-asparagine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.030 g, 0.049 mmol), tert-butyl L-asparaginate hydrochloride (0.013 g, 0.058 mmol) and N-methyl-morpholine (0.015 g, 0.146 mmol) were dissolved in CH$_2$Cl$_2$ (4 ml). TBTU (0.020 g, 0.063 mmol) was added after 5 minutes. Full conversion to the corresponding tert-butyl ester was obtained after 1 h. The reaction mixture was purified on silica gel and eluted with EtOAc. The pure fractions were collected and concentrated. The residue was dissolved in 3 ml CH$_2$Cl$_2$ and 1 ml TFA and the mixture was stirred for 0.5 h. The resulting acid was concentrated. The remaining trace of TFA was azeotropically removed by co-evaporation with toluene (3 ml). The crude acid was dissolved MeOH (3 ml) and NaBH$_4$ (0.007 g, 0.195 mmol) was added. Full conversion to the corresponding alcohol was obtained after 5 minutes. The reaction was quenched by the addition of 0.1M NH$_4$OAc buffer (2 ml). Purification by preparative HPLC using a gradient of 2040% CH$_3$CN in 0.1M NH$_4$OAc buffer as eluent followed by freeze-drying of the pure fractions afforded the title compound (0.024 g, 67%) as a colourless solid. M/z: 731.6 (M–1).
$^1$H NMR [(CD$_3$)$_2$SO), 400 MHz)] δ 2.16-2.23 (m, 1H), 2.32-2.42 (m, 1H), 2.87-2.95 (m, 2H), 4.20-4.30 (m, 2H), 4.59-4.78 (m, 3H), 5.03-5.07 (m, 1H), 5.54-5.59 (m, 1H), 6.68-6.73 (m, 1H), 6.94-7.38 (m, 17H), 7.78-7.83 (m, 1H), 8.22-8.37 (m, 1H), 8.50-8.58 (m, 1H).

Example 15

N-[(2R)-2-({[4-((2R,3R)-1-(4-fluorophenyl)-3-{[2-(4-fluorophenyl)-2-hydroxyethyl]thiol}-4-oxoazetidin-2-yl)phenoxy]acetyl}amino)-2-phenylacetyl]-L-aspartic acid (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.020 g, 0.032 mmol), di-tert-butyl L-aspartate hydrochloride (0.011 g, 0.039 mmol) and N-methyl-morpholine (0.010 g, 0.097 mmol) were dissolved in CH$_2$Cl$_2$ (3 ml). After 5 minutes, TBTU (0.014 g, 0.042 mmol) was added. Full conversion to the corresponding tert-butyl ester was obtained after 1 h. The reaction mixture was purified on silica gel and eluted with EtOAc/CH$_2$Cl$_2$ (25/75). The pure fractions were collected and concentrated. The residue was dissolved in 3 ml of CH$_2$Cl$_2$ and 1 ml of TFA. The reaction mixture was stirred for 2 h and the resulting acid was concentrated. The remaining trace of TFA was azeotropically removed by co-evaporation with toluene (3 ml). The crude acid was dissolved in MeOH (3 ml) and NaBH$_4$ (0.005 g, 0.130 mmol) was added. Full conversion to the corresponding alcohol was obtained after 5 minutes. The reaction was quenched by the addition of 0.1M NH$_4$OAc buffer (2 ml).

Purification by preparative HPLC using a gradient of 10-40% CH₃CN in 0.1M NH₄OAc buffer as eluent followed by freeze-drying of the pure fractions afforded the title compound (0.018 g, 76%) as a colourless solid. M/z: 715.7 (M−18). ¹H NMR [(CD₃)₂SO), 400 MHz] δ2.00-2.08 (m, 1H), 2.31-2.50 (m, 1H), 2.88-2.94 (m, 2H), 4.18-4.22 (m, 1H), 4.27-4.30 (m, 1H), 4.60-4.78 (m, 3H), 5.03-5.08 (m, 1H), 5.55-5.65 (m, 1H), 6.94-7.40 (m, 17H), 8.22-8.39 (m, 1H), 8.50-8.59 (m, 1H).

Example 16

N-[(2R)-2-({[4-((2R,3R)-(4-fluorophenyl)-3-{[2-(4-fluorophenyl)-2-hydroxyethyl]thio}-4-oxoazetidin-2-yl)phenoxy]acetyl}amino)-2-phenylacetyl]-D-valine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.010 g, 0.016 mmol), tert-butyl D-valinate hydrochloride (0.004 g, 0.020 mmol) and N-methyl-morpholine (0.005 g, 0.049 mmol) were dissolved in CH₂Cl₂ (3 ml). After 5 minutes, TBTU (0.007 g, 0.021 mmol) was added. Full conversion to the corresponding tert-butyl ester was obtained after 1 h. The reaction mixture was purified on silica gel and eluted with EtOAc/CH₂Cl₂ (25/75). The pure fractions were collected and concentrated. The residue was dissolved in 3 ml CH₂Cl₂ and 0.5 ml TFA. The reaction mixture was stirred for 1.5 h and concentrated. The remaining trace of TFA was azeotropically removed by co-evaporation with toluene (3 ml). The crude acid was dissolved in MeOH (2 ml) and NaBH₄ (0.002 g, 0.065 mmol) was added. Full conversion to the corresponding alcohol was obtained after 5 minutes. The reaction was quenched by the addition of 0.1M NH₄OAc buffer (2 ml). Purification by preparative HPLC using a gradient of 20-50% CH₃CN in 0.1M NH₄OAc buffer as mobile phase followed by freeze-drying of the pure fractions afforded the title compound (0.004 g, 34%) as a colourless solid. M/z: 716.6 (M−1). ¹H NMR [(CD₃)₂SO), 400 MH] δ0.81-0.85 (m, 6H), 1.98-2.09 (m, 1H), 2.88-2.93 (m, 2H), 3.92-3.98 (m, 1H), 4.22-4.30 (m, 1H), 4.60 (d, 1H), 4.64 (d, 1H), 4.70-4.78 (m, 1H), 5.02-5.07 (m, 1H), 5.62 (d, 1H), 6.94-7.40 (m, 17H), 8.18-8.22 (m, 1H), 8.52 (d, 1H).

Example 17

N-[(2R)-2-({[4-((2R,3R)-1-(4-fluorophenyl)-3-{[2-(4-fluorophenyl)-2-hydroxyethyl]thio}-4-oxoazetidin-2-yl)phenoxy]acetyl}amino)-2-phenylacetyl]-L-valine (2R)-({[4-((2R,3R)-1-(4-Fluorophenyl)-3-{[2-(4-fluorophenyl)-2-oxoethyl]thio}-4-oxoazetidin-2-yl)phenoxy]acetyl}amino)(phenyl)acetic acid (0.020 g, 0.032 mmol), tert-butyl L-valinate hydrochloride (0.008 g, 0.039 mmol) and N-methyl-morpholine (0.010 g, 0.097 mmol) were dissolved in CH₂Cl₂ (4 ml). After 5 minutes, TBTU (0.014 g, 0.042 mmol) was added. Full conversion to the corresponding tert-butyl ester was obtained after 1 h. The reaction mixture was purified on silica gel and eluted with EtOAc/CH₂Cl₂ (25/75). The pure fractions were collected and concentrated. The residue was dissolved in 3 ml CH₂Cl₂ and 1 ml TFA. The reaction mixture was stirred for 1.5 h and concentrated. The remaining trace of TFA was azeotropically removed by co-evaporation with toluene (3 ml). The crude acid was dissolved in MeOH (3 ml) and NABH₄ (0.005 g, 0.130 mmol) was added. Full conversion to the corresponding alcohol was obtained after 5 minutes. The reaction was quenched by the addition of 0.1M NH₄OAc buffer (2 ml). Purification by preparative HPLC using a gradient of 20-50% CH₃CN in 0.1M NH₄OAc buffer as eluent followed by freeze-drying of the pure fractions afforded the title compound (0.011 g, 47%) as a colourless solid. M/z: 716.5 (M−1).

¹H NMR [(CD₃)₂SO), 400 MHz] δ0.60 (d, 3H), 0.68 (d, 3H), 1.95-2.05 (m, 1H), 2.88-2.94 (m, 2H), 4.00-4.08 (m, 1H), 4.27-4.30 (m, 1H), 4.61 (d, 1H), 4.64 (d, 1H), 4.70-4.78 (m, 1H), 5.02-5.09 (m, 1H), 5.64-5.75 (m, 1H), 6.94-7.44 (m, 17H), 8.39-8.45 (m, 1H), 8.50-8.58 (m, 1H).

Example 18

N-((2R)-2-{[(4-{(2R,3R)-3-[(2-hydroxy-2-phenylethyl)thio]-4-oxo-1-phenylazetidin-2-yl}phenoxy)acetyl]amino}-2-phenylacetyl)-L-serine

[4-((2R,3R)-3-{[(5,5-Dimethyl-2-phenyl-1,3-dioxan-2-yl)methyl]thio}-4-oxo-1-phenylazetidin-2-yl)phenoxy]acetic acid (0.030 g, 0.056 mmol), tert-butyl N-[(2R)-2-amino-2-phenylacetyl]-O-(tert-butyl)-L-serinate (0.024 g, 0.068 mmol) and N-methyl-morpholine (0.017 g, 0.169 mmol) were dissolved in CH₂Cl₂ (5 ml). After 5 minutes, TBTU (0.023 g, 0.073 mmol) was added. Full conversion to the corresponding tert-butyl ester was obtained after 1 h. The reaction mixture was purified on silica gel and eluted with EtOAc/CH₂Cl₂ (25/75). The pure fractions were collected and concentrated. The residue was dissolved in 3 ml CH₂Cl₂ and 1 ml TFA. The reaction mixture was stirred overnight and concentrated. The remaining trace of TFA was azeotropically removed by co-evaporation with toluene (3 ml). The crude acid was dissolved in MeOH (4 ml) and NaBH (0.009 g, 0.225 mmol) ws added. Full conversion to the corresponding alcohol was obtained after 5 minutes. The reaction was quenched by the addition of 0.1M NH₄OAc buffer (2 ml). Purification by preparative HPLC using a gradient of 20-50% CH₃CN in 0.1M NH₄OAc buffer as mobile phase followed by freeze-drying of the pure fractions afforded the title compound (0.022 g, 58%) as a colourless solid. M/z: 668.5 (M−1). ¹H NMR [(CD₃)₂SO), 400 MHz] δ2.89-2.94 (m, 2H), 3.30-3.35 (m, 1H), 3.46-3.50 (m, 1H), 3.94-4.00 (m, 1H), 4.25-4.27 (m, 1H), 4.60 (d, 1H), 4.65 (d, 1H), 4.69-4.77 (m, 1H), 5.00-5.05 (m, 1H), 5.59-5.66 (m, 1H), 6.94-7.39 (m, 19H), 8.20-8.25 (m, 1H), 8.50-8.58 (m, 1H).

Example 19

N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-alanyl-D-valine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-alanine (0.040 g, 0.072 mmol) was dissolved in CH₂Cl₂ (5 ml). tert-Butyl D-valinate hydrochloride (0.018 g, 0.087 mmol), N-methylmorpholine (0.022 g, 0.216 mmol) and TBTU (0.030 g, 0.094 mmol) were added. The tert-butyl ester was obtained after 1.5 h. The reaction mixture was purified on silica gel and eluted with CH₂Cl₂/EtOAc (75/25). The pure fractions were collected and concentrated. The residue was dissolved in CH₂Cl₂ (4 ml) and TFA (1 ml). The reaction mixture was stirred for 3 h and concentrated. The crude acid was dissolved in MeOH (4 ml) and NaBH (0.011 g, 0.289 mmol) was added. Full conversion to the corresponding alcohol was obtained after 5 minutes. The reaction was quenched by the addition of 0.1M NH₄OAc buffer (1 ml). The reaction mixture was concentrated and the residue was purified by preparative HPLC using an eluent of 20-50% CH₃CN in 0.1M NH₄OAc buffer. This gave the title compound (0.039 g, 82%) as a colourless solid. M/z: 654.5 (M−1). ¹H NMR [(CD₃)₂SO), 400 MHz] δ0.79 (d, 6H), 1.21 (d, 3H), 1.96-2.05 (m, 1H), 2.85-2.95 (m, 2H), 3.91-3.97 (m, 1H), 4.22-4.29 (m, 1H), 4.35-4.42 (m, 1H), 4.48 (d, 1H), 4.53 (d, 1H), 4.70-4.78 (m, 1H), 5.02-5.04 (m, 1H), 6.94-7.36 (m, 12H), 7.70-7.77 (m, 1H), 8.15 (d, 1H).

Example 20

N-{[4-((2R,3R)-1-(4-fluorophenyl)-3-{[2-(4-fluorophenyl)-2-hydroxyethyl]thiol-4-oxoazetidin-2-yl) phenoxy]acetyl}-D-alanyl-D-alanine N-{[4-((2R,3R)-1-(4-Fluorophenyl)-3-{[2-(4-fluorophenyl)-2-oxoethyl]thio}-4-oxoazetidin-2-yl)phenoxy]acetyl]-D-alanine (0.040 g, 0.072 mmol) was dissolved in CH₂Cl₂ (5 ml). tert-Butyl D-alaninate hydrochloride (0.016 g, 0.087 mmol), N-methylmorpholine (0.022 g, 0.216 mmol) and TBTU (0.030 g, 0.094 mmol) were added. Full conversion to the tert-butyl-ester was obtained after 1.5 h. The reaction mixture was purified on silica gel and eluted with EtOAc/CH₂Cl₂ (25/75). The pure fractions were collected and concentrated. The residue was dissolved in CH₂Cl₂ (3 ml) and TFA (1 ml). Full conversion to the acid was obtained after 2 h at room temperature. The reaction mixture was concentrated and the remaining trace of TFA was azeotropically removed by co-evaporation with toluene (3 Ml). The crude acid was dissolved in MeOH (3 ml) and NaBH (0.011 g, 0.289 mmol) was added. Full conversion to the corresponding alcohol was obtained after 5 minutes. The reaction was quenched by the addition of 0.1M NH₁₄OAc buffer (1 ml). The reaction mixture was concentrated and the residue purified by preparative HPLC using a gradient of 20-50% CH₃CN in 0.1M NH₄OAc buffer as mobile phase. Freeze-drying of the pure fractions gave the title compound (0.039 g, 86%) as a colourless solid. M/z: 626.4 (−1). ¹H NMR [(CD₃)₂SO), 400 MHz] δ 1.17-1.22 (m, 6H), 2.82-2.96 (m, 2H), 3.90-3.98 (m, 1H), 4.25-4.35 (m, 2H), 4.48-4.54 (m, 2H), 4.70-4.78 (m, 1H), 5.02-5.06 (m, 1H), 6.94-7.37 (m, 12H), 7.85-7.92 (m, 1H), 8.16 (d, 1H).

Example 21

N-{[4-((2R,3R)-1-(4-fluorophenyl)-3-{[2-(4-fluorophenyl)-2-hydroxyethyl]thio}-4-oxoazetidin-2-yl) phenoxy]acetyl}-D-alanyl-D-lysine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-alanine (0.040 g, 0.072 mmol) was dissolved in CH₂Cl₂ (5 ml). tert-Butyl N⁶-(tert-butoxycarbonyl)-D-lysinate hydrochloride (0.029 g, 0.087 mmol), N-methylmorpholine (0.022 g, 0.216 mmol) and TBTU (0.030 g, 0.094 mmol) were added. After 1.5 h full conversion to the ester was obtained. The reaction mixture was purified on silica gel and eluted with EtOAc/CH₂Cl₂ (25/75). The pure fractions were collected and concentrated. The residue was dissolved in CH₂Cl₂ (3 ml) and TFA (1 ml) and stirred overnight and the corresponding acid was formed. The reaction mixture was concentrated and the remaining trace of TFA was azeotropically removed by co-evaporation with toluene (3 ml). The crude acid was dissolved in MeOH (3 ml) and NaBH₄ (0.011 g, 0.288 mmol) was added. The reduction was completed after 5 minutes. The reaction was quenched by the addition of 0.1M NH₄OAc buffer (1 ml). The mixture was concentrated and the residue purified by preparative HPLC using a gradient of 10-50% CH₃CN in 0.1M NH₄OAc buffer as eluent. Freeze-drying of the pure fractions afforded the title compound (0.039 g, 79%) as a colourless solid. M/z: 685.1. ¹H NMR [(CD₃)₂SO), 400 M/z] δ 1.21 (d, 3H), 1.22-1.69 (m, 6H), 2.62-2.70 (m, 2H), 2.82-2.93 (m, 2H), 3.78-3.84 (m, 1H), 4.22-4.33 (m, 2H), 4.48 (d, 1H), 4.52 (d, 1H), 4.70-4.78 (m, 1H), 5.01-5.06 (m, 1H), 6.95-7.37 (m, 12H), 7.56-7.63 (m, 1H), 8.27 (d, 1H).

Example 22

N-{[4-((2R,3R)-1-(4-fluorophenyl)-3-{[2-(4-fluorophenyl)-2-hydroxyethyl]thiol-4-oxoazetidin-2-yl) phenoxy]acetyl}-D-valyl-D-serine N-{[4-((2R,3R)-1-(4-fluorophenyl)-3-{[2-(4-fluorophenyl)-2-oxoethyl]thio}-4-oxoazetidin-2-yl)phenoxy]acetyl}-D-valine (11 mg, 18.9 μmol) was dissolved in DCM (2 ml). tert-Butyl O-(tert-butyl)-D-serinate hydrochloride (6.3 mg, 24.8 μmol) and N-methylmorpholine (10 μl, 91 μmol) were added. After 5 minutes, TBTU (8.2 mg, 25.5/mol) was added and the reaction mixture, a white suspension, was stirred overnight. The formation of the ester was confirmed. M/z: 780.5 (M−H). The solvent was removed under reduced pressure. The residue was dissolved in formic acid (1 ml) and stirred at 50° C. for 5 h and at ambient temperature overnight. LC-MS analysis showed the formation of the formiate adduct of the product. M/z: 698.2 (M+H) and 696.2 (M−H). The formic acid was removed under reduced pressure, toluene (3×1 ml) was used to assist this removal. The yellowish oily residue was dissolved in methanol (1 ml) and triethylamine (150 μl, 0.12 mmol) was added. The reaction mixture was stirred for 1 h. The formiate was hydrolyzed; M/z: 670.1 (M+1) and 668.0 (M−1). Sodium borohydride (8.4 mg, 0.22 mmol) was added to the methanol solution. The mixture was stirred for 5 minutes. Ammonium acetate (7 mg) was added and the solvent was removed under reduced pressure. The residue was purified with preparative HPLC on a C8 column. A gradient from 20 to 50% MeCN in 0.1M ammonium acetate buffer was used as eluent. After freeze-drying, the title compound was obtained as a white solid (3.8 mg, 30%). H-NMR (400 MHz, DMS-d₆): 0.80 (m, 6H), 1.95-2.05 (m, 1H), 2.87-2.93 (m, 2H), 3.46-3.60 (m, 2H), 3.86 (brs, 1H), 4.19-4.32 (m, 2H), 4.59 (br, 2H), 4.69-4.77 (m, 1H), 5.05 (m, 1H), 6.96 (d, 2H), 7.06-7.18 (m, 4H), 7.20-7.26 (m, 2H), 7.30-7.39 (m, 4H), 7.70-7.77 (brs, 1H), 7.96-8.01 (d, 1H). M/z: 670.1(M−H).

Example 23

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-D-valine N-{[4-((2R,3R)-1-(4-fluorophenyl)-3-{[2-(4-fluorophenyl)-2-oxoethyl]thiol-4-oxoazetidin-2-yl)phenoxy] acetyl}glycyl-D-valine (0.022 g, 0.034 mmol) was dissolved in methanol (2 ml). NaBH₄ (0.0025 g, 0.066 mmol) was added and when the reaction was complete according to LC-MS a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.015 g (68%) of the title product was obtained. NMR (400 MHz, CD₃COOD) 0.90 (d, 31), 0.93 (d, 3H), 2.10-2.20 (m, 1H), 2.90-3.06 (m, 2H), 3.99 (s, 2H), 4.03 (d, 0.5H), 4.05 (d, 0.5H), 4.27-4.34 (m, 1H), 4.60 (s, 2H), 4.79-4.84 (m, 1H), 4.89 (d, 0.5H), 4.91 (d, 0.5H), 6.95-7.03 (m, 4H), 7.06 (d, 2H), 7.25-7.30 (m, 2H); 7.30-7.37 (m, 4H).

Example 24

(2R)-cyclohexyl[(N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl)amino]acetic acid (2R)-cyclohexyl[(N-([4-((2R,3R)-1-(4-fluorophenyl)-3-{[2-(4-fluorophenyl)-2-oxoethyl]thio)-4-oxoazetidin-2-yl)phenoxy]acetyl}glycyl)amino]acetic acid (0.0085 g, 0.013 mmol) was dissolved in methanol (2 ml). NABH$_4$ (0.006 g, 0.159 mmol) was added and when the reaction was complete according to LC-MS a few drops of acetic acid was added. The solvent was removed under reduced pressure and the residue was purified by preparative HPLC on a Kromasil C8-column using a stepwise gradient of 35%, 40% then 50% MeCN in 0.1M ammonium acetate buffer as eluent. After freeze-drying, 0.007 g (82%) of the title product was obtained. NMR (500 MHz, CD$_3$COOD) 1.05-1.33 (m, 5H), 1.60-1.87 (m, 6H), 2.91-3.07 (m, 2H), 3.94-4.06 (m, 3H), 4.32 (d, 1H), 4.60 (s, 2H), 4.79-4.86 (m, 1H), 4.90 (d, 0.5H), 4.92 (d, 0.5H), 6.96-7.03 (m, 4H), 7.03-7.08 (brd, 2H), 7.25-7.31 (m, 2H), 7.31-7.38 (m, 4H)

Example 25

N-{[4-((2R,3R)-1-(4-fluorophenyl)-3-{[2-(4-fluorophenyl)-2-hydroxyethyl]thiol-4-oxoazetidin-2-yl)phenoxy]acetyl}glycyl-3-(trimethylsilyl)alanine Ethyl 3-(trimethylsilyl)alaninate (20 mg, 0.106 mmol) was dissolved in 1.5 ml Et$_3$N, 0.2 ml MeOH and 0.2 ml H$_2$O and stirred for 5 days. The solvent was evaporated under reduced pressure at 40° C. Et$_3$N, 1 ml, was added and evaporated.

N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (20 mg, 0.037 mmol) was dissolved in 1.5 ml dry DMF. N-Methylmorpholine (0.010 ml, 0.109 mmol) and TBTU (15 mg, 0.047 mmol) were added and the mixture was stirred for 1.5 h. The Et$_3$N-salt of the above hydrolyzed amino acid was added and the mixture was stirred for 3 h. A few drops of water were added and the mixture was stirred for 15 min. MeOH (2 ml) and NaBH$_4$ (ca 15 mg) were added. After 15 min ca 20 mg NH$_4$Ac was added. The mixture was left overnight and was purified using preparative HPLC on a C8 column. A gradient from 20-50% MeCN in 0.1M ammonium acetate was used as mobile phase. A pure product fraction was collected and lyophilized. Mass: 14.5 mg. The solid was placed in the vacuum oven at 40° C. for 5 h. M/z: 684 (M−1). NMR (400 M/z, DMSO-d6): 8.23 (t, 1H), 7.88-7.98 (m, 1H), 7.30-7.38 (m, 4H), 7.20-7.25 (m, 2H), 7.05-7.18 (m, 4H), 6.98 (d, 2H), 5.02-5.07 (m, 1H), 4.67-4.76 (m, 1H), 4.51 (s, 2H), 4.24-4.33 (m, 1H), 4.05-4.15 (m, 1H), 3.65-3.80 (m, 2H), 2.82-2.98 (m, 2H), 0.85-1.03 (m, 2H), 0.04 (s, 9H).

Example 26

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-tyrosine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0227 g, 0.042 mmol), (R)-tyrosine tert-butylester (0.0144 g, 0.061 mmol), N-methylmorpholin (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete. The solvent was removed under reduced pressure and the residue was purified by preparative HPLC on a Kromasil C8-column using a gradient of 5-100% MeCN in 0.15% trifluoroacetic acid buffer as eluent. After removing the solvent under reduced pressure the compound (M/z 704.1) was dissolved in methanol (2 ml). NaBH$_4$ (0.004 g, 0.105 mmol) was added and when the reaction was complete a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.021 g (71%) of the title product was obtained. NMR (400 MHz, CD$_3$COOD) 2.85-3.10 (m, 4H), 3.90 (ABq, 2H), 4.03 (d, 0.5H), 4.05 (d, 0.5H), 4.51 (dd, 1H), 4.55 (ABq, 2H), 4.79-4.84 (m, 1H), 4.89 (d, 0.5H), 4.90 (d, 0.5H), 6.62-6.67 (m, 2H), 6.95-7.05 (m, 8H), 7.25-7.37 (m, 6H)

Example 27

N-{[4-((2R,3R)-1-(4-fluorophenyl)-3-{[2-(4-fluorophenyl)-2-hydroxyethyl]thiol-4-oxoazetidin-2-yl)phenoxy]acetyl}glycyl-D-proline A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0197 g, 0.036 mmol), (R)-proline tert-butylester (0.0118 g, 0.069 mmol), N-methylmorpholin (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete. The solvent was removed under reduced pressure and the residue was purified by preparative HPLC on a Kromasil C8-column using a gradient of 5-100% MeCN in 0.15% trifluoroacetic acid buffer as eluent. After removing the solvent under reduced pressure the compound (M/z 638.08) was dissolved in methanol (2 ml). NaBH$_4$ (0.004 g, 0.106 mmol) was added and when the reaction was complete a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.020 g (85%) of the title product was obtained. NMR (400 M/z, CD$_3$COOD) 1.80-1.94 (m, 1H), 1.94-2.10 (m, 1.51°), 2.12-2.35 (m, 1.5H), 2.90-3.06 (m, 2H), 3.49-3.67 (m, 2H), 3.85 (d, 0.5H), 4.00-4.07 (m, 1.5H), 4.14-4.24 (m, 1H), 4.35 (dd, 0.51°), 4.41 (brd, 0.5H), 4.57 (s, 1H), 4.59 (s, 1H), 4.78-4.84 (m, 1H), 4.89 (d, 0.51°), 4.91 (d, 0.5H), 6.95-7.08 (m, 6H), 7.25-7.38 (m, 6H).

Example 28

N-{[4-((2R,3R)-1-(4-fluorophenyl)-3-{[2-(4-fluorophenyl)-2-hydroxyethyl]thio-4-oxoazetidin-2-yl)phenoxy]acetyl glycyl-L-threonine N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-threonine (0.014 g, 0.022 mmol) was dissolved in methanol (2 ml). NaBH$_4$ (0.003 g, 0.079 mmol) was added and when the reaction was complete a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.012 g (85%) of the title product was obtained. NMR (400 MHz, CD$_3$COOD) 1.14 (d 3H), 2.91-3.07 (m, 2H), 4.00-4.08 (m, 3H), 4.21-4.30 (m, 1H), 4.35 (d, 1H), 4.60 (s, 2H), 4.78-4.85 (m, 1H), 4.89 (d, 0.5H), 4.91 (d, 0.5H), 6.96-7.03 (m, 4H), 7.04-7.08 (m, 2H), 7.24-7.38 (m, 6H).

Example 29

N-{[4-((2R,3R)-1-(4-fluorophenyl)-3-{[2-(4-fluorophenyl)-2-hydroxyethyl]thio 1-oxoazetidin-2-yl) phenoxy]acetyl}glycyl-D-lysine A mixture of 3-(R)$_4$-(R)-1-(4-Fluorophenyl)-3-[(4-fluorobenzoyl)methylthio]-4-{4-[N-(carboxymethyl) carbamoylmethoxy]phenyl}azetidin-2-one (0.0209 g, 0.039 mmol), tert-butyl N$^6$-(tert-butoxycarbonyl)-D-lysinate hydrochloride (0.0205 g, 0.060 mmol), N-methylmorpholin (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete. The solvent was removed under reduced pressure and the residue was purified by preparative HPLC on a Kromasil C8-column using a gradient of 5-100% MeCN in 0.15% trifluoroacetic acid buffer as eluent. After removing the solvent under reduced pressure the compound (M/z 669.13) was dissolved in methanol (2 ml). NABH$_4$ (0.005 g, 0.132 mmol) was added and when the reaction was complete a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.020 g (83%) of the title product was obtained. NMR (400 MH,CD$_3$COOD) 1.34-1.47 (m 2H), 1.56-1.74 (m, 3H), 1.84-1.93 (m, 1H), 2.84-3.07 (m, 4H), 3.94 (ABq, 2H), 4.02 (d, 0.5H), 4.05 (d, 0.5H), 4.27 (dd, 1H), 4.61 (s, 2H), 4.79-4.85 (m, 1H), 4.90 (d, 0.5H), 4.91 (d, 0.5H), 6.95-7.08 (m, 6H), 7.24-7.38 (m, 6H).

Example 30

N-{[4-((2R,3R)-1-(4-fluorophenyl)-3-{[2-(4-fluorophenyl)-2-hydroxyethyl]thio)-4-oxoazetidin-2-yl) phenoxy]acetyl}glycyl-L-asparagine N-{[4-((2R,3R)-1-(4-fluorophenyl)-3-{[2-(4-fluorophenyl)-2-oxoethyl]thio}-4-oxoazetidin-2-yl)phenoxy] acetyl}glycyl-L-asparagine (0.020 g, 0.031 mmol) was dissolved in methanol (2 ml). NaBH$_4$ (0.004 g, 0.106 mmol) was added and when the reaction was complete according to LC-MS a few drops of acetic acid were added. The solvent was removed under reduced pressure and the residue was purified by preparative HPLC on a Kromasil C8-column using 35% MeCN in 0.1M ammonium acetate buffer as eluent. After freeze-drying, 0.016 g (80%) of the title product was obtained. NMR (400 MHz, CD$_3$COOD) 2.62 (dd 1H), 2.73 (dd, 1H), 2.90-3.07 (m, 2H), 3.89-4.08 (m, 3H), 4.55 (dd, 1H), 4.60 (ABq, 2H), 4.78-4.85 (m, 1H), 4.90 (d, 0.5H), 4.92 (d, 0.5H), 6.96-7.09 (m, 6H), 7.24-7.38 (m, 6H).

Example 31

N-{[4-((2R,3R)-1-(4-fluorophenyl)-3-{[2-(4-fluorophenyl)-2-hydroxyethyl]thiol-4-oxoazetidin-2-yl) phenoxy]acetyl}glycyl-L-methionine N-{[4-((2R,3R)-1-(4-fluorophenyl)-3-{[2-(4-fluorophenyl)-2-oxoethyl]thio)}-4-oxoazetidin-2-yl)phenoxy] acetyl}glycyl-L-methionine (0.015 g, 0.022 mmol) was dissolved in methanol (2 ml). NaBH$_4$ (0.004 g, 0.106 mmol) was added and when the reaction was complete a few drops of acetic acid were added. The solvent was removed under reduced pressure and the residue was purified by preparative HPLC on a Kromasil C8-column using 35% MeCN in 0.1M ammonium acetate buffer as eluent. After freeze-drying, 0.015 g (99%) of the title product was obtained. NMR (400 MHz, CD$_3$COOD) 1.86-2.00 (m, 1H), 2.04 (s, 3H); 2.07-2.18 (m, 1H), 2.45-2.51 (m, 2H), 2.90-3.08 (m, 2H), 3.97 (s, 2H), 4.04 (d, 0.5H), 4.06 (d, 0.5H), 4.36-4.43 (m, 1H), 4.60 (s, 2H), 4.77-4.85 (m, 1H), 4.90 (d, 0.5H), 4.92 (d, 0.5H), 6.95-7.08 (m, 6H), 7.25-7.38 (m, 6H).

Example 32

N-{[4-((2R,3R)-1-(4-fluorophenyl)-3-{[2-hydroxy-2-(4-methoxyphenyl)ethyl]thio}-4-oxoazetidin-2-yl) phenoxy]acetyl}glycyl-D-valine N-{[4-((2R,3R)-1-(4-fluorophenyl)-3-{[2-(4-methoxyphenyl)-2-oxoethyl]thio}-4-oxoazetidin-2-yl)phenoxy] acetyl}glycyl-D-valine (0.015 g, 0.023 mmol) was dissolved in methanol (3 ml). NABH$_4$ (0.006 g, 0.158 mmol) was added and when the reaction was complete a few drops of acetic acid were added. The solvent was removed under reduced pressure and the residue was purified by preparative HPLC on a Kromasil C8-column using 25% MeCN in 0.1M ammonium acetate buffer as eluent. After freeze-drying, 0.014 g (93%) of the title product was obtained. NMR (500 MHz, CD$_3$COOD) 0.93 (d, 3H), 0.95 (d, 3H), 2.12-2.22 (m, 1H), 2.91-3.07 (m, 2H), 3.75 (s, 1.5H), 3.76 (s, 1.5H), 3.94-4.06 (m, 3H), 4.33 (d, 1H), 4.60 (s, 2H), 4.72-4.78 (m, 1H), 4.81-4.88 (m, 1H), 6.79-6.83 (m, 2H), 6.97-7.08 (m, 4H), 7.20-7.36 (m, 6H).

Example 33

N-{[4-((2R,3R)-1-(4-fluorophenyl)-3-{[2-(4-fluorophenyl)-2-hydroxyethyl]thiol-4-oxoazetidin-2-yl) phenoxy]acetyl}glycyl-D-leucine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.015 g, 0.028 mmol), tert-butyl D-leucinate hydrochloride (0.010 g, 0.045 mmol), N-methylmorpholin (0.0092 ml, 0.083 mmol) in DCM (2 ml) was stirred at room temperature. TBTU (0.012 g, 0.037 mmol) was added and the mixture was stirred overnight. Trifluoroacetic acid (1.0 ml) was added and after 2 h the solvent was removed under reduced pressure and the residue was purified by preparative HPLC on a Kromasil C8-column using a gradient of 5-100% MeCN in 0.15% trifluoroacetic acid buffer as eluent. After removing the solvent under reduced pressure the compound (M/z 654.25) was dissolved in methanol (2 ml). NABH$_4$ (0.005 g, 0.132 mmol) was added and the mixture was stirred for 5 minutes. A few drops of acetic acid was added and the solvent was removed under reduced pressure and the residue was purified by preparative HPLC on a Kromasil C8-column using 35% MeCN in 0.1M ammonium acetate buffer as eluent. After freeze-drying, 0.014 g (76%) of the title product was obtained. NMR (400 MHz,CD$_3$COOD) 0.90-0.94 (m, 6H), 1.52-1.74 (m, 3H), 2.90-3.07 (m, 2H), 3.97 (s 2H), 4.02 (d, 0.5H), 4.04 (d, 0.5H), 4.40 (d, 0.5H), 4.42 (d, 0.5H), 4.59 (s, 2H), 4.78-4.84 (m, 1H), 4.89 (d, 0.5H), 4.91 (d, 0.5H), 6.95-7.08 (m, 6H), 7.24-7.37 (m, 6H).

Example 34

N-{[4-((2R,3R)-1-(4-fluorophenyl)-3-{[2-hydroxy-2-(4-methoxyphenyl)ethyl]thio}-4-oxoazetidin-2-yl)phenoxy]acetyl}glycyl-D-lysine A mixture of N-{[4-((2R,3R)-1-(4-fluorophenyl)-3-{[2-(4-methoxyphenyl)-2-oxoethyl]thio}-4-oxoazetidin-2-yl)phenoxy]acetyl}glycine (0.0177 g, 0.032 mmol tert-butyl $N^6$-(tert-butoxycarbonyl)-D-lysinate hydrochloride (0.0141 g, 0.042 mmol), N-methylmorpholin (0.0106 ml, 0.096 mmol) in DCM (2 ml) was stirred at room temperature. TBTU (0.013 g, 0.042 mmol) was added and the mixture was stirred for 2 h. Additional tert-butyl $N^6$-(tert-butoxycarbonyl)-D-lysinate hydrochloride (0.004 g, 0.012 mmol) was added and after 0.5 h. TBTU (0.008 g, 0.025 mmol) was added and the mixture was stirred for additional 10 minutes. Trifluoroacetic acid (0.65 ml) was added and after 3 h the solvent was removed under reduced pressure. The residue was purified by preparative HPLC on a Kromasil C8-column using a gradient of 5-100% MeCN in 0.15% 1M ammonium acetate buffer as eluent. After removing the solvents under reduced pressure, the intermediate (M/z 681.4) was dissolved in methanol (3 ml). NaBH$_4$ (0.008 g, 0.211 mmol) was added and when the reaction was complete a few drops of acetic acid was added. The solvent was removed under reduced pressure and the residue was purified by preparative HPLC on a Kromasil C8-column using 35% MeCN in 0.1M ammonium acetate buffer as eluent. After freeze-drying, 0.020 g (91%) of the title product was obtained. NMR (500 MHz, CD$_3$COOD) 1.41-1.52 (m, 2H), 1.58-1.78 (m, 3H), 1.90-2.02 (m 1H), 2.86-3.08 (m, 4H), 3.76 (s, 1.5H), 3.77 (s, 1.5), 3.90-4.06 (m, 3H), 4.48 (dd, 1H), 4.60-4.62 (m, 2H), 4.73-4.78 (m, 1H), 4.83-4.89 (m, 1H), 6.80-6.84 (m, 2H), 6.98-7.08 (m, 4H), 7.21-7.31 (m, 4H), 7.31-7.36 (m, 2H), 8.20 (d, NH), 8.54 (t, NH).

Example 35

$N^2$-{[4-((2R,3R)-1-(4-fluorophenyl)-3-{[2 (4-fluorophenyl)-2-hydroxyethyl]thio}-4-oxoazetidin-2-yl)phenoxy]acetyl}-L-glutaminyl-D-phenylalanine $N^2$-{[4-((2R,3R)-1-(4-fluorophenyl)-3-{[2-(4-fluorophenyl)-2-hydroxyethyl]thio}-4-oxoazetidin-2-yl)phenoxy]acetyl}-L-glutamine (15 mg, 0.0244 mmol), tert-butyl D-phenylalaninate hydrochloride (8 mg, 0.0310 mmol) and N-methylmorpholine (10 mg, 0.099 mmol) were dissolved in methylene chloride (0.5 ml). TBTU (10 mg, 0.0313 mmol) was added and the mixture was stirred for 1 h at room temperature. The solvent was evaporated and the residue was dissolved in formic acid (0.5 ml). The mixture was heated to 45-50° C. and stirred at this temperature for 6 h. The reaction mixture was evaporated under reduced pressure. Methanol (5 ml) was added and evaporated. The residue was dissolved in methanol (1 ml). Two drops of TEA was added and the mixture was stirred overnight at room temperature. The solvent was evaporated and the residue was purified by preparative HPLC using acetonitrile/ammonium acetate buffer (40:60) as eluent. After freeze-drying 12 mg (64%) of the title compound was obtained. $^1$H-NMR, 300 MHz, DMSO): 1.55-1.97 (m, 4H), 2.77-3.10 (m, 4H), 4.20-4.38 (m, 3H), 4.49 (s, 2H), 4.66-4.78 (m, 1H), 4.99-5.07 (m, 1H), 6.70 (s, 1H), 6.88-7.40 (m, 19H), 8.00-8.20 (m, 2H).

Example 36

$N^2$-{[4-((2R,3R)-1-(4-fluorophenyl)-3-{[2-(4-fluorophenyl)-2-hydroxyethyl]thio}-4-oxoazetidin-2-yl)phenoxy]acetyl}-L-glutaminyl-D-tyrosine $N^2$-{[4-((2R,3R)-1-(4-fluorophenyl)-3-{[2-(4-fluorophenyl)-2-hydroxyethyl]thio}-4-oxoazetidin-2-yl)phenoxy]acetyl}-L-glutamine (22 mg, 0.0359 mmol), tert-butyl D-tyrosinate hydrochloride (10 mg, 0.0421 mmol) and N-methylmorpholine (14 mg, 0.138 mmol) were dissolved in methylene chloride (0.5 ml). TBTU (14 mg, 0.0436 mmol) was added and the mixture was stirred overnight at room temperature. The solvent was evaporated and the residue was dissolved in formic acid (1 ml). The mixture was stirred at 45-50° C. for 4 h and was then evaporated under reduced pressure. Methanol (10 ml) was added and evaporated. The residue was dissolved in methanol (2 ml). Three drops of TEA were added and the mixture was stirred overnight at room temperature. The solvent was evaporated and the residue was purified by preparative HPLC using acetonitrile/ammonium acetate buffer (40:60) as eluent. After freeze-drying 15 mg (54%) of the title compound was obtained. $^1$H-NMR, 300 MHz, DMSO): 1.60-2.00 (m, 4H), 2.69-3.0 (m, 4H), 4.09-4.18 (m, 1H), 4.22-4.35 (m, 3H), 4.49 (s, 2H), 4.65-4.78 (m, 1H), 4.97-5.08 (m, 1H), 6.56 (d, 2H), 6.70 (s, 1H), 6.86-7.40 (m, 18H), 7.77-7.91 (m, 1H), 8.12 (d, 1H), 9.10 (bs, 1H).

Example 37

N-{[4-((2R,3R)-1-(4-chlorophenyl)-3-{[2-(4-chlorophenyl)-2-hydroxyethyl]thiol-4-oxoazetidin-2-yl)phenoxy]acetyl}glycyl-3-cyclohexyl-D-alanine N-{[4-((2R,3R)-1-(4-chlorophenyl)-3-{[2-(4-chlorophenyl)-2-oxoethyl]thio}-4-oxoazetidin-2-yl)phenoxy]acetyl}glycine (20 mg, 0.0349 mmol) and N-methylmorpholine (20 mg, 0.198 mmol) were dissolved in methylene chloride (0.5 ml). TBTU (17 mg, 0.0530 mmol) was added and the mixture was stirred for 15 min at room temperature. 3-Cyclohexyl-D-alanine (9 mg, 0.0526 mmol) was added and the stirring was continued for 1 h at room temperature. The solvent was evaporated and the residue was dissolved in methanol (0.5 ml). NaBH$_4$ (10 mg, 0.264 mmol) was added and the mixture was stirred for 15 min at room temperature. Three drops of acetic acid was added to the reaction mixture. The product was isolated by preparative HPLC using acetonitrile/ammonium acetate buffer (45:55) as eluent. After freeze-drying 3 mg (12%) of the title compound was obtained. The product was analyzed by LC/Micromass Q TOF micro MS technique. M/z: 728.1973 (calc. Mass 728.1964).

Example 38

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-cyclohexyl-D-alanine N-{[4-((2R,3R)-1-(4-fluorophenyl)-3-{[2-(4-fluorophenyl)-2-oxoethyl]thio}-4-oxoazetidin-2-yl)phenoxy]acetyl}glycine (30 mg, 0.0555 mmol) and N-methylmorpholine (30 mg, 0.296 mmol) were dissolved in DMF (0.5 ml). TBTU (23 mg, 0.0717 mmol) was added and the mixture was stirred for 15 min at room temperature. 3-Cyclohexyl-D-alanine (15 mg, 0.0876 mmol) was added and the stirring was continued overnight at room temperature. The solvent was evaporated under reduced pressure and the residue was dissolved in methanol (1 ml). NaBH4 (10 mg, 0.264 mmol) was added and the mixture was stirred for 10 min at room temperature. Three drops of acetic acid was added to the reaction mixture. The product was isolated by preparative HPLC using acetonitrile/ammonium acetate buffer (40:60) as eluent. After freeze-drying 19 mg (49%) of the title compound was obtained. $^1$H-NMR, 300 MHz, DMSO): 0.68-0.93 (m, 2H), 1.0-1.75 (m, 1H), 2.78-3.00 (m, 2H), 3.73 (s, 2H), 4.00-4.14 (m, 1H), 4.23-4.35 (m, 1H), 4.51 (s, 2H), 4.65-4.78 (m, 1H), 4.99-5.09 (m, 1H), 6.90-7.44 (m, 12H), 7.72-7.86 (m, 1H), 8.26 (t, 1H).

Example 39

N-([4-((2R,3R)-1-(4-fluorophenyl)-3-{[2-(4-fluorophenyl)-2-hydroxyethyl]thiol-4-oxoazetidin-2-yl)phenoxy]acetyl}glycyl-L-phenylalanine N-{[4-((2R,3R)-1-(4-Fluorophenyl)-3-{[2-(4-fluorophenyl)-2-oxoethylthio}-4-oxoazetidin-2-yl)phenoxy]acetyl}glycyl-L-phenylalanine (7 mg, 0.010 mmol) was dissolved in 1.5 ml MeOH and NaBH$_4$ (2 mg, 0.053 mmol) was added. The mixture was stirred for 30 min and quenched with an excess of NH$_4$Ac. LC/MS showed ca 15% starting material. The mixture was diluted with H$_2$O and purified using preparative chromatography on a C8 column (25×300 mm). A gradient from 20% to 40% MeCN in 0.1M ammonium acetate was used as mobile phase. The product fraction was collected and partly concentrated. The mixture was lyophilized to yield 2 mg (29%). M/z: 688 (M−1). NMR (400 MHz, MeOD): 6.95-7.36 (m, 17H), 4.90 (dd, 1H), 4.53-4.59 (m, 4H), 4.03 (dd, 1H), 3.90 (q, 2H), 3.17 (dd, 1H), 2.90-3.05 (m, 3H).

Example 40

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-4-methylleucine tert-Butyl N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-4-methylleucinate (ca 26 mg, 0.036 mmol) was dissolved in 1.5 ml formic acid and heated at 40° C. for 1.5 h. The formic acid was evaporated under reduced pressure. The intermediate acid was confirmed by LC/MS analysis. M/z: 668. The crude mixture was dissolved in 2 ml MeOH. NABH$_4$ (15 mg, 0.40 mmol) was added and the mixture was stirred for 10 min. NH$_4$Ac (30 mg) was added. The crude mixture was diluted with 1 ml water and purified using preparative HPLC on a C8 column (50×300 mm). A gradient from 20% to 40% MeCN in 0.1M ammonium acetate buffer was used as mobile phase. Lyophilization yielded 36 mg white solid. NMR showed the presence of water and HOAc. The product was dried in the vacuum oven for 1.5 h at 40° C. Mass 13 mg (52%). M/z: 668 (M−1). NMR (400 MHz, DMSO): 8.22 (t, 1H), 7.53-7.65 (m, 1H), 7.30-7.38 (m, 4H), 7.20-7.25 (m, 2H), 7.05-7.17 (m, 4H), 6.98 (d, 2H), 5.02-5.06 (m, 1H), 4.68-4.76 (m, 1H), 4.51 (s, 2H), 4.24-4.32 (m, 1H), 4.01-4.09 (m, 1H), 3.60-3.77 (m, 2H), 2.82-2.98 (m, 2H), 1.64 (dd, 1H), 1.33 (dd, 1H), 0.83 (s, 9H).

Example 41

N-{[4-((2R,3R)-1-(4-Fluorophenyl)-3-{[2-(4-fluorophenyl)-2-hydroxyethyl]thio}-4-oxoazetidin-2-yl)phenoxy]acetyl}-D-seryl-D-phenylalanine A solution of N-{[4-((2R,3R)-1-(4-fluorophenyl)-3-([2-(4-fluorophenyl)-2-hydroxyethyl]thio}-4-oxoazetidin-2-yl)phenoxy]acetyl}-D-serine (diastereomeric mixture) (0.008 g, 0.014 mmol), D-phenylalanine tert-butyl ester hydrochloride (0.005 g, 0.018 mmol) and N-Methylmorpholine (0.006 ml, 0.055 mmol) in DCM (3 ml) was stirred at RT for 5 min. TBTU (0.008 g, 0.025 mmol) was added. After 3 days the conversion to the ester (M/z: 776.1) was complete and the mixture was concentrated under reduced pressure. The residue was dissolved in formic acid (3 ml) and the solution was stirred for 25 h. The mixture was concentrated under reduced pressure and the residue was dissolved in MeOH (4 ml) and TEA (1 ml). The solution was stirred at 40° C. for 6 h. The solvent was removed under reduced pressure. The residue was purified by preparative HPLC using a gradient of 20-50% MeCN in 0.1M ammonium acetate buffer as eluent. After freeze-drying, 0.005 g (53% yield) of the title product was obtained as a white solid. M/z: 720.1. 1H NMR (DMSO, 400 MHz): δ 2.78-2.96 (m, 3H), 3.03-3.11 (m, 1H), 3.44-3.60 (m, 2H), 4.20-4.36 (m, 3H), 4.51 (s, 2H), 4.67-4.76 (m, 1H), 5.01-5.06 (m, 1H), 5.70 (bs, 1H), 6.90-6.98 (m, 2H), 7.05-7.25 (m, 1H), 7.29-7.37 (m, 4H), 7.84-8.00 (m, 2H).

Example 42

N-{[4-((2R,3R)-1-(4-Fluorophenyl)-3-{[2-(4-fluorophenyl)-2-hydroxyethyl]thio}-4-oxoazetidin-2-yl)phenoxy]acetyl}-D-seryl-D-serine A solution of N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-serine (0.008 g, 0.014 mmol), O-tert-butyl-D-serine tert-butyl ester hydrochloride (0.005 g, 0.019 mmol) and N-Methylmorpholine (0.006 ml, 0.055 mmol) in DCM (3 ml) was stirred for 5 min. TBTU (0.008 g, 0.025 mmol) was added. After 3 days the conversion to the ester (M/z: 772.5) was complete and the mixture was concentrated under reduced pressure. The residue was dissolved in formic acid (3 ml) and the solution was stirred at RT for 26 h. The mixture was concentrated under reduced pressure and the residue was dissolved in MeOH (4 ml) and TEA (1 ml). The solution was stirred at 40° C. for 6 h. The solvent was removed under reduced pressure. The residue was purified by preparative HPLC using a gradient of 20-50% MeCN in 0.1M ammonium acetate buffer as eluent. After freeze-drying, 0.005 g (52% yield) of the title compound was obtained as a white solid. M/z: 660.1. 1H NMR (DMSO, 400 MHz): δ 2.83-0.95 (m, 2H), 3.42-3.66 (m, 4), 3.91-4.01 (m, 1H), 4.25-4.31 (m, 1H), 4.32-4.39 (m, 1H), 4.54 (ABq, 2H), 4.68-4.76 (m, 1H), 5.02-5.06 (m, 1H), 5.68 (bs, 1H), 6.94-7.00 (m, 2H), 7.05-7.18 (m, 4H), 7.19-7.26 (m, 2H), 7.29-7.39 (m, 4H), 7.74-7.81 (m, 1H), 7.99 (d, 1H).

Example 43

N-{[4-((2R,3R)-1-(4-Fluorophenyl)-3-{[2-(4-fluorophenyl)-2-hydroxyethyl]thiol-4-oxoazetidin-2-yl)phenoxy]acetyl}glycyl-2-butylnorleucine N-{[4-((2R,3R)-1-(4-Fluorophenyl)-3-{[2-(4-fluorophenyl)-2-oxoethyl]thio}-4-oxoazetidin-2-yl)phenoxy]acetyl}glycyl-2-butylnorleucine (0.009 g, 0.012 mmol) was dissolved in MeOH (3 ml). NaBH$_4$ (0.007 g, 0.185 mmol) was added and the mixture was stirred for 10 min. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, 0.008 g (94% yield) of the title compound was obtained as a white solid. M/z: 712.1. $^1$H NMR (DMSO, 400 MHz): δ 0.73-0.83 (m, 6H), 0.89-1.22 (m, 8H), 1.59-1.71 (m, 2H), 1.94-2.06 (m, 2H), 2.83-2.96 (m, 2H), 3.73 (d, 2H), 4.23-4.28 (m, 1H), 4.51 (s, 2H), 4.68-4.76 (m, 1H), 5.02-5.07 (m, 1H), 5.68 (bs, 1H), 6.94-7.00 (m, 2H), 7.05-7.18 (m, 4H), 7.19-7.26 (m, 2H), 7.29-7.39 (m, 4H), 7.53 (s, 1H), 8.30-8.36 (m, 1H).

Example 44

N-{[4-((2R,3R)-1-(4-Fluorophenyl)-3-{[2-(4-fluorophenyl)-2-hydroxyethyl]thiol-4-oxoazetidin-2-yl)phenoxy]acetyl}glycyl-5-methyl-L-cysteine A solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.015 g, 0.028 mmol), tert-butyl S-methyl-L-cysteinate (0.014 g, 0.073 mmol)) and N-methylmorpholine (0.012 ml, 0.109 mmol) in DCM (5 ml) was stirred for 5 min. TBTU (0.013 g, 0.042 mmol) was added. After 20 h, the conversion to the ester (M/z: 714.1) was complete and the mixture was concentrated under reduced pressure. The residue was dissolved in formic acid (3 ml) and the solution was stirred at 40° C. for 22 h. The mixture was diluted with toluene (2 ml) and the solvent was again removed under reduced pressure. The residue was dissolved in MeOH (4 ml) and NaBH$_4$ was added in small portions to the solution (a total of 0.035 g, 0.925 mmol) until the reduction was complete. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, 0.013 g (72% yield) of the title compound was obtained as a white solid. M/z: 660.3. 1H NMR (DMSO, 400 MHz): δ 2.66-2.74 (m, 1H), 2.82-3.02 (m, 3H), 3.67-3.82 (m, 2H), 4.02-4.12 (m, 1H), 4.24-4.31 (m, 1H), 4.52 (s, 2H), 4.68-4.77 (m, 1H), 5.01-5.07 (m, 1H), 6.95-7.02 (m, 2H), 7.05-7.18 (m, 4H), 7.19-7.26 (m, 2H), 7.29-7.40 (m, 4 Hz, 7.73-7.82 (m, 1H), 8.30-8.37 (m, 1H).

Example 45

N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl-L-isoleucine A solution of N-{[4-((2R,3R)-1-(4-Fluorophenyl)-3-{[2-(4-fluorophenyl)-2-oxoethyl]thiol-4-oxoazetidin-2-yl)phenoxy]acetyl}glycine (0.015 g, 0.028 mmol), L-isoleucine t-butyl ester hydrochloride (0.008 g, 0.036 mmol) and N-methylmorpholine (0.012 ml, 0.109 mmol) in DCM (5 ml) was stirred for 5 min. TBTU (0.012 g, 0.036 mmol) was added. After 22 h, the conversion to the ester (M/z: 710.2) was complete and the mixture was concentrated under reduced pressure. The residue was dissolved in formic acid (3 ml) and the solution was stirred at 40° C. for 20 h. The mixture was diluted with toluene (2 ml) and the solvent was removed under reduced pressure. The residue was dissolved in MeOH (4 ml) and NaBH was added in small portions to the solution (a total of 0.060 g, 1.59 mmol) until the reduction was complete. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, 0.010 g (57% yield) of the title compound was obtained as a white solid. M/z: 656.2. 1H NMR (DMSO, 400 MHz): δ 0.76-0.84 (m, 6H), 1.05-1.17 (m, 1H), 1.32-1.44 (m, 1H), 1.67-1.78 (m, 1H), 2.82-2.95 (m, 2H), 3.78 (d, 2H), 4.03-4.11 (m, 1H), 4.23-4.29 (m, 1H), 4.51 (s, 2H), 4.68-4.77 (m, 1H), 5.01-5.07 (m, 1H), 6.94-7.01 (m, 2H), 7.05-7.26 (m, 6H), 7.29-7.39 (m, 4H), 7.79-7.89 (m, 1H), 8.22-8.28 (m, 1H).

Example 46

N-{[4-((2R,3R)-1-(4-Fluorophenyl)-3-{[2-(4-fluorophenyl)-2-hydroxyethy]thio}-4-oxoazetidin-2-yl)phenoxy]acetyl}-L-alanyl-D-valine A solution of N-{[4-((2R,3R)-1-(4-Fluorophenyl)-3-([2-(4-fluorophenyl)-2-oxoethyl]thio}-4-oxoazetidin-2-yl)phenoxy]acetyl}-L-alanine (0.015 g, 0.027 mmol), D-valine tert-butyl ester hydrochloride (0.008 g, 0.038 mmol) and N-methylmorpholine (0.030 ml, 0.272 mmol) in DCM (4 ml) was stirred for 5 min. TBTU (0.013 g, 0.041 mmol) was added. After 3 h, the conversion to the ester (M/z: 710.2) was completed and TFA (3 ml) was added. After 4 h, the mixture was diluted with toluene (2 ml) and the solvent was removed under reduced pressure. The residue was dissolved in MeOH (4 ml) and NaBH$_4$ was added in small portions to the solution (a total of 0.065 g, 1.72 mmol) until the reduction was complete. Ammonium acetate buffer (0.1M, 3 ml) was added and most of the methanol was removed under reduced pressure. The remaining solution was purified by preparative HPLC, using a gradient of 20-50% MeCN in a 0.1M ammonium acetate buffer as eluent. After freeze-drying, 0.014 g (77% yield) of the title compound was obtained as a white solid. M/z: 656.1. 1H NMR (DMSO, 400 MHz): δ 0.75-0.83 (m, 6H), 1.22 (d, 3H), 1.95-2.07 (m, 1H), 3.83-3.96 (m, 2H), 3.98-4.06 (m, 1H), 4-24-4.31 (m, 1H), 4.40-4.54 (m, 3H), 4.67-4.76 (m, 1H), 5.01-5.07 (m, 1H), 6.91-7.98 (m, 2H), 7.05-7.17 (m, 4H), 7.19-7.25 (m, 2H), 7.29-7.39 (m, 4H), 7.84-7.95 (m, 1H). 8.07 (d, 1H), Example 47

1-[(N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl)amino]cyclopentanecarboxylic acid N-{[4-((2R,3R)-1-(4-Fluorophenyl)-3-{[2-(4-fluorophenyl)-2-oxoethyl]thio}-4-oxoazetidin-2-yl)phenoxy] acetyl}glycine (0.015 g, 0.028 mmol), NMM (0.012 ml, 0.109 mmol) and TBTU (0.011 g, 0.034 mmol) were dissolved in DMF (2 ml) at 30° C. After 30 min 1-amino-1-cyclopentanecarboxylic acid (0.004 g, 0.030 mmol, 97%) was added and the mixture was stirred at 30° C. for 1 h. The reaction was quenched with water (0.2 ml) and the mixture was diluted with MeOH (2 ml). NaBH4 (0.015 g, 0.397 mmol) was added and the mixture was stirred for 10 min. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, the title compound (0.009 g, 49% yield) was obtained as a white solid. M/z: 654.0. 1H NR (DMSO, 400 M/z): δ 1.56-1.66 (m, 4H), 1.78-1.87 (m, 2H), 1.97-2.07 (m, 2H), 2.84-2.94 (m, 2H), 3.74 (d, 2H), 4.24-4.29 (m, 1H), 4.51 (s, 2H), 4.68-4.76 (m, 1H),

Example 48

N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl-N-benzylglycine TBTU (0.011 g, 0.034 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.015 g, 0.028 mmol) and NMM (0.020 ml, 0.182 mmol) in DMF (2 ml) at 30° C. After 30 min, N-enzylglycine (0.005 g, 0.030 mmol, 98%) was added and the mixture was stirred at 30° C. for 1 h. The reaction was quenched with water (0.2 ml) and the mixture was diluted with MeOH (2 ml). NaBH$_4$ (0.015 g, 0.397 mmol) was added and the mixture was stirred for 10 min. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, the title compound (0.010 g, 53% yield) was obtained as a white solid. M/z: 690.0. 1H NMR (DMSO, 400 MHz): δ 2.83-2.94 (m, 2H), 3.91 (s, 1H), 3.98-4.09 (m, 3H), 4.25-4.29 (m, 1H), 4.50 (s, 2H), 4.54 (s, 1H), 4.62 (s, 1H), 4.68-4.76 (m, 1H), 5.02-5.07 (m, 1H), 6.92-7.02 (m, 2H), 7.05-7.40 (m, 15H), 8.14-8.21 (m, 1H).

Example 49

[(N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl)amino](diphenyl)acetic acid TBTU (0.016 g, 0.050 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.020 g, 0.037 mmol) and NMM (0.012 ml, 0.109 mmol) in DMF (2 ml) at 30° C. After 30 min, 2,2-diphenylglycine (0.009 g, 0.037 mmol, 98%) was added and the mixture was stirred at 30° C. for 2.5 h. The reaction was quenched with water (0.2 ml) and the mixture was diluted with MeOH (2 ml). NaBH$_4$ (0.020 g, 0.529 mmol) was added and the mixture was stirred for 10 min. Ammonium acetate buffer (0.1M, 3 ml) was added and most of the methanol was removed under reduced pressure. The remaining solution was purified by preparative HPLC, using a gradient of 20-50% MeCN in 0.1M ammonium acetate buffer as eluent. After freeze-drying, the title compound (0.012 g, 44% yield) was obtained as a white solid. M/z: 752.0. 1H NMR (DMSO, 400 MHz): δ 2.83-2.95 (m, 2H), 3.75 (d, 2H), 4.24-4.28 (m, 1H), 4.54 (s, 1H), 4.68-4.75 (m, 1H), 5.02-5.06 (m, 1H), 6.95-7.03 (m, 2H), 7.04-7.38 (m, 20H), 8.43-8.51 (m, 1H), 8.90 (s, 1H).

Example 50

N-{[4-((2R,3R)-1-(4-Fluorophenyl)-3-{[2-(4-fluorophenyl)-2-hydroxyethyl]thiol-4-xoazetidin-2-yl)phenoxy]acetyl}glycylglycine N-{[4-((2R,3R)-1-(4-Fluorophenyl)-3-{[2-(4-fluorophenyl)-2-oxoethyl]thio}-4-oxoazetidin-2-yl)phenoxy]acetyl}glycylglycine (0.011 g, 0.018 mmol) was dissolved in MeOH (3 ml). NaBH$_4$ (0.013 g, 0.344 mmol) was added and the mixture was stirred for 10 min. Ammonium acetate buffer (0.1M, 3 ml) was added and most of the methanol was removed under reduced pressure. The remaining solution was purified by preparative HPLC, using a gradient of 20-50% MeCN in a 0.1M ammonium acetate buffer as eluent. After freeze-drying, the title compound (0.011 g, 97% yield) was obtained as a white solid. M/z: 600.0. 1H NMR DMSO, 400 MHz): 2.97-2.84 (m, 2H), 3.44-3.50 (m, 2H), 3.74 (d, 2H), 4.26-4.32 (m, 1H), 4.46-4.54 (m, 2H), 4.67-4.76 (m, 1M), 5.02-5.07 (m, 1H), 6.95-7.01 (m, 2H), 7.05-7.26 (m, 6H), 7.30-7.40 (m, 4H), 7.60-7.80 (m, 1H), 8.32-8.38 (m, 1H).

Example 51

N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-valyl-L-serine N-([4-((2R,3R)-1-(4-Fluorophenyl)-3-{[2-(4-fluorophenyl)-2-oxoethyl]thio}-4-oxoazetidin-2-yl)phenoxy]acetyl}-D-valine (6.9 mg, 11.8 µmol) was dissolved in DCM (3 ml). tert-Butyl O-(tert-butyl)-L-serinate hydrochloride (3.7 mg, 14.2 µmol) and N-methylmorpholine (5.5 µl, 50 µmol) were added. After 5 minutes, TBTU (4.6 mg, 14.3 µmol) was added and the reaction mixture was stirred overnight. The formation of the ester was confirmed. M/z: 780.57 (M−1). The mixture was extracted between DCM (5 ml) and aqueous KHSO$_4$ (5 ml, pH of 2). The organic phase was washed with aqueous NaHCO$_3$ (5 ml, pH of 9). The aqueous phase was extracted with DCM (2×5 ml). The combined organic phases were dried over Na$_2$SO$_4$, filtered and concentrated. Formic acid (1.5 ml) was added and the reaction mixture was stirred overnight. The formiate of the intermediate acid was obtained. The solvent was removed under reduced pressure, toluene (3×1 ml) was added and evaporated. The residue was dissolved in MeOH (1.5 ml) and triethylamine (90 µl, 0.65 mmol) was added and the reaction mixture was stirred for 1 hour. Sodium borohydride (4.0 mg, 0.11 mmol) was added and the reaction mixture was stirred for 1 hour. Ammonium acetate (15 mg) was added. The solvent was removed under reduced pressure and the residue was purified on preparative HPLC using a C8 column. A gradient from 20% to 50% MeCN in 0.1M ammonium acetate buffer was used as eluent. After lyophilisation, the title compound was obtained as a white solid (5.3 mg, 67%). HRMS calcd for C$_{33}$H$_{35}$F$_2$N$_3$O$_8$S 671.2113, found 672.2192 [M+H]$^+$.

Example 52

N-([4-((2R,3R)-1-(4-fluorophenyl)-3-{[2-(4-fluorophenyl)-2-hydroxyethyl]thiol-4-oxoazetidin-2-yl)phenoxy]acetyl}-D-valylglycine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-valine (11.8 mg, 0.02 mmol), tert-butyl glycinate hydrochloride (4.6 mg, 0.03 mmol) and N-methylmorpholine (10 µl, 0.09 mmol) were dissolved in DCM (1.5 ml). After 5 minutes, TBTU was added and the reaction mixture was stirred for 3.5 h. The formation of the ester was confirmed. M/z: 694.0 (M−H). The mixture was extracted between DCM (3 ml) and aqueous KHSO$_4$ (5 ml, pH of 3). The aqueous phase was extracted with DCM (2×5 ml). The combined organic phases were washed with water (2×5 ml), dried over Na$_2$SO$_4$, filtered and concentrated. Formic acid (3 ml) was added and the solution was heated at 40° C. overnight. The solvent was removed under reduced pressure, toluene was added and evaporated. The residue was dissolved in methanol (3 ml) and sodium borohydride (8.5 mg, 0.23 mmol) was added. The reaction mixture was stirred for 15 minutes. The solvent was removed under reduced pressure. The residue was purified on preparative HPLC on a C8 column. A gradient from 20% to 50% MeCN in 0.1M ammonium acetate buffer was used as eluent. After lyophilisation, the title compound was obtained as a white solid (6.2 mg, 48%). HRMS calcd for $C_{32}H_{33}F_2N_3O_7S$ 641.2007, found 642.2086 [M+H]$^+$.

Example 53

N-{[4-((2R,3R)-1-(4-fluorophenyl)-3-{[2-(4-fluorophenyl)-2-hydroxyethyl]thiol-4-oxoazetidin-2-yl)phenoxy]acetyl}-D-valyl-L-valine N-{[4-((2R,3R)-1-(4-Fluorophenyl)-3-{[2-(4-fluorophenyl)-2-oxoethyl]thio}-4-oxoazefidin-2-yl)phenoxy]acetyl}-D-valine (11.5, 0.02 mmol), tert-butyl L-valinate hydrochloride (5.3 mg, 0.025 mmol) and N-methylmorpholine (10 µl, 0.091 mmol) were dissolved in DCM (1.5 ml).

After 5 minutes, TBTU (7.8 mg, 0.024 mmol) was added and the reaction mixture was stirred overnight. Additional tert-butyl L-valinate hydrochloride (1.5 mg, 7.2 µmol), N-methylmorpholine (6.5 µl, 58 µmol) and TBTU (2.0 mg, 6.2 µmol, 0.31 eq) were added and the mixture was stirred for 2.5 h. The formation of the ester was confirmed. M/z: 736.1 (M−H). The reaction mixture was extracted between aqueous KHSO$_4$ (5 ml, pH of 3) and DCM (5 ml). The organic phase was dried over Na$_2$SO$_4$, filtered and concentrated. The residue was dissolved in formic acid (2 ml) and heated at 40° C. overnight. The solvent was removed under reduced pressure. Toluene was added and removed under reduced pressure. The residue was dissolved in MeOH (2 ml) and sodium borohydride (8.1 mg, 0.21 mmol) was added. The mixture was stirred for 30 minutes. Ammonium acetate (16 mg) was added and the solvent was removed under reduced pressure. The residue was purified with preparative HPLC on a C8 column. A gradient from 20% to 50% MeCN in 0.1 M NH$_4$OAc buffer was used as eluent. After lyophilisation, the title compound was obtained as a white solid (7.3 mg, 54%) H-NMR (400 MHz, DMSO-d$_6$): 0.70 (d, 3H), 0.79 (d, 3H), 0.83 (d, 6H), 2.00 (m, 2H), 2.86-2.92 (m, 2H), 4.07 (brs, 1H), 4.25-4.29 (m, 1H), 4.40 (m, 1H), 4.59 (brs, 2H), 4.72 (m, 1H) 5.03 (d, 0.5H), 5.05 (d, 0.5H), 5.68 (brs, 1H), 6.95 (d, 2H), 7.06-7.16 (m, 4H), 7.19-7.24 (m, 2H), 7.29-7.37 (m, 4H), 7.80 (d, 1H), 8.05-8.15 (brs, 1H). M/z: 682.1 (M−H).

Example 54

N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-valyl-D-valine N-{[4-((2R,3R)-1-(4-fluorophenyl)-3-{([2-(4-Fluorophenyl)-2-oxoethyl]thio}-4-oxoazetidin-2-yl)phenoxy]acetyl}-D-valine (11.9 mg, 0.02 mmol), tert-butyl D-valinate hydrochloride (5.6 mg, 0.027 mmol) and N-methylmorpholine (10 µl, 0.092 mmol) were dissolved in DCM (1.5 ml). After 5 minutes, TBTU (8.2 mg, 0.0255 mmol) was added and the reaction mixture was stirred overnight. Additional tert-butyl D-valinate hydrochloride (1.7 mg, 8.1 µmol), N-methylmorpholine (6.5 µl, 58 µmol), TBTU (2 mg, 6.2 µmol) were added and the mixture was stirred for 3 h. The formation of the ester was confirmed. M/z: 736.2 (M−H). The solvent was removed under reduced pressure and the residue was purified on silica gel (1 g) using DCM:MeOH (8:2) as eluent. The fractions were collected and concentrated. The residue was dissolved in formic acid (1 ml) and the resulting solution was stirred at 25-30° C. overnight. The solvent was evaporated and toluene was added and removed under reduced pressure. The residue was dissolved in methanol (1 ml) and sodium borohydride (8.8 mg, 0.23 mmol) was added. The mixture was stirred for 30 minutes. Ammonium acetate (18 mg) was added and the solvent was removed under reduced pressure. The residue was purified with preparative HPLC on a C8 column. A gradient from 20% to 50% MeCN in 0.1 M ammonium acetate buffer was used as eluent. After lyophilisation, the title compound was obtained as a white solid (2.5 mg, 18%). H-NMR (400 M, DMSO-d$_6$): 0.75 (d, 3H), 0-79-0.87 (m, 9H), 1.92-2.06 (m, 2H), 2.86-2.92 (m, 2H), 4.01 (brs, 1H), 4.25 (d, 0.5H), 4.28 (d, 0.5H), 4.32 (t, 1H), 4.57 (d, 2H), 4.67-4.76 (m, 1H), 5.03 (d, 0.5H), 5.05 (d, 0.5H), 5.69 (brs, 1H), 6.93 (d, 2H), 7.04-7.17 (m, 4H), 7.18-7.25 (m, 2H), 7.29-7.38 (m, 4H), 7.85 (d, 1H), 7.96 (brs, 1H). M/z: 682.1 (M−H).

Example 55

N-{[4-((2R,3R)-1-(4-fluorophenyl)-3-([2-(4-fluorophenyl)-2-hydroxyethyl]thio}-4-oxoazetidin-2-yl)phenoxy]acetyl}-D-valyl-L-methionine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-valine (13.3 mg, 0.023 mmol), tert-butyl L-methioninate hydrochloride (7.4 mg, 0.031 mmol) and N-methylmorpholine (10 µl, 0.091 mmol) were dissolved in 1 ml. After 5 minutes, TBTU (8.9 mg, 0.028 mmol) was added and the resulting suspension was stirred overnight. Additional tert-butyl L-methioninate hydrochloride (2.1 mg, 0087 mmol), N-methylmorpholine (5 µl, 45 µmol) and TBTU (2.1 mg, 6.54 µmol) were added and the mixture was stirred for 2 h. The formation of the ester was confirmed. MHz 768.1 (M−H) and 770.0 (M+H). The yellow suspension was purified on silica gel (1 g) and eluted with EtOAc:DCM (15:85). The pure fractions were concentrated and formic acid (1.5 ml) was added. The solution was stirred at 50° C. overnight. The solvent was removed under reduced pressure. Toluene was added and removed under reduced pressure. The residue was dissolved in methanol (1 ml) and sodium borohydride (9.9 mg, 0.26 mmol) was added. The resulting reaction mixture was stirred for 10 minutes. Ammonium acetate (18.9 mg) was added and the solvent was removed under reduced pressure. The residue was purified with preparative HPLC on a C8 column. A gradient from 20% to 40% MeCN in 0.1 M ammonium acetate buffer was used as eluent. After lyophilisation, the title compound was obtained as a white solid was obtained (4.6 mg, 28%). 1H-NMR (400 MHz, DMSO-d$_6$): 0.75 (d, 3H), 0.79 (d, 3H), 1.79-1.97 (m, 3H), 1.99 (s, 3H), 2.36-2.44 (m, 2H), 2.86-2.92 (m, 2H), 2.24-4.35 (m, 3H), 4.58 (d, 2H), 4.67-4.76 (m, 1H), 5.03 (d, 0.5H), 5.5 (d, 0.5H), 5.63 (t, 1H), 6.95 (d, 2H), 7.05-7.16 (m, 4H), 7.18-7.24 (m, 2H), 7.30-7.38 (m, 2H), 7.82 (d, 1H), 7.37 (d, 1H). M/z: 714.0 (M−1) and 716.1 (M+H).

Example 56

N-[(4-{(2R,3R)-1-(4-fluorophenyl)-3-[(2-hydroxy-2-phenylethyl)thio]-4-oxoazetidin-2-yl}phenoxy)acetyl]glycyl-D-valine (4-{(2R,3R)-1-(4-Fluorophenyl)-4-oxo-3-[(2-oxo-2-phenylethyl)thio}azetidin-2-yl]phenoxy)acetic acid (15 mg, 0.043 mmol), tert-butyl glycyl-D-valinate hydrochloride, (14.3 mg, 0.054 mmol) and N-methylmorpholine (14 µl, 0.13 mmol) were dissolved in DCM (2 ml). After 5 minutes, TBTU (16.9 mg, 0.053 mmol) was added and the reaction mixture was stirred for 2.5 h. The formation of the ester was confirmed. M/z: 678.35 (N+H). The solvent was removed under reduced pressure. The residue was dissolved in EtOAc:DCM (1:3) and purified on silica gel (1 g) using EtOAc:DCM (1:3) as eluent. The fractions were collected and concentrated. The residue (0.029 g) was dissolved in DCM (3 ml) and TFA (0.5 ml) was added. The reaction mixture was stirred overnight. The solvent was removed under reduced pressure and toluene was added and removed under reduced pressure. The yellowish residue was dissolved in MeOH (2 ml) and sodium borohydride (16.2 mg, 0.43 mmol) was added. The reaction mixture was stirred for 10 minutes. Ammonium acetate (31.4 mg) was added and the solvent was removed under reduced pressure. The residue was purified with preparative HPLC on a C8 column. A gradient from 20% to 50% MeCN in 0.1 M ammonium acetate buffer was used as eluent. After lyophilisation, the title compound was obtained as a white solid (7.6 mg, 28%). H-NMR (400 MHz, DMSO-$d_6$): 0.79 (d, 3H), 0.81 (d, 3H) 1.95-2.05 (m, 1H), 2.84-2.96 (m, 2H), 3.79 (d, 2H), 3.98-4.04 (m, 1H), 4.27 (d, 0.5H), 4.30 (d, 0.5H), 4.51 (s, 2H), 4.66-4.75 (m, 1H), 5.02 (d, 0.5H), 5.04 (d, 0.5H), 6.98 (d, 2H), 7.10-7.17 (m, 2H), 7.19-7.32 (m, 7H), 7.36 (d, 2H), 7.77 (t, 1H), 8.26 (t, 1H). M/z: 622.1 (M−H) and 624.2 (M+H).

Example 57

N-{[4-((2R,3R)-1-(4-fluorophenyl)-3-{[2-hydroxy-2-(4-methylphenyl)ethyl]thio}-4-oxoazetidin-2-yl)phenoxy]acetyl}glycyl-D-valine

[4-((2R,3R)-1-(4-Fluorophenyl)-3-{[2-(4-methylphenyl)-2-oxoethyl]thio)}-4-oxoazetidin-2-yl)phenoxy]acetic acid (15.0 mg, 0.043 mmol), tert-butyl glycyl-D-valinate hydrochloride (10.8 mg, 0.04 mmol), N-methylmorpholine (10 µl, 0.09 mmol) were dissolved in DCM (2 ml). After 5 minutes, TBTU (12.1 mg, 0.04 mmol) was added and the reaction mixture was stirred overnight. The formation of the ester was confirmed. M/z: 690.13 (M−H) and 692.15 M+H). The reaction mixture was purified on silica gel (1 g) and eluted with EtOAc:DCM (1:4). The collected fractions were concentrated. The oily residue was dissolved in DCM (1.5 ml) and TFA (1 ml) was added. The reaction mixture was stirred for 2.5 h. The solvent was evaporated. Toluene was added and evaporated to assist the removal of TFA. The residue was dissolved in methanol (1.5 ml) and sodium borohydride (12.2 mg, 0.32 mmol) was added. Additional sodium borohydride (4.2 mg, 0.11 mmol) was added and the mixture was stirred for 15 minutes. The solvent was removed under reduced pressure and the residue was purified on preparative HPLC on a C8 column. A gradient from 20% to 50% MeCN in 0.1M ammonium acetate buffer was used as eluent. After lyophilisation, the title compound was obtained as a white solid (10.4 mg, 52%). H-NMR (400 MHz, DMSO-$d_6$): 0.80 (d, 6H), 1.95-2.05 (m, 1H), 2.24 (brs, 3H), 2.80-2.94 (m, 2H), 3.78 (d, 2H), 4.00 (brs, 1H), 4.23 (d, 0.5H), 4.27 (brs, 0.5H) 4.51 (s, 2H), 4.61-4.70 (m, 1H), 5.00 (m, 1H), 6.97 (d, 2H) 7.06 (d, 2H), 7.10-7.18 (m, 4H), 7.19-7.25 (m, 2H), 7.34 (d, 2H), 7.76 (brs, 1H), 8.26 (t, 1H). M/z: 636.1 (M−H) and 638.1(M+H).

Example 58

N-{[4-((2R,3R)-1-(4-fluorophenyl)-3-{[2-(4-fluorophenyl)-2-hydroxyethyl]thiol-4-oxoazetidin-2-yl)phenoxy]acetyl}-D-valyl-D-tyrosine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-valine (14.7 mg, 0.025 mmol), added tert-butyl D-tyrosinate hydrochloride (10.5 mg, 0.038 mmol) and N-methylmorpholine (10 µl, 91 µmol) were dissolved in DCM (1.5 ml). After 5 minutes, TBTU (9.9 mg, 0.031 mmol) was added and the reaction mixture was stirred overnight. Additional tert-butyl D-tyrosinate hydrochloride (3.6 mg, 0.013 mmol), N-methylmorpholine (10 µl, 91 µmol) and TBTU (3.1 mg, 9.7 µmol) were added. The mixture was stirred for 3 h. The formation of the ester was confirmed. M/z. 800.07 (M−H) and 802.08 (M+H). Aqueous $KHSO_4$ (3 ml) was added and the mixture (pH of 2) was extracted with DCM (3×5 ml). The combined organic phases were washed with water (2×10 ml), dried over $Na_2SO_4$, filtered and concentrated. The oily residue (22.4 mg) was dissolved in DCM (1.5 ml) and TFA (1.0 ml) was added. The mixture was stirred overnight. The solvent was evaporated. Toluene was added and removed under reduced pressure. The residue was dissolved in methanol (2 ml) and sodium borohydride (14 mg) was added. The solution was stirred for 10 minutes. Ammonium acetate (15 mg) was added and the solvent was removed under reduced pressure. The residue was purified with preparative HPLC on a C8 column. A gradient from 20% to 50% MeCN in 0.1M ammonium acetate buffer was used as eluent. After lyophilisation, the title compound was obtained as a white solid (8.4 mg, 45%).

1H-NMR (400 MHz, DMSO-$d_6$): 0.70 (d, 3H), 0.76 (d, 3H), 1.90-1.99 (m, 1H), 2.73-2.80 (m, 1H), 2.86-2.95 (m, 3H), 3.96-4.04 (m, 1H), 4.06-4.12 (m, 1H), 4.27 (d, 0.5H), 4.29 (d, 0.5H), 4.50-4.61 (m, 2H), 4.67-4.76 (m, 1H), 5.02 (d, 0.5H), 5.04 (d, 0.5H), 6.53 (d, 2H), 6.91 (q, 4H), 7.04-7.15 (m, 4H), 7.18-7.25 (m, 2H), 7.30-7.38 (m, 4H), 7.58-7.65 (brs, 1H), 7.91 (d, 1H). M/z: 746.0 (M−H).

Example 59

N-{[4-((2R,3R)-1-(4-fluorophenyl)-3-{[2-(4-fluorophenyl)-2-hydroxyethyl]thio}-4-oxoazetidin-2-yl)phenoxy]acetyl}-D-valyl-D-lysine N-{[4-((2R,3R)-1-(4-Fluorophenyl)-3-{[2-(4-fluorophenyl)-2-oxoethyl]thio}-4-oxoazetidin-2-yl)phenoxy]acetyl}-D-valine (14.7, 0.025 mmol), tert-butyl $N^6$-(tert-butoxycarbonyl)-D-lysinate hydrochloride (10.3, 0.03 mmol) and N-methylmorpholine (10 µl, 91 µmol) were dissolved in DCM (1.5 ml). After 5 min, TBTU (9.8 mg, 0.03 mmol) was added and the reaction mixture was stirred overnight. Additional $N^6$-(tert-butoxycarbonyl)-D-lysinate hydrochloride (3.4 mg, 0.01 mmol), N-methylmorpholine (5 µl, 45/µmol) and TBTU (3.3 mg, 0.01 mmol) were added and the mixture was stirred for 2 h. Aqueous $KHSO_4$ (3 ml) was added and the mixture (pH of 3) was extracted with DCM (3×5 ml). The combined organic phases were washed with water (2×5 ml) and dried over $Na_2SO_4$. The solvent was removed under reduced pressure. The crude residue (17.1 mg) was dissolved in DCM (1.5 ml) and TFA (1 ml). The solution was stirred for 1.5 h. The solvent was removed under reduced pressure. Toluene was added and evaporated to assist the removal of TFA. The residue was dissolved in methanol (2 ml) and sodium borohydride (11.5 mg, 0.30 mmol) was added. The mixture was for ca 15 minutes. After removal of the solvent under reduced pressure, the residue was purified with preparative HPLC on a C8 column. A gradient from 20% to 50% MeCN in 0.1M ammonium acetate buffer was used as eluent. After lyophilisation, the title compound was obtained as a white solid. (7.8 mg, 43%). 1H-NMR (400 MHz, DMSO-$d_6$): 0.75 (d, 3H), 0.79 (d, 3H), 1.17-1.63 (m, 4H), 1.96-2.06 (m, 1H), 2.61-2.69 (m, 2H), 2.85-2.93 (m, 2H), 3.72-3.80 (m, 1H), 4.12 (t, 1H), 4.27 (s, 0.5H), 4.30 (s, 0.5H), 4.53-5.64 (m, 2H), 4.67-4.76 (m, 1H), 5.01-5.05 (m, 1H), 6.94 (d, 2H), 7.03-7.16 (m, 4H), 7.29-7.39 (m, 4H), 7.50-7.57 (brs, 1H), 8.05 (d, 1H). M/z: 713.1.

Example 60

N-[(4-{(2R,3R)-3-[(2-hydroxy-2-phenylethyl)thio]-4-oxo-1-phenylazetidin-2-yl}phenoxy)acetyl]glycyl-D-valine

[4-((2R,3R)-3-{[(5,5-Dimethyl-2-phenyl-1,3-dioxan-2-yl)methyl]thio}-4-oxo-1-phenylazetidin-2-yl)phenoxy]acetic acid (12.6 mg, 0.024 mmol) and N-methylmorpholine (15 µl, 0.14 mmol) were dissolved in DCM (2 ml). Additional DCM (2 ml), N-methylmorpholine (20 µl, 0.18 mmol) and tert-butyl glycyl-D-valinate hydrochloride, (9.0 mg, 0.034 mmol) were added after 0.5 h and the mixture was stirred for 10 minutes. TBTU (10.5 mg, 0.033 mmol) was added and the mixture was stirred overnight. The formation of the ester was confirmed. M/z: 746.1. The solvent was removed under reduced pressure and the residue was purified with preparative HPLC on a C8 column. A gradient from 20% to 50% MeCN in 0.1 M ammonium acetate buffer was used as eluent. After lyophilisation, the obtained compound was dissolved in DCM (2 ml) and TFA (1 ml) was added. The reaction mixture was stirred for 2.5 h. The hydrolysis of the ester was confirmed. M/z: 604.2. The solvent was removed under reduced pressure. Co-evaporation with toluene was performed to assist the removal of TFA. The residue was dissolved in methanol (2 ml) and sodium borohydride (9.2 mg, 0.24 mmol) was added. After 15 minutes, the solvent was evaporated off and the residue was purified with preparative HPLC on a C8 column. A gradient from 20% to 50% MeCN in 0.1 M ammonium acetate buffer was used as eluent. After lyophilisation, the title compound was obtained as a white solid was (4.0 mg, 28%). H-NMR (400 MHz, DMSO-$d_6$): 0.78 (d, 6H), 1.95-2.04 (m, 1H), 2.83-2.97 (m, 2H), 3.76 (d, 2H), 3.89-3.95 (m, 1H), 4.26 (d, 0.5H), 4.30 (d, 0.5H), 4.51 (s, 2H), 4.67-4.75 (m, 1H), 5.01 (d, 0.5H), 5.03 (d, 0.5H), 6.98 (d, 2H), 7.03 (t, 1H), 7.17-7.22 (m, 3H), 7.23-7.32 (m, 6H), 7.36 (d, 2H), 7.55-7.65 (m, 1H), 8.29 (t, 1H). M/z: 603.96 (M–H).

Example 61

N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-D-valine

[4-((2R,3R)-1-(4-Chlorophenyl)-3-{[2-(4-chlorophenyl)-2-oxoethyl]thio}-4-oxoazetidin-2-yl)phenoxy]acetic acid (15.3 mg, 0.03 mmol), N-methylmorpholine (10 µl, 0.091 mmol) and tert-butyl glycyl-D-valinate hydrochloride, (10.4 mg, 0.039 mmol) were dissolved in DCM (2 ml). After 10 minutes, TBTU (11.9 mg, 0.037 mmol) was added and the mixture was stirred overnight. The intermediate tert-butylester was confirmed. M/z: 727.8 (M–H). The reaction mixture was extracted between water (10 ml, acidified to pH of 3 with $KHSO_4$ (2M)) and DCM (3×10 ml). The combined organic phases were washed with water (2×20 ml), dried over $Na_2SO_4$, filtered and concentrated. The oily residue was dissolved in DCM (2 ml) and TFA (1.3 ml) was added. The mixture was stirred overnight. The solvent was evaporated and co-evaporation with toluene was performed to assist the removal of TFA. The residue was dissolved in methanol (2 ml) and sodium borohydride (12.3 mg, 0.33 mmol) was added. After 15 minutes, ammonium acetate (17 mg) was added and the solvent was removed under reduced pressure. The residue was purified on preparative HPLC on C8 column. A gradient from 20% to 50% MeCN in 0.1M ammonium acetate buffer was used as eluent. After lyophilisation, the title compound was obtained as a white solid (15.1 mg, 77%). H-NMR (400 MHz, DMSO-$d_6$): 0.78 (d, 3H), 0.80 (d, 3H), 0.95-1.03 (m, 1H), 2.83-3.00 (m, 2H), 3.75-3.80 (m, 2H), 3.93-4-00 (t, 1H), 4.30 (d, 0.5H), 4.36-4.38 (brs, 0.5H), 4.52 (s, 2H), 4.69-4.77 (m, 1H), 5.02 (d, 0.5H), 5.06 (d, 0.5H), 6.96-7.00 (m, 2H), 7.18-7.22 (m, 2H), 7.31-7.38 (m, 8H), 7.60-7.74 (m, 1H), 8.28 (t, 1H). M/z: 671.9 (M+H).

Example 62

N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-D-lysine N-{[4-((2R,3R)-1-(4-Chlorophenyl)-3-{[2-(4-chlorophenyl)-2-oxoethyl]thio}-4-oxoazetidin-2-yl)phenoxy]acetyl}glycine (14.6 mg, 0.026 mmol) and N-methylmorpholine (20 µl, 0.18 mmol) were dissolved in DCM (2 ml). tert-Butyl ff-(tert-butoxycarbonyl)-D-lysinate hydrochloride (11.1 mg, 0.033 mmol) was added and after 5 minutes TBTU (9.8 mg, 0.031 mmol) was added to the suspension. The mixture was stirred overnight. Additional tert-butyl $N^6$-(tert-butoxycarbonyl)-D-lysinate (4.8 mg, 0.014 mmol), N-methylmorpholine (10 µl, 91 µmol) and TBTU (4.6 mg, 0.014 mmol) were added and the mixture was stirred for 2.5 h. The formation of the ester was confirmed. M/z: 855.4 (M–H). DCM (3 ml) and water (5 ml) were added and the solution was acidified to pH 3 with $KHSO_4$ (2M). The organic phase was washed with water (2×5 ml). The combined water phases were extracted with DCM (2×5 ml). The organic phase was dried over $Na_2SO_4$, filtered and concentrated under reduced pressure. The oily residue was dissolved in DCM (1.5 ml) and TFA (1 ml) was added. The mixture was stirred for 2.5 h. The mixture was concentrated and co-evaporation with toluene was performed to assist the removal of TFA. The residue was dissolved in methanol (2 ml) and sodium borohydride (10.4 mg, 0.027 mmol) was added. After 15 minutes, ammonium acetate buffer (0.1M, 1.5 ml) was added and the solvent was removed under reduced pressure. The residue was purified with preparative HPLC on a C8 column. A gradient from 20% to 50% MeCN in 0.1M ammonium acetate buffer was used as eluent. After lyophilisation, the title compound was obtained as a white solid (10.8 mg, 59%). H-NMR (400 MHz, DMSO-$d_6$): 1.18-1.36 (m, 2H), 1.41-1.70 (m, 4H), 2.71 (t, 2H), 2.84-2.97 (m, 2H), 3.72-3.75 (brd, 2H), 3.93 (m, 1H), 4.30 (d, 0.5H), 4.34 (d, 0.5H), 4.52 (s, 2H), 4.68-4.77 (m, 1H), 5.03 (d, 0.5H), 5.07 (d, 0.5H), 6.98 (d, 2H), 7.20 (d, 2H), 7.31-7.38 (m, 8H), 7.63-7.72 (m, 1H), 8.34 (t, 1H). M/z: 705.1.

Example 63

(2R)-2-[(N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl)amino]-4-phenylbutanoic acid N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (14.4 mg, 0.027 mmol) and N-methylmorpholine (15 µl, 0.14 mmol) were dissolved in DMF (3 ml). After 5 minutes, TBTU (10.3 mg, 0.032 mmol) was added and the mixture was stirred at 30° C. for 20 minutes. (2R)-2-Amino-4-phenylbutanoic acid (5.7 mg, 0.032 mmol) was added and the mixture was stirred at ambient temperature for 1.5 hors. The formation of the intermediate acid was confirmed. M/z: 702.0. MeOH (2.5 ml) and sodium borohydride were added and the mixture was stirred for 20 minutes. Ammonium acetate (31 mg) was added. The mixture was concentrated and purified with preparative HPLC on a C8 column. A gradient from 20% to 45% MeCN in 0.1M ammonium acetate buffer was used as eluent. After lyophilisation, the title compound was obtained as a white solid (9.4 mg, 50%). H-NMR (400 MHz, DMSO-$d_6$): 1.74-1.87 (m, 1H), 1.89-1.99 (m, 1H), 2.49-2.53 (m, 2H), 2.82-2.98 (m, 2H), 3.77 (d, 2H), 3.94-4.01 (m, 1H), 4.27 (d, 0.5H), 4.31 (d, 0.5M), 4.53 (s, 2H), 4.68-4.77 (m, 1H), 5.02 (d, 0.5H), 5.05 (d, 0.5H), 6.99 (d, 2H), 7.05-7.16 (m, 7H), 7.19-7.26 (m, 4H), 7.30-7.38 (m, 4H), 7.78-7.88 (dd, 1H), 8.35 (t, 1H). M/z: 702.0 (M−H).

Example 64

(2R)-2-[(N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl)amino]-4-(4-hydroxyphenyl)butanoic acid N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (15.2 mg, 0.028 mmol) and N-methylmorpholine (15 µl, 0.14 mmol) were dissolved in DMF (2 ml). TBTU (10.5 mg, 0.033 mmol) was added and after 20 minutes (2R)-2-amino-4-(4-hydroxyphenyl)butanoic acid hydrobromide (9.2 mg, 0.033 mmol) was added. The reaction mixture was stirred for 1.5 h. The formation of the intermediate acid was confirmed. M/z: 718.3. MeOH (2 ml) and sodium borohydride (10.7 mg, 0.28 mmol) were added and the mixture was stirred for 20 minutes. Ammonium acetate (34 mg) was added and the methanol was removed under reduced pressure. The residue was purified with preparative HPLC on a C8 column. A gradient from 20% to 45% MeCN in 0.1M ammonium acetate buffer was used as eluent. After lyophilisation, the title compound was obtained as a white solid (9.6 mg, 47%). H-NMR (400 MHz, DMSO-$d_6$): 1.75-1.86 (m, 1H), 1.89-1.98 (m, 1H), 2.41 (t, 2H), 2.81-2.98 (m, 2H), 3.78 (d, 2H), 3.97-4.05 (m, 1H), 4.27 (d, 0.5M), 4.31 (d, 0.5H), 4.53 (s, 2H), 4.67-4.76 (m, 1H), 5.02 (d, 0.5H), 5.05 (d, 0.5H), 6.62 (d, 2H), 6.91 (d, 2H), 6.98 (d, 2H), 7.05-7.16 (m, 4H), 7.20-7.25 (m, 2H), 7.30-7.39 (m, 4H), 7.87-7.97 (m, 1H), 8.30 (t, 1H), 8.91-9.30 (br, 1H). M/z: 718.0 (M−H).

Example 65

N-{[4-((2R,3R)-1-(4-fluorophenyl)-3-{[2-hydroxy-2-(4-methoxyphenyl)ethyl]thio}-4-oxoazetidin-2-yl)phenoxy]acetyl}glycyl-D-alanine N-{[4-((2R,3R)-1-(4-Fluorophenyl)-3-{[2-(4-methoxyphenyl)-2-oxoethyl]thio}-4-oxoazetidin-2-yl)phenoxy]acetyl}glycine (0.04 g, 0.072 mmol) and N-methylmorpholine (0.022 g, 0.217 mmol) were dissolved in $CH_2Cl_2$ (4 ml). tert-Butyl D-alaninate hydrochloride (0.016 g, 0.087 mmol) and TBTU (0.030 g, 0.094 mmol) were added. After 2 h, the reaction mixture was purified on silica gel and eluted with EtOAc/$CH_2Cl_2$ (25/75). Pure fractions were collected and concentrated. The residue was dissolved in $CH_2Cl_2$ (3 ml) and TFA (2 ml). The hydrolysis was completed after 2 h. The reaction mixture was concentrated and MeOH (3 ml) and $NABH_4$ (0.011 g, 0.290 mmol) were added. The mixture was stirred for 5 minutes. The reaction was quenched by the addition of 0.1M $NH_4OAc$ buffer (2 ml) and the solvent evaporated. The residue was purified by preparative HPLC using an eluent of 0-50% $CH_3CN$ in 0.1M $NH_4OAc$ buffer. Freeze-drying of the pure fractions afforded the title compound (0.030 g, 66%) as a colourless solid. M/z: 624.2, (M−1). $^1$H NMR [$(CD_3)_2SO$], 400 MHz] δ 1.16 (d, 3H), 2.83-2.93 (m, 2H), 3.68-3.74 (m, 5H), 3.88-3.95 (m, 1H), 4.23-4.26 (m, 1H), 4.51 (s, 2H), 4.60-4.70 (m, 1H), 5.00-5.03 (m, 1H), 6.81-7.37 (m, 12H), 7.74-7.79 (m, 1H), 8.29-8.34 (m, 1H).

Example 66

1-[(N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl)amino]cyclopropanecarboxylic acid N-Methyl morpholine (0.037 g, 0.370 mmol) and TBTU (0.039 g, 0.120 mmol) were added to a solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.025 g, 0.046 mmol) in DMF (2 ml) at 30° C. After 1 h, 1-aminocyclopropane carboxylic acid (0.019 g, 0.185 mmol) was added. After 1 h, the reaction was quenched by the addition of water (1 ml). After 10 minutes, MeOH (2 ml) and $NaBH_4$ (0.035 g, 0.925 mmol) were added. Full conversion to the corresponding alcohol was obtained after 5 minutes. The reaction was quenched by the addition of 0.1M $NH_4OAc$ buffer (2 ml). The product was purified by preparative HPLC (eluent 0-50% $CH_3CN$ in 0.1M $NH_4OAc$ buffer). Freeze-drying of the pure fractions afforded the title compound (0.045 g, 78%) as a colourless solid. $^1$H NMR [$(CD_3)_2SO$), 400 MH] δ 0.78-0.88 (m, 2H), 1.08-1.22 (m, 2H), 2.84-2.94 (m, 2H), 3.63-3.72 (m, 2H), 4.24-4.29 (m, 1H), 4.48-4.52 (m, 2H), 4.68-4.75 (m, 1H), 5.03-5.06 (m, 1H), 6.96-7.37 (m, 12H), 7.78-8.36 (m, 2H).

Example 67

N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-3-methyl-D-valine TBTU (0.020 g, 0.063 mmol) was added to a solution of N-{[4-((2R,3R)-1-(4-chlorophenyl)-3-{[2-(4-chlorophenyl)-2-oxoethyl]thio}-4-oxoazetidin-2-yl)phenoxy]acetyl}glycine (0.030 g, 0.052 mmol) and N-methylmorpholine (0.016 g, 0.157 mmol) in $CH_2Cl_2$ (5 ml) at 30° C. After 30 minutes, D-tert-leucine (0.008 g, 0.063 mmol) was added and the mixture was stirred for 30 minutes. The reaction mixture was concentrated. Toluene (2 ml) was added and evaporated. MeOH (3 ml) and sodium borohydride (0.020 g, 0.523 mmol) were added. Full conversion to the corresponding alcohol was obtained after 5 minutes. The reaction was quenched by the addition of 0.1M $NH_4OAc$ (1 ml) buffer and the mixture was concentrated. The residue was purified by preparative HPLC using an eluent of 0-50% $CH_3CN$ in 0.1M $NH_4OAc$ buffer. Freeze-drying of the pure fractions afforded the title compound (0.021 g, 58%) as a colourless solid. $^1$H NMR [$(CD_3)_2SO$), 400 MHz] δ 0.85 (s, 9H), 2.82-2.98 (m, 2H), 3.75-3.81 (m, 2H), 3.91-3.96 (m, 1H), 4.29-4.37 (m, 1H), 4.52 (s, 2H), 4.70-4.78 (m, 1H), 5.01-5.06 (m, 1H), 6.97-6.99 (m, 2H), 7.19-7.21 (m, 2H), 7.32-7.36 (m, 8H), 7.52-7.63 (m, 1H), 8.27-8.32 (m, 1H).

Example 68

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-tryptophan TBTU (0.016 g, 0.051 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.025 g, 0.046 mmol) and N-methylmorpholine (0.014 g, 0.139 mmol) in DMF (2 ml) at 30° C. After 1 h, DMSO (1 ml) and D-tryptophan (0.019 g, 0.092 mmol) were added. After 10 minutes, the reaction was quenched by the addition of water (1 ml). The mixture was stirred for 10 minutes and MeOH (1 ml) and NaBH$_4$ (0.035 g, 0.925 mmol) were added. After 5 minutes, full conversion to the corresponding alcohol was obtained. The reaction was quenched by the addition of 0.1M NH$_4$OAc buffer (1 ml). The reaction mixture was concentrated and the residue was purified by preparative HPLC using an eluent of 0-50% CH$_3$CN in 0.1M NH$_4$OAc buffer. This gave the title compound (0.028 g, 83%) as a colourless solid. M/z: 727.0 (M−1). $^1$H NMR [(CD$_3$)$_2$SO], 400 MHz] δ 2.79-3.18 (m, 4H), 3.61-3.80 (m, 2H), 4.26-4.34 (m, 2H), 4.43-4.54 (m, 2H), 4.68-4.78 (m, 1H), 4.97-5.04 (m, 1H), 6.84-7.55 (m, 1H), 7.65-7.82 (m, 1H), 8.22-8.25 (m, 1H), 10.73 (s, 1H).

Example 69

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-D-histidine TBTU (0.016 g, 0.051 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy] acetyl}glycine (0.025 g, 0.046 mmol) and N-methylmorpholine (0.014 g, 0.139 mmol) in DMF (2 ml) at 30° C. After 1 h, D-histidine (0.014 g, 0.092 mmol) and tetrabutylammoniumbromide (0.003 g, 0.009 mmol) were added. The reaction mixture was stirred overnight (30% conversion) and the reaction was quenched by the addition of water (2 ml). Purification by preparative HPLC using an eluent of 0-50% CH$_3$CN in 0.1M NH$_4$OAc buffer afforded the intermediate ketone, which was reduced by the addition of MeOH (3 ml) and NaBH$_4$ (0.005 g, 0.139 mmol). Full conversion to the corresponding alcohol was obtained after 5 minutes. The reaction was quenched by the addition of 0.1M NH$_4$OAc buffer (2 ml) and the mixture was concentrated. Purification by preparative HPLC using an eluent of 040% CH$_3$CN in 0.1M NH$_4$OAc buffer afforded the title compound (0.001 g, 4.5%) as a colourless solid. M/z: 680.0. $^1$H NMR [(CD$_3$)$_2$SO], 400 MHz] δ 2.82-2.93 (m, 4H), 3.71-3.80 (m, 2H), 4.11-4.30 (m, 2H), 4.52 (s, 2H), 4.68-4.73 (m, 1H), 5.04-5.07 (m, 1H), 6.68-7.50 (m, 1H), 7.90-7.96 (m, 1H), 8.27-8.33 (m, 1H).

Example 70

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-3-(2-naphthyl)-D-alanine TBTU (0.019 g, 0.060 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy] acetyl}glycine (0.025 g, 0.046 mmol) and N-methylmorpholine (0.014 g, 0.139 mmol) in CH$_2$Cl$_2$ (5 ml) at 30° C. After 1 h, DMF (3 ml), DMSO (1 ml) and D-(2-naphtyl)alanine (0.011 g, 0.051 mmol) were added. The reaction was quenched by the addition of water (1 ml) after 1 h. NaBH$_4$ (0.035 g, 0.925 mmol) was added. After 5 minutes, full conversion to the corresponding alcohol was obtained. The reaction was quenched by the addition of 0.1M NH$_4$OAc buffer (1 ml) and the mixture was concentrated. Purification by preparative HPLC using an eluent of 0-55% CH$_3$CN in 0.1M NH$_4$OAc buffer afforded the title compound (0.017 g, 48%) as a colourless solid. M/z: 738.0 (M−1). $^1$H NMR [(CD$_3$)$_2$SO], 400 MHz] δ 2.75-3.27 (m, 4H), 3.55-3.83 (m, 2H), 4.25-4.55 (m, 4H), 4.68-4.79 (m, 1H), 4.92-5.02 (m, 1H), 6.72-7.80 (m, 20H), 8.26-8.30 (m, 1H).

Example 71

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-3-methyl-D-valine TBTU (0.021 g, 0.067 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy] acetyl}glycine (0.030 g, 0.056 mmol) and N-methyl morpholine (0.017 g, 0.166 mmol) in CH$_2$Cl$_2$ (5 ml) at 30° C. After 1.5 h, D-tert-leucine (0.011 g, 0.083 mmol) was added. Full conversion to the corresponding amide was obtained after 30 minutes. The reaction was quenched by the addition of water (1 ml). After 10 minutes, MeOH (3 ml) and NaBH (0.042 g, 1.11 mmol) were added. After 5 minutes, the reaction was quenched by the addition of 0.1M NH$_4$OAc buffer (1 ml). The reaction mixture was concentrated and purified by preparative HPLC using an eluent of 0-50% CH$_3$CN in 0.1M N$_4$OAc buffer. The title compound (0.025 g, 69%) was obtained as a colourless solid. M/z: 654.0 (M−1). $^1$H NMR [(CD$_3$)$_2$SO], 400 MHz] δ 0.86 (s, 9H), 2.82-2.98 (m, 2H), 3.76-3.81 (m, 2H), 3.92-3.96 (m, 1H), 4.26-4.33 (m, 1H), 4.52 (s, 2H), 4.68-4.76 (m, 1H), 5.02-5.07 (m, 1H), 6.97-7.37 (m, 12H), 7.58-7.63 (m, 1H), 8.29-8.34 (m, 1H).

Example 72

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-(3R,4S,5R)-3,4,5,6-tetrahydroxy-D-norleucine N-{[4-((2R,3R)-1-(4-Fluorophenyl)-3-{[2-(4-fluorophenyl)-2-oxoethyl]thio}-4-oxoazetidin-2-yl)phenoxy] acetyl}glycine (0.025 g, 0.046 mmol) was dissolved in DMSO (2 ml) at 30° C. N-Methylmorpholine (0.014 g, 0.139 mmol) and TBTU (0.018 g, 0.056 mmol) were added. After 1 h, d-glucosaminic acid (0.018 g, 0.092 mmol) and tetrabutylammoniumbromide (0.001 g, 0.005 mmol) were added. The mixture was stirred for 15 minutes. Additional TBTU (18 mg, 0.056 mmol) was added. After 30 minutes, approximately 30% amide formation had occurred. The reaction was quenched by the addition of 0.1M NH$_4$OAc buffer (2 ml). The intermediate ketone was purified by preparative HPLC using an eluent of 0-50% CH$_3$CN in 0.1M NH$_4$OAc buffer and freeze-dried. MeOH (3 ml) and NABH$_4$ (0.005 g, 0.139 mmol) were added. After 5 minutes, the reaction was quenched by the addition of 0.1M NH$_4$OAc buffer (1 ml). Concentration of the mixture and purification by preparative HPLC using an eluent of 0-50% CH$_3$CN in 0.1M NH$_4$OAc buffer gave the title compound (0.005 g, 16%) as a colourless solid. M/z: 718.0 (M−1). $^1$H NMR [(CD$_3$)$_2$SO], 400 MHz] δ 2.82-2.94 (m, 2H), 3.34-3.56 (m, 4H), 3.76-3.80 (m, 2H), 3.87-3.90 (m, 1H), 4.07-4.11 (m, 1H), 4.27-4.32 (m, 1H), 4.52 (s, 2H), 4.68-4.76 (m, 1H), 5.02-5.05 (m, 1H), 6.97-7.39 (m, 12H), 7.63-7.70 (m, 1H), 8.28-8.35 (m, 1H).

Example 73

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-β-phenyl-D-phenylalanine TBTU (0.018 g, 0.056 mmol) was added to a solution of N-{[4-((2R,3R)-1-(4-fluorophenyl)-3-{[2-(4-fluorophenyl)-2-oxoethyl]thio}-4-oxoazetidin-2-yl)phenoxy] acetyl}glycine (0.025 g, 0.046 mmol) and N-methylmorpholine (0.023 g, 0.231 mmol) in CH$_2$Cl$_2$ (5 ml) at 30° C. After 1.5 h, β-phenyl-D-phenylalanine trifluoro acetic acid salt (0.033 g, 0.092 mmol) was added. The mixture was stirred for 5 minutes. Water (1 ml) was added and the mixture was concentrated. MeOH (3 ml) and $NaBH_4$ (0.017 g, 0.462 mmol) were added. After 5 minutes, the reaction was quenched by the addition of 0.1M $NH_4OAc$ buffer (1 ml) followed by concentration of the mixture. Purification by preparative HPLC using an eluent of 0-45% $CH_3CN$ in 0.1M $NH_4OAc$ buffer and lyophilisation gave the title compound (0.021 g, 59%) as a colourless solid. M/z: 764.1 (M−1). $^1$H NMR [$(CD_3)_2SO$], 400 MHz] δ 2.82-2.95 (m, 2H), 3.42-3.49 (m, 1H), 3.66-3.74 (m, 1H), 4.25-4.33 (m, 2H), 4.42 (d, 1H), 4.47 (d, 1H), 4.69-4.76 (m, 1H), 5.03-5.12 (m, 2H), 6.94-7.38 (m, 2H), 8.10-8.14 (m, 1H), 8.18-8.24 (m, 1H).

Example 74

(2R)-4-cyclohexyl-2-[(N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl)amino]butanoic acid N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.025 g, 0.046 mmol) was dissolved in DMF (2 ml) at 30° C. N-Methyl morpholine (0.034 g, 0.333 mmol) and TBTU (0.043 g, 0.133 mmol) were added. After 1 h, sodium (2R)-2-amino-4-cyclohexylbutanoate (0.039 g, 0.189 mmol), DMSO (2 ml) and tetrabutylammoniumbromide (0.004 g, 0.011 mmol) were added. The mixture was stirred for 1 h and water (1 ml) was added. After 1 h, MeOH (2 ml) and $NaBH_4$ (0.084 g, 2.220 mmol) were added. Full conversion to the corresponding alcohol was obtained after 5 minutes. The reaction was quenched by the addition of 0.1M $NH_4OAc$ buffer (2 ml). The mixture was purified by preparative HPLC (eluent 0-50% $CH_3CN$ in 0.1M $NH_4OAc$ buffer). Freeze-drying of the pure fractions gave the title compound (0.034 g, 43%) as a colourless solid. M/z: 708.1 (M−1). $^1$H NMR [$(CD_3)_2SO$], 400 MHz] δ 0.75-1.62 (m, 15H), 2.82-2.99 (m, 2H), 3.68-3.78 (m, 2H), 3.90-3.96 (m, 1H), 4.23-4.35 (m, 1H), 4.50 (s, 2H), 4.69-4.75 (m, 1H), 5.01-5.07 (m, 1H), 6.95-7.39 (m, 12H), 7.68-7.80 (m, 1H), 8.20-8.34 (m, 1H).

Example 75

(2R)-cyclopentyl[(N-{[4-((2R,3R)-1 (4-fluorophenyl)-3-{[2-(4-fluorophenyl)-2-hydroxyethyl]thio}-4-oxoazetidin-2-yl)phenoxy]acetyl}glycyl)amino]acetic acid N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (0.035 g, 0.065 mmol) was dissolved in DMF (2 ml) at 30° C. N-Methyl morpholine (0.026 g, 0.259 mmol) and TBTU (0.027 g, 0.084 mmol) were added. After 1 h, (2R)-amino(cyclopentyl)acetic acid (0.014 g, 0.097 mmol) was added. The mixture was stirred for 1 h and water (1 ml) was added. After 10 minutes, MeOH (2 ml) and $NaBH_4$ (0.037 g, 0.971 mmol) were added. Full conversion to the corresponding alcohol was obtained after 5 minutes. The reaction was quenched by the addition of 0.1M $NH_4OAc$ buffer (2 ml). The mixture was purified by preparative HPLC (eluent 0-50% $CH_3CN$ in 0.1M $NH_4OAc$ buffer). Freeze-drying of the pure fractions gave the title compound (0.018 g, 42%) as a colourless solid. M/z: 666.0 (M−1). $^1$H NMR [$(CD_3)_2SO$], 400 M] δ 1.19-1.62 (m, 8H), 2.09-2.19 (m, 1H), 2.83-2.95 (m, 2H), 3.78 (d, 2H), 4.06-4.10 (m, 1H), 4.25-4.30 (m, 1H), 4.51 (s, 2H), 4.68-4.75 (m, 1H), 5.03-5.06 (m, 1H), 6.97-7.37 (m, 12H), 7.95-8.00 (m, 1H), 8.22 (t, 1H).

Example 76

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-methyl-D-isovaline N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (0.035 g, 0.065 mmol) was dissolved in DMF (2 ml) at 30° C. N-Methyl morpholine (0.026 g, 0.259 mmol) and TBTU (0.027 g, 0.084 mmol) were added. After 1 h, 3-methyl-D-isovaline (0.013 g, 0.097 mmol) was added. The mixture was stirred for 2 h and water (1 ml) was added. After 10 minutes, MeOH (2 ml) and $NaBH_4$ (0.037 g, 0.971 mmol) were added. Full conversion to the corresponding alcohol was obtained after 5 minutes and 0.1M $NH_4OAc$ buffer (2 ml) was added. The mixture was purified by preparative HPLC (eluent 0-50% $CH_3CN$ in 0.1M $NH_4OAc$ buffer). Freeze-drying of the pure fractions afforded the title compound (0.020 g, 47%) as a colourless solid. M/z: 654.0 (M−1). $^1$H NMR [$(CD_3)_2SO$], 400 MHz] δ 0.79 (d, 3H), 0.87 (d, 3H), 1.29 (s, 3H), 2.00-2.07 (m, 1H), 2.84-2.94 (m, 2H), 3.73 (d, 2H), 4.25-4.28 (m, 1H), 4.51 (s, 2H), 4.69-4.75 (m, 1H), 5.03-5.06 (m, 1H), 6.97-7.37 (m, 12H), 7.82 (s, 1H), 8.24 (t, 1H).

Example 77

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(tert-butyl)-D-cysteine N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (20 mg, 0.037 mmol) and N-methylmorpholine (20 μl, 0.18 mmol) were dissolved in DMF (3 ml). TBTU (14.6 mg, 0.046 mmol) was added and the mixture was stirred at 30° C. for 45 minutes. S-(tert-Butyl)-D-cysteine hydrochloride (9.7 mg, 0.045 mmol) was added and the reaction mixture was stirred for 1.5 h. The formation of the ketone of the title compound was confirmed. M/z: 700.0. Methanol (2 ml) and sodium borohydride (14.3 mg, 0.38 mmol) were added and the mixture was stirred for 30 minutes. Ammonium acetate buffer (0.1M, 2 ml) was added and the mixture was concentrated. The residue was purified with preparative HPLC on a C8 column. A gradient from 20% to 45% MeCN in 0.1M $N_4OAc$ buffer was used as eluent. The MeCN was removed from the collected fraction under reduced pressure. The remaining water solution was acidified to pH 1 with HCl (1M) and extracted with DCM. The organic phase was concentrated under reduced pressure and the residue was dissolved in MeCN and water. After lyophilisation, the title compound was obtained as a white solid (16.5 mg, 65%). H-NMR (400 MHz, DMSO-$d_6$): 1.21 (s, 9H), 2.71-2.78 (m, 1H), 2.82-2.86 (m, 3H), 2.74-2.80 (m, 2H), 2.18-2.26 (m, 1H), 4.27 (d, 0.5H), 4.30 (d, 0.5H), 4.51 (s, 2H), 2.67-2.76 (m, 1H), 5.03 (d, 0.5H), 5.05 (d, 0.5), 6.98 (d, 2H), 7.05-7.17 (m, 4H), 7.20-7.25 (m, 2H), 7.30-7.39 (m, 4H), 7.94-8.06 (b, 1H), 8.26 (t, 1H). M/z: 700.0 (M−H) and 702.1 (M+H).

Example 78

N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl-N,2-dimethylalanine To mixture of N-{[4-((2R,3R)-1-(4-fluorophenyl)-3-{[2-(4-fluorophenyl)-2-oxoethyl]thio}-4-oxoazetidin-2-yl)phenoxy]acetyl}glycine (0.020 g, 0.037 mmol) and NMM (0.012 ml, 0.109 mmol) in DMF (3 ml) at 30° C. was added TBTU (0.018 g, 0.056 mmol). The reaction mixture was stirred for 20 min after which 2-(methylamino)isobutyric acid (0.005 g, 0.038 mmol) was added. The mixture was stirred at 30° C. for 20 h before the reaction was quenched by the addition of water (1 ml). The mixture was diluted with MeOH (2 ml) and NaBH4(0.018 g, 0.486 mmol) was added. After 10 min the reaction was quenched by the addition of a 0.1M ammonium acetate buffer (2 ml) and most of the methanol was removed under reduced pressure. The remaining solution was purified by preparative HPLC using a gradient of 20-50% MeCN in a 0.1M ammonium acetate buffer as eluent. Freeze-drying of the pure fractions gave the desired product as a white solid (0.012 g, 50% yield).

Accurate mass: 642.211 (M+1)$^+$

Example 79

(2R)-3-(4-cyanophenyl)-2-{[({[4-((2R,3R)-1-(4-fluorophenyl)-3-{[2-(4-fluorophenyl)-2-hydroxyethyl]thio}-4-oxoazetidin-2-yl)phenoxy]acetyl}amino)acetyl]amino}propanoic acid (2R)-3-(4-cyanophenyl)-2-{[({[4-((2R,3R)-1-(4-fluorophenyl)-3-{[2-(4-fluorophenyl)-2-oxoethyl]thio}-4-oxoazetidin-2-yl)phenoxy]acetyl}amino}acetyl]amino)propanoic acid (0.006 g, 0.0084 mmole) was dissolved in methanol (1.5 ml). NaBH$_4$ (0.0035 g, 0.092 mmole) was added and when the reaction was complete according to LC-MS a few drops of acetic acid was added. The solvent was removed under reduced pressure and the residue was purified by preparative HPLC on a Kromasil C8-column using a stepwise gradient of 33.5%, 43% and then 55.5% MeCN in 0.1M ammonium acetate buffer as eluent. After freeze-drying, 0.005 g (83%) of the desired product was obtained.

NMR (500 MHz,CD$_3$COOD) 2.91-3.12 (m, 3H), 3.26-3.32 (m, 1H), 3.91 (ABq, 2H), 4.03-4.07 (m, 1H), 4.57 (s, 2H), 4.65 (brt, 1H), 4.80-4.85 (m, 1H), 4.90-4.93 (m, 1H), 6.97-7.08 (m, 6H), 7.26-7.32 (m, 2H), 7.32-7.41 (m, 6H), 7.60 (d, 2H)

Example 80

N-{[4-((2R,3R)-1-(4-Fluorophenyl)-3-{[2-hydroxy-2-(4-pentylphenyl)ethyl]thio}-4-oxoazetidin-2-yl)phenoxy]acetyl}glycyl-3-cyclohexyl-D-alanine To a solution of [4-((2R,3R)-1-(4-fluorophenyl)-4-oxo-3-{[2-oxo-2-(4-pentylphenyl)ethyl]thio}azetidin-2-yl)phenoxy]acetic acid (0.020 g, 0.037 mmol) and NMM (0.012 ml, 0.109 mmol) in DMF (2 ml) at 30° C. was added TBTU (0.019 g, 0.059 mmol). After 15 min glycyl-3-cyclohexyl-D-alanine (0.009 g, 0.039 mmol) was added and the mixture was stirred at 30° C. for 22 h. The reaction was quenched by the addition of water (1 ml) before the mixture was diluted with MeOH (2 ml). To this solution was added NaBH4 (0.020 g, 0.529 mmol) and the mixture was stirred for 10 min. This reaction was quenched by the addition of a 0.1M ammonium acetate buffer (3 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product as a white solid (0.009 g, 32% yield).

1H NMR (CD$_3$OD, 400 MHz) δ: 0.82-1.03 (m, 5H), 1.10-1.45 (m, 8H), 1.48-1.74 (m, 8H), 1.75-1.85 (m, 1H), 2.51-2.60 (m, 2H), 2.89-3.08 (m, 2H), 3.91-4.04 (m, 3H), 4.42-4.49 (m, 1H), 4.56-4.60 (m, 2H), 4.71-4.87 (m, 2l), 6.95-7.10 (m, 6H), 7.18-7.35 (m, 6H).

Example 81

N-({4-[(2R,3R)-1-(4-Fluorophenyl)-3-({2-hydroxy-2-[4-(methylthio)phenyl]ethyl}thio)-4-oxoazetidin-2-yl]phenoxy}acetyl)glycyl-3-cyclohexyl-D-alanine To a solution of {4-[(2R,3R)-1-(4-fluorophenyl)-3-({2-hydroxy-2-[4-(methylthio)phenyl]ethyl}thio)-4-oxoazetidin-2-yl]phenoxy}acetic acid (0.020 g, 0.039 mmol) and NMM (0.025 ml, 0.227 mmol) in DMF (3 ml) at RT was added TBTU (0.025 g, 0.078 mmol). The reaction mixture was stirred for 90 min after which glycyl-3-cyclohexyl-D-alanine (0.010 g, 0.044 mmol) was added. The mixture was stirred for 22 h before the reaction was quenched by the addition of water (1 ml). The mixture was diluted with MeOH (1 ml) and then NaBH4 (0.016 g, 0.423 mmol) was added. After 10 min the reaction was quenched by the addition of a 0.1M ammonium acetate buffer (2 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product as a white solid (0.009 g, 32% yield).

ES− m/z: 723.1 (M−1)$^-$. 1H NMR (DMSO, 500 MHz) δ: 0.75-0.95 (m, 2H), 1.05-1.35 (m, 4H), 1.42-1.72 (m, 7H), 2.43-2.47 (m, 3H), 2.85-2.97 (m, 2H), 4.15-4.23 (m, 1H), 4.26-4.32 (m, 1H), 4.53 (s, 2H), 4.65-4.74 (m, 1H), 5.01-5.07 (m, 1H), 5.66 (bs, 1H), 6.97-7.03 (m, 2H), 7.13-7.29 (m, 8H), 7.35-7.41 (m, 2H), 7.96-8.06 (m, 1H), 8.22-8.29 (m, 1H).

Example 82

N-({4-[(2R,3R)-1-(4-Fluorophenyl)-3-({2-hydroxy-2-[4-(methylthio)phenyl]ethyl}thio)-4-oxoazetidin-2-yl]phenoxy}acetyl)glycyl-D-valine A solution of {4-[(2R,3R)-1-(4-fluorophenyl)-3-({2-hydroxy-2-[4-(methylthio)phenyl]ethyl}thio)-4-oxoazetidin-2-yl]phenoxy}acetic acid (0.015 g, 0.029 mmol), tert-butyl glycyl-D-valinate hydrochloride (0.009 g, 0.034 mmol) and N-Methylmorpholine (0.013 ml, 0.118 mmol) in DCM (3 ml) was stirred at RT for 10 min, after which TBTU (0.014 g, 0.044 mmol) was added. After 17 h the conversion to the intermediate (m/z: 724.7, M+1) was completed. The solution was diluted with TFA (2 ml) and the mixture was allowed to stir for 2 h. The resulting acid (m/z: 668.6, M+1) was concentrated and the residue was dissolved in MeOH (3 ml). To this solution was added NaBH4 (80 mg, 2.11 mmol) in portions until the reduction of the ketone was completed (LC/MS). The reaction was quenched by the addition of a 0.1M ammonium acetate buffer (3 ml) before most of the methanol was removed under reduced pressure. The remaining solution was purified by preparative HPLC, using a gradient of 20-50% MeCN in a 0.1M ammonium acetate buffer as eluent.

Freeze-drying of the pure fractions gave the desired product (0.014 g, 70%) as a white solid.

ES– m/z: 669.0 (M–1)⁻. 1H NMR (CD3OD, 400 MHz) δ: 0.88-0.98 (m, 6H), 2.10-2.23 (m, 1H), 2.40-2.47 (m, 3H), 2.89-3.08 (m, 2H), 3.93-4.06 (m, 3H), 4.31 (d, 1H), 4.59 (s, 2H), 4.73-4.84 (m, 2H), 6.95-7.07 (m, 4H), 7.13-7.18 (m, 2H), 7.21-7.34 (m, 6H).

Example 83

N-({4-[(2R,3R)-1-(4-fluorophenyl)-3-({2-hydroxy-2-[4-(methylthio)phenyl]ethyl}thio)-4-oxoazetidin-2-yl]phenoxy}acetyl)glycyl-3-methyl-D-valine To a solution of {4-[(2R,3R)-1-(4-fluorophenyl)-3-({2-hydroxy-2-[4-(methylthio)phenyl]ethyl}thio)-4-oxoazetidin-2-yl]phenoxy}acetic acid (0.020 g, 0.039 mmol) and NMM (0.020 ml, 0.182 mmol) in DMF (3 ml) at RT was added TBTU (0.020 g, 0.062 mmol). The reaction mixture was stirred for 60 min after which glycyl-3-methyl-D-valine (0.008 g, 0.043 mmol) was added. The mixture was stirred for 18 h before the reaction was quenched by the addition of water (1 ml). The mixture was diluted with MeOH (1 ml) and NaBH4 (0.040 g, 1.06 mmol) was added. After 10 min the reaction was quenched by the addition of a 0.1M ammonium acetate buffer (2 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product as a white solid (0.006 g, 22% yield).

ES– m/z: 683.0 (M–1)⁻. 1H NR (DMSO, 500 MHz) δ: 0.88-0.94 (m, 9H), 2.44-2.46 (m, 3H), 2.85-2.98 (m, 2H), 3.80-3.87 (m, 2H), 4.01-4.07 (m, 1H), 4.27-4.35 (m, 1H), 4.55 (s, 2H), 4.66-4.75 (m, 1H), 5.01-5.07 (m, 1H), 6.97-7.03 (m, 2H), 7.14-7.29 (m, 8H), 7.36-7.41 (m, 2H), 7.70-7.85 (m, 1H), 8.28-8.33 (m, 1H).

Example 84

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-4-methyl-D-leucine N-{[4-((2R,3R)-1-(4-Fluorophenyl)-3-{[2-(4-fluorophenyl)-2-oxoethyl]thio}-4-oxoazetidin-2-yl)phenoxy] acetyl}glycine (20 mg, 0.037 mmol) was dissolved in 1.5 ml DMF. N-Methylmorpholine (13 µl, 118 mmol) and TBTU (15 mg, 0.047 mmol) were added and the mixture was stirred for 1 h., β-tert-Butyl-D-alanine (11 mg, 0.076 mmol) was added and the mixture was stirred for 3 h. Water (0.2 ml) was added and the mixture was stirred for 15 min. MeOH (2 ml) and NaBH4 (15 mg) were added. NH4Ac (ca 20 mg) was added after 15 min. Purification was performed using preparative HPLC on a C8 column. A gradient from 20-50% MeCN in 0.1M NH4Ac was used as mobile phase. Lyophilization yielded 17.5 mg (70%) of the title compound. M/z: 668 (M–1). NMR (400 MHz, DMSO): 8.24 (t, 1H), 7.77-7.87 (m, 1H), 7.32-7.40 (m, 4H), 7.22-7.27 (m, 2H), 7.07-7.19 (m, 4H), 6.99 (d, 2H), 5.06 (dd, 1H), 4.70-4.78 (m, 1H), 4.53 (s, 2H), 4.31 (dd, 1H), 4.09-4.17 (m, 2H), 3.65-3.81 (m, 2H), 2.84-3.00 (m, 2H), 1.65 (dd, 1H), 1.42 (dd, 1H), 0.86 (s, 9H).

Example 85

N-{[4-((2R,3R)-1-(4-fluorophenyl)-3-{[2-(4-fluorophenyl)-2-hydroxyethyl]thio}-4-oxoazetidin-2-yl) phenoxy]acetyl}glycyl-3-cyclopentyl-D-alanine To a solution of N-{[4-((2R,3R)-1-(4-fluorophenyl)-3-{[2-(4-fluorophenyl)-2-oxoethyl]thio}-4-oxoazetidin-2-yl) phenoxy]acetyl}glycine (0.05 g, 0.092 mmol) and N-methyl morpholine (0.037 g, 0.37 mmol) in DMF (2 ml), under an atmosphere of nitrogen, was added TBTU (0.039 g, 0.12 mmol). After 1.5 h, 3-cyclopentyl-D-alanine (0.022 g, 0.139 mmol) was added. The reaction was allowed to stir for 1 h after which water (1 ml) was added. After 10 minutes, MeOH (2 ml) and NaBH4 (0.035 g, 0.925 mmol) were added. Full conversion to the corresponding alcohol was achieved within 5 minutes. The reaction was quenched by the addition of 0.1M NH4OAc buffer (2 ml) and the product was isolated by preparative HPLC of the mixture (eluent 0-50% CH3CN in 0.1M NH4OAc buffer). Freeze drying of pure fractions afforded the desired compound (0.031 g, 49%) as a colourless solid. m/z: 680.7 (M–1). ¹H NMR [(CD3)2SO), 400 MHz] δ 0.97-1.10 (m, 2H), 1.38-1.81 (m, 9H), 2.84-2.94 (m, 2H), 3.77 (d, 2H), 4.11-4.16 (m, 1H), 4.25-4.28 (m, 1H), 4.51 (s, 2H), 4.69-4.75 (m, 1H), 5.03-5.06 (m, 1H), 6.97-7.37 (m, 12H), 8.02-8.06 (m, 1H), 8.22 (t, 1H).

Example 86

N-{[4-((2R,3R)-1-(4-fluorophenyl)-3-{[2-hydroxy-2-(4-methoxyphenyl)ethyl]thio}-4-oxoazetidin-2-yl) phenoxy]acetyl}glycyl-3-methyl-D-valine To a solution of [4-((2R,3R)-1-(4-fluorophenyl)-3-{[2-(4-methoxyphenyl)-2-oxoethyl]thio}-4-oxoazetidin-2-yl)phenoxy]acetic acid (0.04 g, 0.081 mmol) and N-methyl morpholine (0.033 g, 0.323 mmol) in DMF (2 ml), under an atmosphere of nitrogen, was added TBTU (0.034 g, 0.105 mmol). After 1.5 h, glycyl-3-methyl-D-valine trifluoroacetate salt (0.037 g, 0.121 mmol) was added. The mixture was allowed to stir for 1 h after which water (1 ml) was added. After 10 minutes, MeOH (2 ml) and NaBH4 (0.031 g, 0.807 mmol) were added. Full conversion to the corresponding alcohol was achieved within 5 minutes. The reaction was quenched by the addition of 0.1M NH14OAc buffer (2 ml) and the product was isolated by preparative HPLC of the mixture (eluent 0-50% CH3CN in 0.1M NH4OAc buffer). Freeze drying of pure fractions afforded the desired compound (0.027 g, 50%) as a colourless solid. m/z: 666.7 (M–1). ¹H NMR [(CD3)2SO), 400 Mz] δ 0.88 (s, 9H), 2.81-2.93 (m, 2H), 3.69-3.70 (m, 3H), 3.82 (d, 2H), 4.03-4.07 (m, 1H), 4.22-4.25 (m, 1H), 4.51 (s, 2H), 4.61-4.68 (m, 1H), 5.01-5.03 (m, 1H), 6.81-7.36 (m, 12H), 7.81-7.86 (m, 1H), 8.25 (t, 1H).

Example 87

N-({4-[(2R,3R)-3-{[2-(4-ethoxyphenyl)-2-hydroxyethyl]thio}-1-(4-fluorophenyl)-4-oxoazetidin-2-yl] phenoxy}acetyl)glycyl-3-methyl-D-valine To a solution of {4-[(2R,3R)-3-{[2-(4-ethoxyphenyl)-2-oxoethyl]thio}-1-(4-fluorophenyl)-4-oxoazetidin-2-yl] phenoxy}acetic acid (0.04 g, 0.078 mmol) and N-methyl morpholine (0.032 g, 0.314 mmol) in DMF (2 ml) under an atmosphere of nitrogen was added TBTU (0.033 g, 0.102 mmol). After 45 minutes, glycyl-3-methyl-D-valine trifluoroacetate salt (0.031 g, 0.102 mmol) was added. The mixture was allowed to stir for 15 minutes after which water (1 ml) was added. After 10 minutes, MeOH (2 ml) and NaBH$_4$ (0.030 g, 0.785 mmol) were added. Full conversion to the corresponding alcohol was achieved within 5 minutes. The reaction was quenched by the addition of 0.1M NH$_4$OAc buffer (2 ml) and the product was isolated by preparative HPLC of the mixture (eluent 0-50% CH$_3$CN in 0.1M NH$_4$OAc buffer). Freeze drying of pure fractions afforded the desired compound (0.027 g, 50%) as a colourless solid. m/z: 680.8 (M−1). $^1$H NMR [(CD$_3$)$_2$SO), 400 MHz] δ 0.89 (s, 9H), 1.26-1.30 (m, 3H), 2.81-2.92 (m, 2H), 3.82 (d, 2H), 3.93-3.99 (m, 2H), 4.05-4.08 (m, 1H), 4.22-4.25 (m, 1H), 4.51 (s, 2H), 4.60-4.67 (m, 1H), 5.01-5.03 (m, 1H), 6.79-7.36 (m, 12H), 7.82-7.87 (m, 1H), 8.25 (t, 1H).

Example 88

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(4-methoxybenzyl)-D-cystein To a stirred solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine, (21.3 mg, 0.039 mmol) in DMF (3 ml) was added N-methylmorpholine (20μl, 0.18 mmol). TBTU (15.1 mg, 0.047 mmol) was added and the mixture was stirred at 30° C. for 35 minutes. S-(4-methoxybenzyl)-D-cysteine (12.8 mg, 0.053 mmol) was added and the mixture was stirred 1 hour at 30° C. and 1.5 hours at ambient temperature. The formation of the ketone of the title compound was confirmed. M/z: 764.11 (M+1) and 762.06 (M−1). Methanol (3 ml) and sodium borohydride (15 mg, 0.40 mmol) were added and the mixture was stirred for 20 minutes. Ammonium acetate (25 mg) was added and the methanol was removed under reduced pressure. The remaining DMF-solution was purified with preparative HPLC on a C8 column, UV 240/260 nm. A gradient from 20 to 47% MeCN in 0.1M NH$_4$OAc was used as eluent. The MeCN was removed from the collected fractions under reduced pressure. The remaining water solution was acidified to pH 1 with KHSO$_4$ (2M) and extracted with DCM. The organic phase was concentrated under reduced pressure and the residue was dissolved in MeCN and water. After lyophilisation, the title compound was obtained as a white solid (10.7 mg, 36%). H-NMR (400 MHz, DMSO-d$_6$): 2-60-2.80 (m, 2H), 2.83-2.97 (m, 2H), 3.63-3.66 (bd, 2H), 3.69 (s, 3H), 3.77-3.81 (bd, 2H), 4.24-4.33 (m, 2H), 4.52 (s, 2H), 4.67-4.76 (m, 1H), 5.03 (d, 0.5H), 5.06 (d, 0.5H), 5.60-5.90 (b, 1H), 6.82 (d, 2H), 6.98 (d, 2H), 7.05-7.25 (m, 8H), 7.30-7.38 (m, 4H), 8.00-8.10 (b, 1H), 8.30 (t, 1H). M/z: 764.07 (M−1).

Example 89

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-O-benzyl-L-serine To a stirred solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine, (20.3 mg, 0.038 mmol) in DMF (2 ml) was added N-methylmorpholine (15 μl, 0.14 mmol). TBTU (14.8 mg, 0.046 mmol) was added the mixture was stirred at 30° C. for 1.5 hours. O-benzyl-L-serine (8.8 mg, 0.045 mmol) was added and the mixture was stirred overnight. The formation of the ketone of the title compound was confirmed. M/z: 718.04 (M+1) and 716.02 (M−1). Methanol (3 ml) and sodium borohydride (10.3 mg, 0.27 mmol) were added and the mixture was stirred for 1.5 hours. Ammonium acetate (20 mg) was added and the methanol was removed under reduced pressure. The remaining DMF-solution was purified by preparative HPLC on a C8 column, UV 240/260 nm. A gradient from 20 to 45% MeCN in 0.1M NH$_4$OAc buffer was used as eluent. The pure fractions were collected and the MeCN was removed under reduced pressure. The remaining water solution was acidified to pH 1 with HCl (1M) and extracted with DCM. The combined organic phases were concentrated and the residue was dissolved in MeCN and water. After lyophilisation, the title compound was obtained as a white solid (2.3 mg, 8.5%).

H-NMR (400 MHz, DMSO-d$_6$): 2.85-2.94 (m, 2H), 3.58-3.63 (m, 1H), 3.69-3.75 (m, 1H), 3.83 (d, 2H), 4.25 (d, 0.5H), 4.27 (d, 0.5H), 4.39-4.44 (m, 1H), 4.46 (d, 2H), 4.51 (s, 2H), 4.68-4.75 (m, 1H), 5.03 (d, 0.5H), 5.06 (d, 0.5), 6.98 (d, 2H), 7.05-7.17 (m, 4H), 7.20-7.26 (m, 3H), 7.28-7.39 (m, 8H), 8.20 (d, 1H), 8.25 (t, 1H). M/z: 718.10 (M−1).

Example 90

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(4-methylbenzyl)-D-cysteine To a stirred solution of N-{[4-((2R,3R)-1-(4-fluorophenyl)-3-{[2-(4-fluorophenyl)-2-oxoethyl]thio}-4-oxoazetidin-2-yl)phenoxy]acetyl}glycine, (19.9 mg, 0.037 mmol) in DMF (2.0 ml) was added N-methylmorpholine (15 μl, 0.14 mmol). TBTU (14.4 mg, 0.045 mmol) was added and the mixture was stirred at 30° C. for 45 minutes. S-(4-methylbenzyl)-D-cysteine (10.5 mg, 0.047 mmol) was added and the mixture was stirred at 30° C. for 1 hour. The formation of the ketone of the title compound was confirmed. M/z: 748.02 (M+1). Methanol (2 ml) and sodium borohydride (14.7 mg, 0.39 mmol) were added the mixture was stirred for 30 minutes. Ammonium acetate (20 mg) was added and the methanol was removed under reduced pressure. The remaining DMF-solution was purified with preparative HPLC on a C8 column, UV-detection 240/260 nm. A gradient from 20 to 50% MeCN in 0.1M NH$_4$OAc buffer was used as eluent. The pure fractions were collected and the MeCN was removed under reduced pressure. The remaining water solution was acidified to pH 1 with HCl (1M) and extracted with DCM. The combined organic phases were concentrated and the residue was dissolved in MeCN and water. After lyophilisation, the title compound was obtained as a white solid (8.7 mg, 31.5%). H-NMR (400 MHz, DMSO-d$_6$): 2.24 (s, 3H), 2.60-2.68 (m, 1H), 2.72-2.79 (m, 1H), 2.86-2.94 (m, 2H), 3.68 (s, 2H), 3.82 (d, 2H), 4.25 (d, 0.5H), 4.27 (d, 0.5H), 4.39-4.46 (m, 1H), 4.52 (s, 2H), 4.67-4.77 (m, 1H), 5.03 (d, 0.5H), 5.06 (d, 0.5H), 5.60-5.67 (bs, 1H), 6.98 (d, 2H), 7.05-7.18 (m, 8H), 7.20-7.25 (m, 2H), 4.30-4.39 (m, 4H), 8.23-8.32 (m, 2H), 12.80-12.95 (bs, 1H). M/z: 748.04 (M−1).

Example 91

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-ornithine N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-D-ornithine (0.021 g, 0.032 mmole) was dissolved in methanol (1.5 mL). NaBH$_4$ (0.0032 g, 0.085 mmole) was added and after about 15 min the reaction was complete according to LC-MS. A few drops of acetic acid was added. The solvent was removed under reduced pressure and the residue was purified by preparative HPLC on a Kromasil C8-column using 37% MeCN in 0.1M ammonium acetate buffer as eluent. After freeze-drying, 0.018 g (85%) of the desired product was obtained.

NMR (500 MHz, CD$_3$COOD) 1.62-1.80 (m, 3H), 1.91-2.00 (m, 1H), 2.92-3.10 (m, 4H), 3.98 (ABq, 2H), 4.05 (d, 0.5H), 4.08 (d, 0.5H), 4.27-4.32 (m, 1H), 4.64 (s, 2H), 4.82-4.87 (m, 1H), 4.93 (d, 0.5H), 4.94 (d, 0.5H), 6.99-7.06 (m, 4H), 7.09 (d, 2H), 7.28-7.33 (m, 2H), 7.33-7.41 (m, 4H)

Example 92

N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-N$^6$,N$^6$-dimethyl-L-lysine acetate N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-N$^6$,N$^6$-dimethyl-L-lysine (0.05 g, 0.007 mmole) was dissolved in methanol (1.5 mL). NaBH$_4$ (0.0065 g, 0.0172 mmole) was added and after about 15 min the reaction was complete according to LC-MS. A few drops of acetic acid were added. The solvent was removed under reduced pressure and the residue was purified by preparative HPLC on a Kromasil C8-column using 33.5% MeCN in 0.1M ammonium acetate buffer as eluent. After freeze-drying, 0.004 g (73%) of the desired product as the acetate-salt was obtained.

NMR (500 MHz, CD$_3$COOD) 1.33-1.43 (m, 2H), 1.62-1.78 (m, 3H), 1.85-1.98 (m, 4H), 2.83 (s, 6H), 2.91-3.08 (m, 4H), 3.94 (s, 2H), 4.02 (d, 0.5H), 4.05 (d, 0.5H), 4.25-4.30 (m, 1H), 4.61 (s, 2H), 4.79-4.85 (m, 1H), 4.90 (d, 0.5H), 4.92 (d, 0.5H), 6.96-7.08 (m, 6H), 7.25-7.30 (m, 2H), 7.30-7.38 (m, 4H)

Example 93

N-{[4-((2R,3R)-1-(4-fluorophenyl)-3-{[2-(4-fluorophenyl)-2 hydroxyethyl]thio}-4-oxoazetidin-2-yl)phenoxy]acetyl}glycyl-b,b-dimethyl-D-phenylalanine To a stirred solution of N-{[4-((2R,3R)-1-(4-fluorophenyl)-3-{[2-(4-fluorophenyl)-2-oxoethyl]thio}4-oxoazetidin-2-yl)phenoxy]acetyl}glycine (25.2 mg, 0.047 mmol) in DMF (2 ml) was added N-methylmorpholine (30 µl, 0.027 mmol). TBTU (18.0 mg, 0.056 mmol) was added and the mixture was stirred at 30° C. for 1 hour. β, β-dimethyl-D-phenylalanine trifluoroacetate was added and the mixture was stirred at 30° C. for 1.25 hours. The formation of the ketone of the title compound was confirmed. M/z: 716.07 (M+1) and 714.05 (M−1). Water (0.5 ml) was added. Methanol (2 ml) and sodium borohydride (18.2 mg, 0.48 mmol) were added the mixture was stirred for 25 minutes. Ammonium acetate (30 mg) was added and the methanol was removed under reduced pressure. The remaining DMF-solution was purified with preparative HPLC. A gradient from 20 to 48% MeCN in 0.1M NH$_4$OAc buffer was used as eluent. The MeCN was removed under reduced pressure and the remaining water solution was acidified to pH 1 with HCl (1M) and extracted with DCM. The organic phase was concentrated under reduced pressure and the residue was dissolved in MeCN and water. After lyophilisation, the title compound was obtained as a white solid (20.5 mg, 62%). H-NMR (400 MHz, DMSO-d$_6$): 1.27-1.32 (m, 6H), 2.75-3.05 (m, 2H), 3.55-3.67 (m, 1H), 3.79 (dd, 1H), 4.25-4.30 (m, 0.5H), 4.40 (s, 0.5H), 4.45-4.53 (m, 3H), 4.68-4.78 (m, 1H), 4.99 (d, 0.5H), 4.05 (d, 0.5H), 6.88-6.98 (m, 2H), 7.05-7.17 (m, 5H), 7.20-7.40 (m, 10H) 7.45-7.75 (m, 1H) 8.22 (t, 1H). M/z: 718.09 (M+1) and 716.07 (M−1).

Example 94

1-(4-Fluorophenyl)-3-(R)-[2-(4-fluorophenyl)-2-hydroxyethylthio]-4-(R)-{4-[N-(α-(R)-{N-[2-(hydroxy)-1-(S)-(carboxy)ethyl]carbamoyl}benzyl)carbamoylmethoxy]phenyl}azetidin-2-one To a solution of 1-(4-fluorophenyl)-3-(R)-[(4-fluorobenzoyl)methylthio]-4-(R)-{4-[N-(α-(R)-{N-[2-(hydroxy)-1-(S)-(carboxy)ethyl]carbamoyl}benzyl)carbamoylmethoxy]phenyl}azetidin-2-one (0.039 g, 0.055 mmol) in MeOH (3 ml) was added NaBH$_4$ (0.005 g, 0.135 mmol). After 10 min, water (2 ml) and acetic acid (2 drops) were added before most of the solvent was removed under reduced pressure. The residue was purified by preparative HPLC using a gradient of 20-60% MeCN in 0.1M ammonium acetate buffer as eluent. After freeze-drying the desired product was obtained in 0.038 g (96%) as a white solid. NMR (DMSO, 500 MHz): 2.90-3.00 (m, 2H), 3.50 (dd, 1H), 3.60 (dd, 1H), 4.15-4.30 (m, 2H), 4.60 (ABq, 2H), 4.70-4.80 (m, 1H), 5.00-5.05 (m, 1H), 5.65 (d, 1H), 6.95-7.45 (m, 17H), 8.30-8.45 (m, 2H); m/z: 706.4.

Example 95

1-(4-Fluorophenyl)-3-(R)-[2-(4-fluorophenyl)-2-hydroxyethylthio]-4-(R)-{4-[N(α-(R)-{N-[2-(t-butoxy)-1-(S)-(carboxy)ethyl]carbamoyl}benzyl)carbamoylmethoxy]phenyl}azetidin-2-one To a solution of 1-(4-fluorophenyl)-3-(R)-[(4-fluorobenzoyl)methylthio]-4-(R)-{4-[N-(α-(R)-{N-[2-(t-butoxy)-1-(S)-(carboxy)ethyl]carbamoyl}benzyl)carbamoylmethoxy]phenyl}azetidin-2-one (0.002 g, 0.003 mmol) in MeOH (3 ml) was added NaBH$_4$ (0.004 g, 0.108 mmol). After 10 min, the solution was added water (1 ml) and acetic acid (2 drops) before most of the solvent was removed under reduced pressure. The residue was purified by preparative HPLC using a gradient of 20-60% MeCN in 0.1M ammonium acetate buffer as eluent. After freeze-drying the desired product was obtained in 0.002 g (~quantitative yield) as a white solid. NMR (DMSO, 500 MHz): 1.00 (s, 9H), 2.90-3.00 (m, 2H), 3.40-3.55 (m, 2H), 4.20-4.30 (m, 2H), 4.60 (ABq, 2H), 4.70-4.80 (m, 1H), 5.00-5.05 (m, 1H), 5.70 (d, 1H), 6.95-7.45 (m, 17H), 8.20 (bs, 1H), 8.35 (d, 1H); m/z: 762.5.

Example 96

1-(4-Fluorophenyl)-3-(R)-[2-(4-fluorophenyl)-2-hydroxyethylthio]-4-(R)-{4-[N-{N-[2-(hydroxy)-1-(R)-(carboxy)ethyl]carbamoylmethyl}carbamoylmethoxy]phenyl}azetidin-2-one To a solution of 1-(4-fluorophenyl)-3-(R)-[(4-fluorobenzoyl)methylthio]-4-(R)-{4-[N-{N-[2-(hydroxy)-1-(R)-(carboxy)ethyl]carbamoylmethyl}carbamoylmethoxy]phenyl}azetidin-2-one (0.028 g, 0.045 mmol) in MeOH (3 ml) was added NaBH$_4$ (0.010 g, 0.264 mmol). After 10 minutes the solvent was removed under reduced pressure and the residue was purified by preparative HPLC using a gradient of 20-50% MeCN in 0.1M ammonium acetate buffer as eluent. After freeze-drying the desired product was obtained in 0.014 g (50%) as a white solid. NMR (CD$_3$COOD, 400 MHz): 3.00-3.20 (m, 2H), 3.95 (dd, 1H), 4.00-4.15 (m, 2H), 4.25 (ABq, 2H), 4.70 (s, 2H), 4.70-4.80 (m, 1H), 4.85-5.00 (m, 2H), 6.95-7.10 (m, 6H), 7.25-7.45 (m, 6H); m/z: 630.1.

Example 97

1-(4-Fluorophenyl)-3-(R)-[2-(4-fluorophenyl)-2-hydroxyethylthio]-4-(R)-{4-[N-{N-[2-(phenyl)-1-(R)-(carboxy)ethyl]carbamoylmethyl}carbamoylmethoxy]phenyl}azetidin-2-one 1-(4-Fluorophenyl)-3-(R)-[(4-fluorobenzoyl)methylthio]-4-(R)-{4-[N-{N-[2-(phenyl)-1-(R)-(carboxy)ethyl]carbamoylmethyl}carbamoylmethoxy]phenyl}azetidin-2-one (15 mg, 0.022 mmol) was dissolved in methanol (1 ml) and sodium borohydride (4 mg) was added. The solvent was evaporated and the residue was purified by preparative HPLC using a gradient from 10% to 100% MeCN in 0.1 M ammonium acetate buffer as mobile phase. Lyophilisation of the product fraction gave 8 mg (53%) of the desired product. NMR (400 MHz, CD$_3$COOD): 3.02-3.17 (m, 3H), 3.19-3.25 (m, 1H), 4.06-4.17 (m, 3H), 4.66 (s, 2H), 4.87-4.96 (m, 3H), 6.97-7.05 (m, 6H), 7.10-7.40 (m, 12H); m/z 688.3 (m-H).

Examples 98-136

The following compounds could be prepared by the procedure of Example 97, but wherein different protecting groups may be used.

| Ex | R$^1$ | R$^2$ | R$^3$ | R$^4$ |
|---|---|---|---|---|
| 98 | H | Me | F | H |
| 99 | Ph | Me | F | H |
| 100 | H | Me | F | F |
| 101 | H | Me | H | H |
| 102 | Ph | Me | H | H |
| 103 | H | —CH(Me)$_2$ | F | H |
| 104 | Ph | —CH(Me)$_2$ | F | H |
| 105 | Ph | —CH(Me)$_2$ | H | H |
| 106 | H | —CH$_2$CH(Me)$_2$ | F | H |
| 107 | Ph | —CH$_2$CH(Me)$_2$ | F | H |
| 108 | Ph | —CH$_2$CH(Me)$_2$ | F | F |
| 109 | H | —CH$_2$CH(Me)$_2$ | H | H |
| 110 | Ph | —CH$_2$CH(Me)$_2$ | H | H |
| 111 | H | Ph | F | H |
| 112 | Ph | Ph | F | H |
| 113 | H | Ph | H | H |
| 114 | Ph | Ph | H | H |
| 115 | H | —CH$_2$Ph | F | H |
| 116 | Ph | —CH$_2$Ph | F | H |
| 117 | Ph | —CH$_2$Ph | F | F |
| 118 | Ph | —CH$_2$Ph | H | H |
| 119 | H | —CH$_2$(4-HOPh) | F | H |
| 120 | Ph | —CH$_2$(4-HOPh) | F | H |
| 121 | Ph | —CH$_2$(4-HOPh) | F | F |
| 122 | H | —CH$_2$(4-HOPh) | H | H |
| 123 | Ph | —CH$_2$(4-HOPh) | H | H |
| 124 | H | —CH$_2$OH | H | H |
| 125 | H | —CH$_2$COOH | F | F |
| 126 | H | —CH$_2$CH$_2$COOH | F | F |
| 127 | H | —CH$_2$CH$_2$CH$_2$CH$_2$NHC(=NH)NH$_2$ | F | F |
| 128 | H | 4-HOPh | F | F |
| 129 | Ph | —CH$_2$CH$_2$COOH | F | F |
| 130 | Ph | —CH$_2$CH$_2$CH$_2$CH$_2$NHC(=NH)NH$_2$ | F | F |
| 131 | Ph | 4-HOPh | F | F |
| 132 | Ph | —CH$_2$indol-3-yl | F | F |
| 133 | Ph | —CH$_2$imidazol-4-yl | F | F |
| 134 | Ph | —CH$_2$CH$_2$SMe | F | F |
| 135 | Ph | cyclohexyl | F | F |
| 136 | Ph | —CH$_2$cyclohexyl | F | F |

Preparation of Starting Materials for the Above Examples

Methods

Method 1

N-{[4-((2R,3R)-1-(4-fluorophenyl)-3-{[2-(4-fluorophenyl)-2-oxoethyl]thio}-4-oxoazetidin-2-yl)phenoxy]acetyl}-D-alanine

[4-((2R,3R)-1-(4-fluorophenyl)-3-{[2-(4-fluorophenyl)-2-oxoethyl]thio}-4-oxoazetidin-2-yl)phenoxy]acetic acid (50 mg, 0.1 mmol), tert-butyl D-alaninate (23 mg, 0.12 mmol) and 4-methylmorpholine (31 mg, 0.31 mmol) were dissolved in DCM (1.5 ml) and stirred at room temperature for 5 minutes. TBTU (40 mg, 0.12 mmol) was added and the reaction mixture was stirred for 2 h. TFA (0.7 ml) was added and the solution was stirred for 90 minutes. TFA and DCM were removed under reduced pressure and the residue was dissolved in DCM and washed with water. The organic layer was dried over sodium sulphate and the solvent was removed under reduced pressure giving 55 mg (95%) of the title product. M/z: 553.0 (M−1).

Method 2

[4-((2R,3R)-3-{[(5,5-dimethyl-2-phenyl-1,3-dioxan-2-yl)methyl]thio}-4-oxo-1-phenylazetidin-2-yl)phenoxy]acetic acid To a solution of ethyl [4-((2R,3R)-3-{[(5,5-dimethyl-2-phenyl-1,3-dioxan-2-yl)methyl]thio}-4-oxo-1-phenylazetidin-2-yl)phenoxy]acetate (0.86 g, 1.53 mmol) in MeOH (25 ml) was added water (2.5 ml) and triethylamine (1.55 g). The reaction was stirred for 48 h at 50° C. The solvent was evaporated and the residue was purified by preparative HPLC using a gradient of 20-70% CH$_3$CN in 0.1M NH$_4$OAc buffer. Freeze-drying of the pure fractions gave the title compound as a colourless solid. $^1$H NMR [(CD$_3$)$_2$SO), 400 MHz] 0.50 (s, 3H), 1.15 (s, 3H), 2.93 (d, 1H), 2.96 (d, 1H), 3.21-3.37 (m, 4H), 4.13 (d, 1H), 4.28 (s, 2H), 4.97 (d, 1H), 6.83-7.41 (m, 14H).

Method 3

N-[(4-{(2R,3R)-4-oxo-3-[(2-oxo-2-phenylethyl)thio]-1-phenylazetidin-2-yl}phenoxy)acetyl]glycine Glycine tert-butyl ester (0.015 g, 0.112 mmol) and N-Methylmorpholine (0.028 g, 0.281 mmol) were added to a solution of [4-((2R,3R)-3-{[(5,5-dimethyl-2-phenyl-1,3-dioxan-2-yl)methyl]thio}-4-oxo-1-phenylazetidin-2-yl)phenoxy]acetic acid (0.050 g, 0.094 mmol) in CH$_2$Cl$_2$ (5 ml). After 10 minutes, TBTU (0.039 g, 0.122 mmol) was added. The reaction was stirred overnight. The resulting tert-butyl ester was purified on silica gel and eluted with EtOAc/CH$_2$Cl$_2$ (25/75). The pure fractions were collected and concentrated. CH$_2$Cl$_2$ (4 ml) and TFA (1 ml) were added. The solvent was evaporated after 2 h and the residue was purified by preparative HPLC using an eluent of 20-70% CH$_3$CN in 0.1M NH$_4$OAc buffer. Freeze-drying of the pure fractions gave the title product as a colourless solid. M/z: 503.5 (M−1). $^1$H NMR (CD$_3$CN), 400 MHz) δ 3.84 (d, 2H), 4.18 (d, 1H), 4.24 (s, 2H), 4.50 (s, 2H), 5.04 (d, 1H), 6.99-7.12 (m, 3H), 7.25-7.66 (m, 9H), 7.94-7.96 (m, 2H).

Method 4

(2R)-({[4-((2R,3R)-1-(4-fluorophenyl)-3-{[2-(4-fluorophenyl)-2-oxoethyl]thio}-4-oxoazetidin-2-yl) phenoxy]acetyl}amino)(phenyl)acetic acid

[4-((2R,3R)-1-(4-Fluorophenyl)-3-{[2-(4-fluorophenyl)-2-oxoethyl]thio}-4-oxoazetidin-2-yl)phenoxy]acetic acid (0.40 g, 0.827 mmol) was dissolved in CH$_2$Cl$_2$ (40 ml) and tert-butyl (2R)-amino(phenyl)acetate (0.206 g, 0.993 mmol) and N-methylmorpholine (0.251 g, 2.48 mmol) were added. After 10 minutes, TBTU (0.345 g, 1.076 mmol) was added. The reaction was stirred overnight. The resulting tert-butyl ester was concentrated and purified on silica gel (eluted with EtOAc/CH$_2$Cl$_2$ 25/75). The pure fractions were collected and concentrated. CH$_2$Cl$_2$ (25 ml) and TFA (3 ml) were added. The mixture was stirred for 5 days and the solvent was removed under reduced pressure. The residue was purified by preparative HPLC using a gradient of 20-70% CH$_3$CN in 0.1M NH$_4$OAc buffer. Freeze-drying of the pure fractions gave the title compound as a colourless solid. M/z: 615.50 (M−1). $^1$H NMR [(CD$_3$)$_2$SO], 400 MHz] δ 4.35 (d, 1H), 4.36 (d, 1H), 4.40 (d, 1H), 4.53 (d, 1H), 4.58 (d, 1H), 4.94 (d, 1H), 5.19 (d, 1H), 6.97-7.40 (m, 15H), 8.02-8.06 (m, 2H), 8.26-8.32 (m, 1H).

Method 5

N-{[4-((2R,3R)-1-(4-fluorophenyl)-3-{[2-(4-fluorophenyl)-2-oxoethyl]thio}-4-oxoazetidin-2-yl)phenoxy]acetyl}-D-valine

[4-((2R,3R)-1-(4-Fluorophenyl)-3-{[2-(4-fluorophenyl)-2-oxoethyl]thio}-4-oxoazetidin-2-yl)phenoxy]acetic acid, (50.0 mg, 0.10 mmol) was dissolved in DCM (2 ml). tert-Butyl D-valinate hydrochloride (28.4 mg, 0.14 mmol) and N-methylmorpholine (3.0 µl, 0.31 mmol) were added. After 5 minutes, TBTU (43.7 mg, 0.14 mmol) was added and the mixture was stirred overnight. The intermediate tert-butyl-ester of the title compound was confirmed. M/z: 637.1 (M−H). The solvent was removed under reduced pressure. The yellow residue was dissolved in formic acid (1.5 ml) and heated at 50° C. for 5 h. The solvent was evaporated and the residue was purified by preparative HPLC on a C8 column. A gradient from 20 to 50% MeCN in 0.1 M ammonium acetate buffer was used as eluent. After lyophilisation, the title compound was obtained as a white solid (30.5 mg, 51%). 1H-NMR (400 MHz, DMS-d$_6$): 0.74 (t, 6H), 1.98-2.07 (m, 1H), 3.84 (brs, 1H), 4.32 (d, 1H), 4.35 (s, 1H), 4.36 (s, 1H), 4.50 (brs, 2H), 5.16 (d, 1H), 6.96 (d, 2H), 7.10-7.17 (m, 2H), 7.19-7.24 (m, 2H), 7.31-7.38 (m, 4H), 7.66 (brs, 1H), 7.99-8.04 (m, 2H). M/z: 583.0 (M+H) and 581.0 (M−H).

Method 6

(N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-D-valine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0229 g, 0.042 mmol), (R)-valin tert-butylester hydrochloride (0.0121 g, 0.058 mmol) and N-methylmorpholine (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete according to LC-MS. The solvent was removed under reduced pressure and the residue was purified by preparative HPLC on a Kromasil C8-column using a gradient of 5-100% MeCN in 0.15% trifluoroacetic acid buffer as eluent. The solvent was removed under reduced pressure and 0.022 g (81%) of the title product was obtained. M/z 640.06.

Method 7

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-threonine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0188 g, 0.035 mmol), tert-butyl O-(tert-butyl)-L-threoninate (0.0151 g, 0.065 mmol) and N-methylmorpholine (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete according to LC-MS. The solvent was removed under reduced pressure and the residue was purified by preparative HPLC on a Kromasil C8-column using a gradient of 5-100% MeCN in 0.15% trifluoroacetic acid buffer as eluent. The solvent was removed under reduced pressure and 0.014 g (63%) of the title product was obtained. M/z 641.92.

Method 8

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-asparagine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0213 g, 0.039 mmol), tert-butyl L-asparaginate hydrochloride (0.0141 g, 0.063 mmol) and N-methylmorpholine (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete according to LC-MS. The solvent was removed under reduced pressure and the residue was purified by preparative HPLC on a Kromasil C8-column using a gradient of 5-100% MeCN in 0.15% trifluoroacetic acid buffer as eluent. The solvent was removed under reduced pressure and 0.020 g (77%) of the title product was obtained. M/z 655.11.

Method 9

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-methionine A mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.0197 g, 0.036 mmol), tert-butyl L-methioninate hydrochloride (0.0144 g, 0.060 mmol) and N-methylmorpholine (0.012 ml, 0.111 mmol) in DCM (2 ml) was stirred at room temperature. TBTU (0.018 g, 0.056 mmol) was added and the mixture was stirred overnight. Trifluoroacetic acid (0.65 ml) was added and after a couple of hours the hydrolysis was complete according to LC-MS. The solvent was removed under reduced pressure and the residue was purified by preparative HPLC on a Kromasil C8-column using a gradient of 5-100% MeCN in 0.15% trifluoroacetic acid buffer as eluent. The solvent was removed under reduced pressure and 0.015 g (61%) of the title product was obtained. M/z 672.10.

Method 10 tert-butyl N-[(benzyloxy)carbonyl]glycyl-D-valinate

A mixture of N-[(benzyloxy)carbonyl]glycine (, 2.4 g, 11.5 mmol), tert-butyl D-valinate hydrochloride (2.4 g, 11.4 mmol) and N-methylmorpholine (2.53 ml, 22.9 mmol) in DCM (20 ml) was stirred at room temperature. TBTU (4.79 g, 14.9 mmol) was added and the mixture was stirred for three days. The solvent was removed under reduced pressure. Water was added and the mixture was extracted two times with toluen. The organic layer was washed with brine, dried ($Na_2SO_4$), filtered and concentrated. The crude product was purified by flash chromatography using DCM:EtOAc:aceton 4:1:1 as eluent to give 3.92 g (94%) of the title compound. NMR (500 MHz, $CD_3COOD$) 0.88-0.99 (m, 6H), 1.48 (s, 9H), 2.08-2.19 (m 1H), 3.85 (ABq, 2H), 4.24 (d, 1H), 5.12 (ABq, 2H), 7.28-7.41 (m, 5H).

Method 11 tert-butyl glycyl-D-valinate hydrochloride tert-Butyl N-[(benzyloxy)carbonyl]glycyl-D-valinate (3.89 g, 10.7 mmol) and Pd on charcoal (95%, 0.3 g) were mixed in EtOH (95%, 80 ml) and stirred under $H_2$-atmosphere for 2 h. The mixture was filtered through Celite 521 and the solvent was evaporated under reduced pressure. MeCN (25 ml) and pyridine hydrochloride (1.25 g, 10.8 mmol) were added. The solvent was evaporated under reduced pressure to give 2.3 g (81%) of the title product. NMR (500 MHz, $CD_3COOD$) 0.96-1.01 (m, 6H), 1.49 (s, 9H), 2.13-2.23 (m 1H), 3.76 (AB, 2H), 4.28-4.33 (m, 1H).

Method 12

N-{[4-((2R,3R)-1-(4-fluorophenyl)-3-{[2-(4-methoxyphenyl)-2-oxoethyl]thio}-4-oxoazetidin-2-yl) phenoxy]acetyl}glycyl-D-valine A mixture of [4-((2R,3R)-1-(4-fluorophenyl)-3-{[2-(4-methoxyphenyl)-2-oxoethyl]thio}-4-oxoazetidin-2-yl)phenoxy]acetic acid (0.0153 g, 0.031 mmol), tert-butyl glycyl-D-valinate hydrochloride (0.0099 g, 0.037 mmol) and N-methylmorpholine (0.010 ml, 0.091 mmol) in DCM (2 ml) was stirred at room temperature. TBTU (0.016 g, 0.050 mmol) was added and the mixture was stirred for 3.5 h. Trifluoroacetic acid (0.5 ml) was added and after 3.5 h the solvent was removed under reduced pressure. The residue was purified by preparative HPLC on a Kromasil C8-column using a gradient of 5-100% MeCN in 0.15% trifluoroacetic acid buffer as eluent. The solvent was removed under reduced pressure and 0.015 g (74%) of the title product was obtained. M/z 652.20.

Method 13

N-{[4-((2R,3R)-1-(4-fluorophenyl)-3-{[2-(4-methoxyphenyl)-2-oxoethyl]thio}-4-oxoazetidin-2-yl) phenoxy]acetyl}glycine A mixture of [4-((2R,3R)-1-(4-fluorophenyl)-3-{[2-(4-methoxyphenyl)-2-oxoethyl]thio}-4-oxoazetidin-2-yl)phenoxy]acetic acid (0.150 g, 0.30 mmol), tert-butyl glycinate hydrochloride (0.0635 g, 0.38 mmol) and N-methylmorpholine (0.10 ml, 0.91 mmol) in DCM (2 ml) was stirred at room temperature. TBTU (0.128 g, 0.40 mmol) was added and the mixture was stirred overnight. Trifluoroacetic acid (4.0 ml) was added and after 2 h the solvent was removed under reduced pressure. The residue was purified by preparative HPLC on a Kromasil C8-column using 35% MeCN in 0.1M ammonium acetate buffer as eluent. The solvent was removed under reduced pressure and 0.159 g (95%) of the title product was obtained. M/z 553.02.

Method 14

N-{[4-((2R,3R)-1-(4-Fluorophenyl)-3-{[2-(4-fluorophenyl)-2-oxoethyl]thio}-4-oxoazetidin-2-yl)phenoxy]acetyl}glycyl-2-butylnorleucine N-{[4-((2R,3R)-1-(4-fluorophenyl)-3-{[2-(4-fluorophenyl)-2-oxoethyl]thio}-4-oxoazetidin-2-yl)phenoxy] acetyl}glycine (0.020 g, 0.037 mmol) and NMM (0.040 ml, 0.363 mmol) were dissolved in DCM (5 ml) at 30° C. TBTU (a total of 0.016 g, 0.050 mmol) were added in portions and the mixture was stirred for 1 h. 2-Butylnorleucine (0.007 g, 0.037 mmol) was added and the mixture was stirred at 30° C. for 18 h. The reaction mixture was concentrated under reduced pressure and the residue was purified by preparative HPLC, using a gradient of 20-50% MeCN in 0.1M ammonium acetate buffer as eluent. After freeze-drying, 0.009 g (34% yield) of the title product was obtained as a white solid. M/z: 710.1. 1H NMR (DMSO, 400 MHz): δ 0.73-0.82 (m, 6H), 0.88-1.22 (m, 8H), 1.56-1.69 (m, 2H), 1.96-2.07 (m, 2H), 3.71 (d, 2H), 4.32 (d, 1H), 4.36 (ABq, 2H), 4.52 (s, 2H), 5.16 (d, 1H), 6.95-7.01 (m, 2H), 7.11-7.26 (m, 4H), 7.30-7.40 (m, 4H), 7.61 (s, 1H), 7.98-8.06 (m, 2H), 8.25-8.42 (m, 1H).

Method 15

N-{[4-((2R,3R)-1-(4-Fluorophenyl)-3-{[2-(4-fluorophenyl)-2-oxoethyl]thio}-4-oxoazetidin-2-yl)phenoxy]acetyl}-L-alanine A solution of [4-((2R,3R)-1-(4-fluorophenyl)-3-{[2-(4-fluorophenyl)-2-oxoethyl]thio}-4-oxoazetidin-2-yl)phenoxy]acetic acid (0.020 g, 0.041 mmol), L-Alanine tert-butyl ester hydrochloride (0.009 g, 0.050 mmol) and N-Methylmorpholine (0.018 ml, 0.163 mmol) in DCM (4 ml) was stirred for 5 min. TBTU (0.017 g, 0.053 mmol) was added. The formation of the ester was confirmed after 3 h. M/z: 611.1. TFA (3 ml) was added. After 2 h, the mixture was diluted with toluene (2 ml) and the solvent was removed under reduced pressure. The residue was purified by preparative HPLC, using a gradient of 20-50% MeCN in 0.1M ammonium acetate buffer as eluent. After freeze-drying, 0.023 g (>98%) of the title product was obtained as a white solid. M/z: 555.1. 1H NMR (DMSO, 400 MHz): δ 1.17 (d, 3H), 3.73-3.82 (m, 1H), 4.33 (d, 1H), 4.35 (ABq, 2H), 4.43 (s, 2H), 5.15 (d, 1H), 6.92-7.98 (m, 2H), 7.10-7.24 (m, 4H), 7.29-7.39 (m, 4H), 7.84 (d, 1H), 7.97-8.04 (m, 2H).

Method 16

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-phenylalanine Methyl N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-phenylalaninate (20 mg, 0.029 mmol) was dissolved in 1.6 ml MeOH and 0.2 ml $H_2O$. $Et_3N$ (0.2 ml, 1.44 mmol) was added and the mixture was stirred overnight. The mixture was heated to 80° C. for 7 h. The mixture was purified by preparative HPLC using a C8 column (25×300 mm). A gradient from 20% to 40% MeCN in 0.1 M ammonium acetate was used as mobile phase. The product fraction was concentrated and lyophilized to yield 7 mg (36%). M/z: 688.

Method 17 methyl N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-L-phenylalaninate N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (66 mg, 0.12 mmol) was dissolved in 2 ml DCM. N-methylmorpholine (40 ul, 0.36 mmol), L-(S)-phenylalanine methyl ester hydrochloride (33 mg, 0.15 mmol) and finally TBTU (45 mg, 0.14 mmol) were added. The mixture was stirred overnight. The crude mixture was purified by flash chromatography on 5 g $SiO_2$. EtOAc:Hex (1:1), DCM and finally DCM:Acetone (4:1) were used as eluents. The collected fraction was concentrated to yield 67 mg (78%) of the title compound. M/z: 702 (M+1).

Method 18 tert-butyl N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-4-methylleucinate N-{[4-((2R,3R)-1-(4-Fluorophenyl)-3-{[2-(4-fluorophenyl)-2-oxoethyl]thio}-4-oxoazetidin-2-yl)phenoxy]acetyl}glycine (20 mg, 0.037 mmol) was dissolved in 3 ml DCM. N-Methylmorpholine (9 µl, 0.082 mmol) and TBTU (14 mg, 0.044 mmol) were added. After 5 minutes, tert-butyl 4-methylleucinate (9 mg, 0.045 mmol) was added and the mixture was stirred for 2 h. Additional tert-butyl 4-methylleucinate (ca 3 mg, 0.015 mmol) was added. After 15 min, water (2 ml) was added and the mixture was acidified to a pH of 2 using 2M $KHSO_4$. The aqueous phase was extracted with 2 ml DCM and the combined organic phases were washed with 3 ml water, dried over $Na_2SO_4$ and filtered. Removal of the solvent under reduced pressure gave the title compound. M/z: 724.

Method 19

N-{[4-((2R,3R)-1-(4-Fluorophenyl)-3-{[2-(4-fluorophenyl)-2-oxoethyl]thio}-4-oxoazetidin-2-yl)phenoxy]acetyl}glycylglycine A solution of [4-((2R,3R)-1-(4-fluorophenyl)-3-{[2-(4-fluorophenyl)-2-oxoethyl]thio}-4-oxoazetidin-2-yl)phenoxy]acetic acid (0.200 g, 0.414 mmol), glycylglycine methyl ester hydrochloride (0.090 g, 0.493 mmol) and N-methylmorpholine (0.150 ml) in DCM (5 ml) was stirred for 10 min. TBTU (0.170 g) was added and the mixture was stirred for 20 h. The formation of the ester was confirmed. M/z: 612.0. The solvent was removed under reduced pressure. The residue was dissolved in a mixture of MeOH (5 ml), water (1 ml) and $Et_3N$ (0.5 ml). The solution was stirred at 50° C. for 18 h. DBN (0.050 ml, 0.405 mmol) was added and the mixture was stirred for 2 h at 50° C. Ammonium acetate buffer (0.1 M, 3 ml) was added and the mixture was concentrated. The residue was purified by preparative HPLC, using a gradient of 20-50% MeCN in 0.1M ammonium acetate buffer as eluent. After freeze-drying, the title product (0.094 g, 38% yield) was obtained as a white solid. M/z: 598.2. 1H NMR (DMSO, 400 MHz): 3.50 (d, 2H), 3.75 (d, 2H), 4.32 (d, 1H), 4.35 (ABq, 2H), 4.46-4.53 (m, 2H), 5.15 (d, 1H), 6.94-7.00 (m, 2H), 7.10-7.25 (m, 4H), 7.29-7.39 (m, 4H), 7.68-7.81 (m, 1H), 7.98-8.04 (m, 2H), 8.30-8.36 (m, 1).

Method 20

Ethyl {[(5,5-dimethyl-2-phenyl-1,3-dioxan-2-yl)methyl]thio}acetate

Ethyl [(2-oxo-2-phenylethyl)thio]acetate (10.8 g, 45.3 mmol) was dissolved in toluene (250 ml). 2,2-Dimethyl-1,3-propanediol (37.6 g, 0.36 mol) and p-toluene sulfonic acid (cat., 500 mg) were added. The mixture was stirred at reflux in a Dean-Stark apparatus for two hours and at room temperature overnight. The mixture was concentrated under reduced pressure. The crude oil was purified by flash-chromatography (hexane:EtOAc-7:1) to give 11.2 g (70%) of the title compound as a colourless oil. $^1$H-NMR ($CDCl_3$, 200 MHz): δ 0.6 (s, 3H), 1.2-1.3 (t, 3H), 1.4 (s, 3H), 3.0 (s, 2H), 3.2 (s, 2H), 3.5 (s, 4H), 4.1-4.2 (q, 2H), 7.3-7.6 (m, 5H).

Method 21

{[(5,5-Dimethyl-2-phenyl-1,3-dioxan-2-yl)methyl]thio}acetic acid

Ethyl {[(5,5-dimethyl-2-phenyl-1,3-dioxan-2-yl)methyl]thio}acetate (11.2 g, 34.3 mmol) was dissolved in THF (150 ml) and cooled to 0° C. LiOH (2.88 g, 68.7 mmol) in water (40 ml) was added and the mixture was stirred for 19 h. The solvents were evaporated. The crude-product was extracted between water and diethyl ether. The aqueous layer was acidified to a pH of 6 using 2M HCl and extracted twice with $CH_2Cl_2$. The combined $CH_2Cl_2$ layers were dried ($Na_2SO_4$) and concentrated under reduced pressure to give 9.8 g (96%) of the title compound as a white solid. $^1$H-NMR ($CDCl_3$, 200 MHz): δ 0.6 (s, 3H), 1.4 (s, 3H), 3.0 (s, 2H), 3.3 (s, 2H), 3.5 (s, 4H), 7.3-7.6 (m, 5H).

Method 22

(4S)-3-({[(5,5-Dimethyl-2-phenyl-1,3-dioxan-2-yl)methyl]thio}acetyl)-4-phenyl-1,3-oxazolidin-2-one {[(5,5-Dimethyl-2-phenyl-1,3-dioxan-2-yl)methyl]thio}acetic acid (9.9 g, 33.0 mmol) was dissolved in dry $CH_2Cl_2$ (250 ml) and cooled to 0° C. N,N'-Dicyclohexylcarbodiimide (DCC, 7.63 g, 37.0 mmol) and 4-(dimethylamino)pyridine (DMAP, 8.57 g, 70.0 mmol) were added and the mixture was stirred at 0° C. for 20 minutes. (S)-(+)-4-Phenyl-2-oxazolidinone (5.38 g, 33.0 mmol) was added and the mixture was stirred at room temperature for 70 h. The mixture was filtered, concentrated under reduced pressure and purified by flash-chromatography (hexane:EtOAc-7:3). This afforded 10.2 g (70%) of the title compound as a white solid. $^1$H-NMR (CDCl$_3$, 200 MHz): 0.6 (s, 3H), 1.3 (s, 3H), 2.8 (s, 2H), 3.4 (s, 4H), 3.8 (s, 2H), 4.1-4.15 (dd, 1H), 4.6-4.8 (t, 1H), 5.35-5.45 (dd, 1H), 7.25-7.45 (m, 9H).

Method 23

Ethyl (4-{(1S,2R)-1-anilino-2-{[5,5-dimethyl-2-phenyl-1,3-dioxan-2-yl)methy]thio}-3-oxo-3-[(4S)-2-oxo-4-phenyl-1,3-oxazolidin-3-yl]propyl}phenoxy)acetate Tetraisopropyl orthotitanate (0.5 ml, 1.7 mmol) was added to a solution of TiCl$_4$ (1M in CH$_2$Cl$_2$, 5.1 ml, 5.1 mmol) in CH$_2$Cl$_2$ (50 ml) at 0° C. under inert atmosphere. The mixture was stirred for ten minutes. (4S)-3-({[(5,5-Dimethyl-2-phenyl-1,3-dioxan-2-yl)methyl]thio}acetyl)-4-phenyl-1,3-oxazolidin-2-one (3.0 g, 6.8 mmol) in dry CH$_2$Cl$_2$ (60 ml) was added dropwise over 20 minutes and the mixture was stirred for ten minutes. Ethyl {4-[(phenylimino)methyl]phenoxy}acetate (3.8 g, 13.6 mmol) in dry CH$_2$Cl$_2$ (60 ml) was added dropwise over 30 minutes and the mixture was cooled to –40° C. and stirred for 20 minutes. Ethyl diisopropyl amine (2.3 ml, 13.6 mmol) was added dropwise over ten minutes and the mixture was stirred at 40° C. for six hours. The mixture was cooled to –78° C. and isopropanol (90 ml) was added. The mixture was slowly warmed to room temperature overnight. H$_2$O (100 ml) was added and the mixture was stirred for 35 minutes at room temperature. NH$_4$Cl (10%) was added and the mixture was extracted twice with diethyl ether. The combined organic layers were washed with water, dried (MgSO$_4$) and concentrated under reduced pressure. Purification by flash-chromatography (hexane:EtOAc 5:1 then 7:3 then 6:4) gave 2.13 g (43%) of the title compound as a yellow solid. $^1$H-NMR (CDCl$_3$, 200 MHz): δ 0.6 (s, 3H), 1.2-1.4 (m, 6H), 2.8-3.0 (m, 2H), 3.3-3.5 (m, 4H), 4.5-4.7 (m, 3H), 5.3-5.5 (m, 1H), 5.7-5.8 (d, 1H), 6.4-6.5 (d, 2H), 6.6-6.9 (m, 4H), 6.9-7.0 (d, 2H), 7.0-7.5 (m, 7H). M/z: 747.3 (M++Na)

Method 24

Ethyl [4-((2R,3R)-3-{[(5,5-dimethyl-2-phenyl-1,3-dioxan-2-yl)methyl]thio}-4-oxo-1-phenylazetidin-2-yl)phenoxy]acetate Ethyl (4-{(1S,2R)-1-anilino-2-{[(5,5-dimethyl-2-phenyl-1,3-dioxan-2-yl)methyl]thio}-3-oxo-3-[(4S)-2-oxo-4-phenyl-1,3-oxazolidin-3-yl]propyl}phenoxy)acetate (2.1 g, 2.9 mmol) was dissolved in dry toluene (200 ml) and heated to 90° C. under inert atmosphere. N,O-Bis(trimethylsilyl)acetamide (BSA, 2.1 ml, 8.7 mmol) was added and the mixture was stirred at 90° C. for one hour. At 45° C. tetrabutylammonium fluoride (TBAF, cat., 0.1 g) was added and the mixture was stirred at 45° C. for 18 h. The mixture was concentrated under reduced pressure. The residue was purified by flash-chromatography (hexane:EtOAc 5:1). This afforded 0.98 g (60%) of the title compound as a yellow oil. $^1$H-NMR (CDCl$_3$, 200 MHz): 0.6 (s, 3H), 1.2-1.4 (m, 6H), 3.0-3.2 (t, broad, 2H), 3.3-3.5 (m, 4H), 3.95 (d, 1H), 4.2-4.4 (q, 2H), 4.6 (s, 2H), 4.8 (d, 1H), 6.9-7.1 (m, 3H), 7.2-7.6 (m, 1H). MS (CI) M/z: 584.2 (M++Na).

Method 25 tert-Butyl (4-{(1S,2R)-2-{[(5,5-dimethyl-2-phenyl-1,3-dioxan-2-yl)methyl]thio}-1-[(4-fluorophenyl)amino]-3-oxo-3-[(4S)-2-oxo-4-phenyl-1,3-oxazolidin-3-yl]propyl}phenoxy)acetate Tetraisopropyl orthotitanate (0.51 ml, 1.8 mmol) was added to a solution of TiCl$_4$ (1M in CH$_2$Cl$_2$, 5.1 ml, 5.1 mmol) in CH$_2$Cl$_2$ (50 ml) at 0° C. under inert atmosphere. The mixture was stirred for ten minutes. (4S)-3-({[(5,5-Dimethyl-2-phenyl-1,3-dioxan-2-yl)methyl]thio}acetyl)-4-phenyl-1,3-oxazolidin-2-one (3.0 g, 6.8 mmol) in dry CH$_2$Cl$_2$ (50 ml) was added dropwise over 20 minutes. After ten minutes, tert-butyl (4-{[(4-fluorophenyl)imino]methyl}phenoxy)acetate (4.5 g, 13.6 mmol) in dry CH$_2$Cl$_2$ (50 ml) was added dropwise over 30 minutes. The mixture cooled to –30° C. and stirred for 20 minutes. Ethyl diisopropyl amine (2.3 ml, 13.4 mmol) in 20 ml dry CH$_2$Cl$_2$ was added dropwise over ten minutes and the mixture was stirred at –30° C. for six hours. The mixture was cooled to –78° C. Isopropanol (60 ml) was added and the temperature was risen overnight. H$_2$O (100 ml) was added and the mixture was stirred for 35 minutes at room temperature. The mixture was extracted twice with diethyl ether. The combined organic layers were washed with water, dried (MgSO$_4$) and concentrated under reduced pressure. Purification by flash-chromatography (hexane:EtOAc 5:1) afforded 2.95 g (56%) of the title compound as a yellow solid. M/z: 793.3 (M++Na).

Method 26 tert-Butyl {4-[(2R,3R)-3-{[(5,5-dimethyl-2-phenyl-1,3-dioxan-2-yl)methyl]thio}-1-(4-fluorophenyl)-4-oxoazetidin-2-yl]phenoxy}acetate tert-Butyl (4-{(1S,2R)-2-{[(5,5-dimethyl-2-phenyl-1,3-dioxan-2-yl)methyl]thio}-1-[(4-fluorophenyl)amino]-3-oxo-3-[(4S)-2-oxo-4-phenyl-1,3-oxazolidin-3-yl]propyl}phenoxy)acetate (2.6 g, 3.4 mmol) was dissolved in dry toluene (250 ml) and heated to 90° C. under inert atmosphere. N,O-Bis(trimethylsilyl)acetamide (BSA, 2.5 ml, 10.3 mmol) was added and the mixture was stirred at 90° C. for one hour. The mixture was cooled to 45° C. and tetrabutylammonium fluoride (TBAF, cat., 0.5 g) was added. The mixture was stirred at 45° C. for two hours. The mixture was concentrated under reduced pressure and purified by flash-chromatography (hexane:EtOAc 7:1). This afforded 0.65 g (31%) of the title compound as a yellow solid. $^1$H-NMR (CDCl$_3$, 200 MHz): δ 0.6 (s, 3H), 1.2 (s, 3H), 1.5 (s, 9H), 2.9-3.1 (q, broad, 2H), 3.4 (q, 4H), 4.0 (s, 1H), 4.5 (s, 2H), 4.8 (s, 1H), 6.9-7.0 (m, 4H), 7.2-7.3 (m, 5H), 4.3-4.4 (m, 4H).

Method 27

(4-{2R,3R)-1-(4-Fluorophenyl)-4-oxo-3-[(2-oxo-2-phenylethyl)thio]azetidin-2-yl}phenoxy)acetic acid tert-butyl {4-[(2R,3R)-3-{[(5,5-dimethyl-2-phenyl-1,3-dioxan-2-yl)methyl]thio}-1-(4-fluorophenyl)-4-oxoazetidin-2-yl]phenoxy}acetate (1.34 g, 2.21 mmol) was dissolved in formic acid (20 ml) and stirred for 90 minutes. The mixture was concentrated under reduced pressure (temperature <30° C.). The crude oil was purified by flash-chromatography (hexane:acetone:formic acid 60:40:0.1) to afford 0.7 g (68%) of the title compound as a pale yellow solid. $^1$NMR(CDCl$_3$, 200 MHz): δ 4.15 (d, 1H), 4.22 (d, 2H), 4.71 (s, 2H), 4.91 (d, 1H), 6.92-7.00 (m, 4H), 7.24-7.30 (m, 4H), 7.46-7.63 (m, 3H), 7.94-7.99 (d, 2H). MS (CI) M/z: 464.2 (M–1).

Method 28

Ethyl {[2-(4-methoxyphenyl)-5,5-dimethyl-1,3-dioxan-2-yl]methyl}thio)acetate Ethyl {[2-(4-methoxyphenyl)-2-oxoethyl]thio}acetate (9.57 g, 35.7 mmol) was dissolved in benzene (250 ml). 2,2-Dimethyl-1,3-propanediol (29.7 g, 0.29 mol) and p-toluene sulfonic acid (500 mg) were added. The mixture was stirred at reflux in a Dean-Stark apparatus for three hours and at room temperature overnight. The mixture was concentrated under reduced pressure. $CH_2Cl_2$ was added and the solution was washed twice with $H_2O$ and with brine. The organic phase was dried ($MgSO_4$) and filtered. Concentration under reduced pressure afforded a crude oil which was purified by flash-chromatography (hexane:EtOAc 7:1) to afford 5.95 g (47%) of the title compound as a colorless oil. $^1$H-NMR ($CDCl_3$, 200 MHz): δ 0.6 (s, 3H), 1.2-1.4 (m, 6H), 3.0 (s, 2H), 3.2 (s, 2H), 3.4 (s, 4H), 3.8 (s, 3H), 4.2 (q, 2H), 6.9 (d, 2H), 7.4 (d, 2H).

Method 29

({[2-(4-Methoxyphenyl)-5,5-dimethyl-1,3-dioxan-2-yl]methyl}thio)acetic acid

Ethyl ({[2-(4-methoxyphenyl)-5,5-dimethyl-1,3-dioxan-2-yl]methyl}thio)acetate (5.95 g, 16.8 mmol) was dissolved in THF (75 ml) and cooled to 0° C. LiOH (2.11 g, 50.4 mmol) in water (40 ml) was added and the mixture was stirred for 90 minutes. Water was added and the mixture was extracted twice with diethyl ether. The aqueous layer was acidified using 2M HCl until pH=4 and extracted twice with $CH_2Cl_2$. The combined $CH_2Cl_2$ layers were dried ($Na_2SO_4$) and concentrated under reduced pressure to afford 5.4 g (>98%) of the title compound as a white solid. $^1$H-NMR ($CDCl_3$, 200 MHz): δ 0.6 (s, 3H), 1.4 (s, 3H), 3.0 (s, 2H), 3.4 (s, 2H), 3.5 (s, 4H), 3.9 (s, 3H), 6.9 (d, 2H), 7.4 (d, 2H).

Method 30

(4S)-3-[({[2-(4-Methoxyphenyl)-5,5-dimethyl-1,3-dioxan-2-yl]methyl}thio)acetyl]-4-phenyl-1,3-oxazolidin-2-one ({[2-(4-Methoxyphenyl)-5,5-dimethyl-1,3-dioxan-2-yl]methyl}thio)acetic acid (5.4 g, 16.5 mmol) was dissolved in dry $CH_2Cl_2$ (80 ml) and cooled to 0° C. N,N'-dicyclohexylcarbodiimide (DCC, 3.76 g; 18.2 mmol) in 20 ml of $CH_2Cl_2$ and 4-(dimethylamino)pyridine (DMAP, 4.04 g, 33.1 mmol) were added and the mixture was stirred at 0° C. for 30 minutes. (S)-(+)-4-Phenyl-2-oxazolidinone (2.69 g, 16.5 mmol) was added and the mixture was stirred at room temperature for 17 h. The mixture was filtered, concentrated under reduced pressure and purified by flash-chromatography (hexane:EtOAc 4:1 then 2:1). This afforded 5.69 g (73%) of the title compound as a white solid. $^1$H-NMR ($CDCl_3$, 200 MHz): δ 0.6 (s, 3H), 1.3 (s, 3H), 2.8 (s, 2H), 3.4 (s, 4H), 3.8 (s, 2H), 3.8 (s, 3H), 4.3 (dd, 1H), 4.7 (t, 1H), 5.4 (dd, 1H), 6.9 (d, 2H), 7.3 (m, 7H).

Method 31 tert-Butyl (4-{(1S,2R)-1-[(4-fluorophenyl)amino]-2-({[2-(4-methoxyphenyl)-5,5-dimethyl-1,3-dioxan-2-yl]methyl}thio)-3-oxo-3-[(4S)-2-oxo-4-phenyl-1,3-oxazolidin-3-yl]propyl}phenoxy)acetate Tetraisopropyl orthotitanate (0.31 ml, 1.06 mmol) was added to a solution of $TiCl_4$ (1M in $CH_2Cl_2$, 3.18 ml, 3.18 mmol) in $CH_2Cl_2$ (50 ml) at 0° C. under inert atmosphere. The mixture was stirred for ten minutes. (4S)-3-[({[2-(4-Methoxyphenyl)-5,5-dimethyl-1,3-dioxan-2-yl]methyl}thio)acetyl]-4-phenyl-1,3-oxazolidin-2-one (2.00 g, 4.24 mmol) in dry $CH_2Cl_2$ (50 ml) was added dropwise over 20 minutes. The mixture was stirred for ten minutes. tert-Butyl (4-{[(4-fluorophenyl)imino]methyl}phenoxy)acetate (2.79 g, 8.48 mmol) in dry $CH_2Cl_2$ (50 ml) was added dropwise over 30 minutes. The mixture was cooled to −30° C. and stirred for 20 minutes. Ethyl diisopropyl amine (1.45 ml, 8.48 mmol) in 10 ml dry $CH_2Cl_2$ was added dropwise over ten minutes and the mixture was stirred at −30° C. for five hours. The mixture was cooled to −78° C. Isopropanol (60 ml) was added and the temperature was allowed to rise overnight. $H_2O$ (100 ml) was added and the mixture was stirred for 20 minutes and extracted twice with diethyl ether. The combined organic layers were washed with water, dried ($MgSO_4$) and concentrated under reduced pressure. Purification by flash-chromatography (hexane:EtOAc 3:1) afforded 2.00 g (59%) of the title compound as a yellow solid. $^1$H-NMR ($CDCl_3$, 200 MHz): δ 0.6 (s, 3H), 1.3 (s, 3H), 1.5 (s, 9H), 2.6-2.9 (m, 2H), 3.3-3.5 (m, 4H), 3.8 (s, 3H), 4.1-4.3 (m, 2H), 4.5 (s, 2H), 4.6-4.8 (m, 2H), 5.0-5.4 (s, broad, 1H), 5.4 (m, 1H), 5.7 (d, 1H), 6.4 (m, 2H), 6.6-6.8 (m, 4H), 6.8-7.0 (m, 4H), 7.1-7.4 (m, 7H).

Method 32 tert-Butyl {4-[(2R,3R)-1-(4-fluorophenyl)-3-({[2-(4-methoxyphenyl)-5,5-dimethyl-1,3-dioxan-2-yl]methyl}thio)-4-oxoazetidin-2-yl]phenoxy}acetate tert-Butyl (4-{(1S,2R)-1-[(4-fluorophenyl)amino]-2-({[2-(4-methoxyphenyl)-5,5-dimethyl-1,3-dioxan-2-yl]methyl}thio)-3-oxo-3-[(4S)-2-oxo-4-phenyl-1,3-oxazolidin-3-yl]propyl}phenoxy)acetate (2.0 g, 2.5 mmol) was dissolved in dry toluene (200 ml) and heated to 90° C. under inert atmosphere. N,O-Bis(trimethylsilyl)acetamide (BSA, 1.8 ml, 7.5 mmol) was added and the mixture was stirred at 90° C. for one hour. The mixture was cooled to 45° C. and tetrabutylammonium fluoride (TBAF, 150 mg) was added and the mixture was stirred at 45° C. for two hours. The mixture was concentrated under reduced pressure and filtered through a short column of silica (hexane:EtOAc 4:1). Purification of the crude oil by flash-chromatography (hexane:EtOAc 5:1) gave 0.65 g (41%) of the title compound as a yellow solid. $^1$H-NMR ($CDCl_3$, 200 MHz): δ 0.6 (s, 3H), 1.3 (s, 3H), 1.5 (s, 9H), 3.0-3.2 (m, 2H), 3.3-3.5 (m, 4H), 3.8 (s, 3H), 4.0 (d, 1H), 4.5 (s, 2H), 4.8 (d, 1H), 6.8-7.0 (m, 6H), 7.2-7.4 (m, 6H).

Method 33

[4-((2R,3R)-1-(4-Fluorophenyl)-3-{[2-(4-methoxyphenyl)-2-oxoethyl]thio}-4-oxoazetidin-2-yl)phenoxy]acetic acid tert-Butyl {4-[(2R,3R)-1-(4-fluorophenyl)-3-({[2-(4-methoxyphenyl)-5,5-dimethyl-1,3-dioxan-2-yl]methyl}thio)-4-oxoazetidin-2-yl]phenoxy}acetate (0.65 g, 1.02 mmol) was dissolved in formic acid (10 ml) and stirred for 90 minutes. The mixture was concentrated under reduced pressure (temperature <30° C.) and the crude oil was purified by flash-chromatography (hexane:acetone:formic acid 60:40:0.1) to afford 0.45 g (88%) of the title compound as a pale yellow solid. $^1$H-NMR ($CDCl_3$, 200 MHz): δ 3.9 (s, 3H), 4.1 (d, 1H), 4.1 (s, 2H), 4.7 (s, 2H), 4.9 (d, 1H), 6.9-7.1 (m, 6H), 7.2-7.4 (m, 4H), 7.9-8.0 (d, 2H). MS (CI) M/z: 494.1 (M$^+$–1), 495.1 (M$^+$)

Method 34

Ethyl (([5,5-dimethyl-2-(4-methylphenyl)-1,3-dioxan-2-yl]methyl}thio)acetate

Ethyl {[2-(4-methylphenyl)-2-oxoethyl]thio}acetate (12.2 g, 48.4 mmol) was dissolved in benzene (350 ml). 2,2-Dimethyl-1,3-propanediol (40.3 g, 0.387 mol) and p-toluene sulfonic acid (1 g) were added. The mixture was stirred at reflux in a Dean-Stark apparatus for two hours, cooled and concentrated under reduced pressure. CH$_2$Cl$_2$ was added and the organic phase was washed twice with brine and dried (MgSO$_4$). Filtration and concentration under reduced pressure afforded a crude oil, which was purified by flash-chromatography (hexane:EtOAc 8:1) to afford 10.0 g (61%) of the title compound as a clear oil.
$^1$H-NMR (CDCl$_3$, 200 MHz): δ 0.6 (s, 3H), 1.2-1.4 (m, 6H), 2.4 (s, 3H), 3.0 (s, 2H), 3.2 (s, 2H), 3.4-3.5 (m, 4H), 4.2 (q, 2H), 7.2-7.4 (m, 4H).

Method 35

({[5,5-Dimethyl-2-(4-methylphenyl)-1,3-dioxan-2-yl]methyl}thio)acetic acid

Ethyl ({[5,5-dimethyl-2-(4-methylphenyl)-1,3-dioxan-2-yl]methyl}thio)acetate (10.1 g, 29.8 mmol) was dissolved in THF (150 ml) and cooled to 0° C. LiOH (3.76 g, 89.5 mmol) in water (50 ml) was added and the mixture was stirred for two hours at room temperature. The mixture was concentrated under reduced pressure. Water was added and the mixture was extracted with diethyl ether. The aqueous layer was acidified using 2M HCl to pH 3 and extracted twice with CH$_2$Cl$_2$. The combined CH$_2$Cl$_2$ layers were dried (Na$_2$SO$_4$) and concentrated under reduced pressure to afford 8.7 g (94%) of the title compound as a white solid. $^1$H-NMR(CDCl$_3$, 200 MHz): δ 0.6 (s, 3H), 1.2 (s, 3H), 2.4 (s, 3H), 3.0 (s, 2H), 3.4 (s, 2H), 3.4 (s, 4H), 7.2-7.4 (m. 4H).

Method 36

(4S)-3-[({[5,5-Dimethyl-2-(4-methylphenyl)-1,3-dioxan-2-yl]methyl}thio)acetyl]-4-phenyl-1,3-oxazolidin-2-one ({[5,5-Dimethyl-2-(4-methylphenyl)-1,3-dioxan-2-yl]methyl}thio)acetic acid (8.7 g, 28.0 mmol) was dissolved in dry CH$_2$Cl$_2$ (120 ml) and cooled to 0° C. N,N'-Dicyclohexylcarbodiimide (DCC, 6.35 g, 30.8 mmol) in 30 ml of CH$_2$Cl$_2$ and 4-(dimethylamino)pyridine (DMAP, 6.85 g, 56.1 mmol) were added. The mixture was stirred at 0° C. for 30 minutes. (S)-(+)-4-Phenyl-2-oxazolidinone (4.57 g, 28.0 mmol) was added and the mixture was stirred at room temperature for 19 h. The mixture was filtered, concentrated under reduced pressure and purified by flash-chromatography (hexane:EtOAc 5:1 then 4:1). This afforded 7.07 g (55%) of the title compound as a white solid. $^1$H-NMR (CDCl$_3$, 200 MHz): δ 0.6 (s, 3H), 1.2 (s, 3H), 2.4 (s, 3H), 2.8 (s, 2H), 3.4 (s, 4H), 3.8 (s, 2H), 4.3 (dd, 1H), 4.7 (t, 1H), 5.4 (dd, 1H), 7.2-7.5 (m, 9H).

Method 37 tert-Butyl (4-{(1S,2R)-2-({[5,5-dimethyl-2-(4-methylphenyl)-1,3-dioxan-2-yl]methyl}thio)-1-[(4-fluorophenyl)amino]-3-oxo-3-[(4S)-2-oxo-4-phenyl-1,3-oxazolidin-3-yl]propyl}phenoxy)acetate Tetraisopropyl orthotitanate (0.37 ml, 1.23 mmol) was added to a solution of TiCl$_4$ (1M in CH$_2$Cl$_2$, 3.3 ml, 3.3 mmol) in CH$_2$Cl$_2$ (50 ml) at 0° C. under inert atmosphere. The mixture was stirred for ten minutes. (4S)-3-[({[5,5-Dimethyl-2-(4-methylphenyl)-1,3-dioxan-2-yl]methyl}thio)acetyl]-4-phenyl-1,3-oxazolidin-2-one (2.0 g, 4.4 mmol) in dry CH$_2$Cl$_2$ (50 ml) was added dropwise over 20 minutes and the mixture was stirred for ten minutes. tert-Butyl (4-{[(4-fluorophenyl)imino]methyl}phenoxy)acetate (2.9 g, 8.8 mmol) in dry CH$_2$Cl$_2$ (50 ml) was added dropwise over 30 minutes. The mixture was cooled to –30° C. and stirred for 20 minutes. Ethyl diisopropyl amine (1.5 ml, 8.8 mmol) in 10 ml dry CH$_2$Cl$_2$ was added dropwise over ten minutes. The mixture was stirred at –30° C. for four hours. The mixture was cooled to –78° C. and isopropanol (60 ml) was added. The temperature was allowed to reach room temperature over two hours. H$_2$O (100 ml) was added and the mixture was stirred for 20 minutes and extracted twice with diethyl ether. The combined organic layers were washed with water, dried (MgSO$_4$) and concentrated under reduced pressure. Purification by flash-chromatography (hexane:EtOAc 5:1 then 4:1) afforded 2.55 g (74%) of the title compound as a white solid. $^1$H-NMR (CDCl$_3$, 200 MHz): δ 0.6 (s, 3H), 1.3 (s, 3H), 1.5 (s, 9H), 2.4 (s, 3H), 2.6-2.9 (m, 2H), 3.3-3.5 (m, 4H), 4.1-4.3 (m, 1H), 4.5 (s, 2H), 4.6-4.8 (m, 2H), 5.0-5.3 (s, broad, 1H), 5.2 (m, 1H), 5.7 (d, 1H), 6.4 (m, 2H), 6.6-6.8 (m, 4H), 6.9 (m, 2H), 7.1-7.4 (m, 9H).

Method 38 tert-Butyl {4-[(2R,3R)-3-({[5,5-dimethyl-2-(4-methylphenyl)-1,3-dioxan-2-yl]methyl}thio)-1-(4-fluorophenyl)-4-oxoazetidin-2-yl]phenoxy}acetate tert-Butyl (4-{(1S,2R)-2-({[5,5-dimethyl-2-(4-methylphenyl)-1,3-dioxan-2-yl]methyl}thio)-1-[(4-fluorophenyl)amino]-3-oxo-3-[(4S)-2-oxo-4-phenyl-1,3-oxazolidin-3-yl]propyl}phenoxy)acetate (2.55 g, 3.25 mmol) was dissolved in dry toluene (250 ml) and heated to 90° C. under inert atmosphere. N,O-Bis(trimethylsilyl)acetamide (BSA, 2.38 ml, 9.75 mmol) was added and the mixture was stirred at 90° C. for one hour. The mixture was cooled to 45° C. and tetrabutylammonium fluoride (TBAF, 0.25 g) was added and the mixture was stirred at 45° C. for one hour. The mixture was concentrated under reduced pressure and purified by flash-chromatography (hexane:EtOAc 6:1). This afforded 1.06 g (52%) of the title compound as a white solid. $^1$H-NMR (CDCl$_3$, 200 MHz): δ 0.6 (s, 3H), 1.3 (s, 3H), 1.5 (s, 9H), 2.4 (s, 3H), 3.0-3.2 (m, 2H), 3.3-3.5 (m, 4H), 3.9 (d, 1H), 4.5 (s, 2H), 4.8 (d, 1H), 6.8-7.0 (m, 6H), 7.1-7.4 (m, 6H).

Method 39

[4-((2R,3R)-1-(4-Fluorophenyl)-3-{[2-(4-methylphenyl)-2-oxoethyl]thio}-4-oxoazetidin-2-yl)phenoxy] acetic acid tert-Butyl {4-[(2R,3R)-3-({[5,5-dimethyl-2-(4-methylphenyl)-1,3-dioxan-2-yl]methyl}thio)-1'-(4-fluorophenyl)-4-oxoazetidin-2-yl]phenoxy}acetat (1.04 g, 1.67 mmol)

was dissolved in formic acid (20 ml) and stirred for 60 minutes. The mixture was concentrated under reduced pressure (temperature <30° C.) and the crude oil was purified by flash-chromatography (hexane:acetone:formic acid 60:40:0.1) to afford 0.72 g (90%) of the title compound as a pale yellow solid. $^1$H-NMR (CDCl$_3$, 200 MHz): δ 2.4 (s, 3H), 4.1 (d, 1H), 4.2 (s, 2H), 4.7 (s, 2H), 4.9 (d, 1H), 6.9 (m, 6H), 7.2-7.4 (m, 4H), 7.8 (d, 2H). MS (CI) M/z: 478.1 (M$^+$–1).

Method 40 tert-Butyl (4-{(E)-[(4-chlorophenyl)imino]methyl}phenoxy)acetate

A suspension of NaH (60% in mineral oil, 3.69 g, 92.2 mmol) in dry DMF (70 ml) was cooled to 0° C. A solution of 4-hydroxybenzaldehyde (10.0 g, 82.0 mmol) in dry DMF (35 ml) was added dropwise. The mixture was stirred at 0° C. for 40 minutes. tert-Butyl bromoacetate (12.1 ml, 82.5 mmol) was added and the mixture was stirred at room temperature for 17 h. The mixture was concentrated under reduced pressure. Diethyl ether was added and the mixture was washed with 10% NH$_4$Cl, water and brine. The organic phase was dried (MgSO$_4$), concentrated under reduced pressure and purified by flash-chromatography (10%-20% EtOAc in hexane). This gave tert-butyl (4-formylphenoxy)acetate (17.4 g, 73.4 mmol, 90% yield) as an colourless oil. This intermediate was dissolved in dry toluene (120 ml) and 4-chloroaniline (9.37 g, 73.4 mmol) was added. The mixture was refluxed in a Dean-Stark apparatus for 20 h, cooled and concentrated under reduced pressure. Hexane was added and the formed precipitate was filtered, washed twice with cold hexane and dried. This afforded 20.0 g (79%) of the title compound as a yellow solid. $^1$H-NMR (CDCl$_3$, 200 MHz): δ 1.5 (s, 9H), 4.6 (s, 2H), 7.0 (d, 2H), 7.2 (d, 2H), 7.4 (d, 2H), 7.8 (d, 2H), 8.4 (s, 1H). MS (CI) M/z: 368.0 (M$^+$+Na, 100), 369.0 (20), 370.0 (30), 371.0 (10).

Method 41

Ethyl ({[2-(4-chlorophenyl)-5,5-dimethyl-1,3-dioxan-2-yl]methyl}thio)acetate

Ethyl {[2-(4-chlorophenyl)-2-oxoethyl]thio}acetate (8.15 g, 29.9 mmol) was dissolved in toluene (165 ml). 2,2-Dimethyl-1,3-propanediol (24.8 g, 238 mmol) and p-toluene sulfonic acid (300 mg) were added. The mixture was stirred at reflux in a Dean-Stark apparatus for 2.5 h and concentrated under reduced pressure. The crude product was dissolved in CH$_2$Cl$_2$. The mixture was washed with H$_2$O (3×), brine, dried (Na$_2$SO$_4$) and concentrated under reduced pressure. The residue was purified by flash-chromatography (Hexane:EtOAc 9:1) to give 3.36 g (31%) of the title compound as an yellow oil. MS (CI) M/z: 381.0 (M$^+$+Na, 100), 382.0 (15), 383.0 (30), 384 (5)

Method 42

({[2-(4-Chlorophenyl)-5,5-dimethyl-1,3-dioxan-2-yl]methyl}thio)acetic acid

Ethyl ({[2-(4-chlorophenyl)-5,5-dimethyl-1,3-dioxan-2-yl]methyl}thio)acetate (3.36 g, 9.36 mmol) was dissolved in THF (45 ml) and cooled to 0° C. LiOH (0.79 g, 18.8 mmol) in water (12 ml) was added and the mixture was stirred for 18 h at room temperature. The solvents were evaporated. The crude product was extracted between water and diethyl ether. The aqueous layer was acidified using 2M HCl to pH 6 and extracted twice with CH$_2$Cl$_2$. The combined CH$_2$Cl$_2$ layers were dried (Na$_2$SO$_4$) and concentrated under reduced pressure to afford 2.98 g (96%) of the title compound as an yellow oil. $^1$H-NMR (CDCl$_3$, 300 MHz): δ 0.62 (s, 3H), 1.34 (s, 3H), 2.95 (s, 2H), 3.34 (s, 2H), 3.45 (s, 4H), 7.4 (m, 4H)

Method 43

(4S)-3-[({[2-(4-Chlorophenyl)-5,5-dimethyl-1,3-dioxan-2-yl]methyl}thio)acetyl]-4-phenyl-1,3-oxazolidin-2-one ({[2-(4-Chlorophenyl)-5,5-dimethyl-1,3-dioxan-2-yl]methyl}thio)acetic acid (2.00 g, 6.05 mmol) was dissolved in dry CH$_2$Cl$_2$ (45 ml) and cooled to 0° C. N,N'-Dicyclohexyl-carbodiimide (DCC, 1.43 g, 6.93 mmol) and 4-(dimethylamino)pyridine (DMAP, 1.70 g, 10.4 mmol) were added and the mixture was stirred at 0° C. for 20 minutes. (S)-(+)-4-Phenyl-2-oxazolidinone (1.40 g, 11.5 mmol) was added and the mixture was stirred at room temperature for 70 h. The mixture was filtered, concentrated under reduced pressure and purified by flash-chromatography (20%-30% EtOAc in hexane). This afforded 1.27 g (44%) of the title compound as a white solid. $^1$H-NMR (CDCl$_3$, 300 MHz): δ 0.62 (s, 3H), 1.34 (s, 3H), 2.78 (s, 2H), 3.42 (s, 4H), 3.85 (s, 2H), 4.27-4.33 (dd, 1H), 4.69-4.78 (t, 1H), 5.34-5.42 (dd, 1H), 7.29-7.38 (m, 9H).

Method 44 tert-Butyl (4-{(1S,2R)-1-[(4-chlorophenyl)amino]-2-({[2-(4-chlorophenyl)-5,5-dimethyl 1,3-dioxan-2-yl]methyl}thio)-3-oxo-3-[(4S)-2-oxo-4-phenyl-1,3-oxazolidin-3-yl]propyl}phenoxy)acetate Tetraisopropyl orthotitanate (0.23 ml, 0.77 mmol) was added to a solution of TiCl$_4$ (1M in CH$_2$Cl$_2$, 2.25 ml, 2.25 mmol) in CH$_2$Cl$_2$ (22 ml) at 0° C. under inert atmosphere. The mixture was stirred for ten minutes. (4S)-3-[({[2-(4-Chlorophenyl)-5,5-dimethyl-1,3-dioxan-2-yl]methyl}thio)acetyl]-4-phenyl-1,3-oxazolidin-2-one (1.44 g, 3.03 mmol) in dry CH$_2$Cl$_2$ (25 ml) was added dropwise over 45 minutes and the mixture was stirred for ten minutes. tert-Butyl (4-{(E)-[(4-chlorophenyl)imino]methyl}phenoxy)acetate (2.09 g, 6.04 mmol) in dry CH$_2$Cl$_2$ (25 ml) was added dropwise over 80 minutes. The mixture was cooled to –40° C. and stirred for 20 minutes. Ethyl diisopropyl amine (1.03 ml, 6.02 mmol) was added dropwise over 40 minutes and the mixture was stirred at –40° C. for ten minutes. The mixture was cooled to –78° C. and isopropanol (80 ml) was added. The temperature was allowed to reach room temperature over three hours. NH$_4$Cl (10%, 80 ml) was added and the mixture was stirred for 35 minutes. Brine (200 ml) was added and the mixture was extracted twice with 400 ml diethyl ether. The combined organic layers were dried (MgSO$_4$) and concentrated under reduced pressure. Purification by flash-chromatography (10%-20% EtOAc in hexane) afforded 1.69 g (65%) of the title compound as a white solid. $^1$H-NMR (CDCl$_3$, 200 MHz): δ 0.65 (s, 3H), 1.3 (s, 3H), 1.5 (s, 9H), 2.6-2.9 (m, 2H), 3.4 (m, 4H), 4.2 (m, 1H), 4.5 (s, 2H), 4.64-8 (m, 2H), 5.3 (m, 1H), 5.7 (d, 1H), 6.4 (m, 2H), 6.7-7.4 (m, 15H).

Method 45 tert-Butyl {4-[(2R,3R)-1-(4-chlorophenyl)-3-({[2-(4-chlorophenyl)-5,5-dimethyl-1,3-dioxan-2-yl]methyl}thio)-4-oxoazetidin-2-yl]phenoxy}acetate tert-Butyl (4-{(1S,2R)-1-[(4-chlorophenyl)amino]-2-({[2-(4-chlorophenyl)-5,5-dimethyl-1,3-dioxan-2-yl]methyl}thio)-3-oxo-3-[(4S)-2-oxo-4-phenyl-1,3-oxazolidin-3-yl]propyl}phenoxy)acetate (1.69 g, 2.06 mmol) was dissolved in dry toluene (140 ml) and heated to 90° C. under inert atmosphere. N,O-Bis(trimethylsilyl)acetamide (BSA, 1.48 ml, 6.05 mmol) was added and the mixture was stirred at 90° C. for one hour. The mixture was cooled to 45° C. and tetrabutylammonium fluoride (TBAF, 0.1 g) was added and the mixture was stirred at 45° C. for one hour and at room temperature overnight. The mixture was concentrated under reduced pressure and purified by flash-chromatography (10%-20% EtOAc in hexane). This afforded 0.84 g (61%) of the title compound as a white solid. $^1$H-NMR (CDCl$_3$, 200 MHz): δ 0.6 (s, 3H), 1.2 (s, 3H), 1.5 (s, 9H), 2.9-3.1 (t, broad, 2H), 3.4 (s, 4H), 4.0 (s, 1H), 4.5 (s, 2H), 4.8 (s, 1H), 6.9 (d, 2H), 7.2-7.4 (m, 10H).

Method 46

[4-((2R,3R)-1-(4-Fluorophenyl)-4-oxo-3-{[2-oxo-2-(4-pentylphenyl)ethyl]thio}azetidin-2-yl)phenoxy]acetic acid tert-Butyl (4-{(2R,3R)-1-(4-fluorophenyl)-3-[(3-nitropyridin-2-yl)dithio]-4-oxoazetidin-2-yl}phenoxy)acetate (0.20 g, 0.36 mmol) was dissolved in acetone (10 ml) at room temperature. Water (2.5 ml) and triphenyl phosphine (0.094 g, 0.36 mmol) were added. The mixture was stirred at room temperature for 30 minutes and then concentrated under reduced pressure to afford the crude thiol as a brown oil. This crude thiol was immediately dissolved in CH$_2$Cl$_2$ (10 ml) and 2-bromo-1-(4'-penthyl phenyl)ethan-1-one (0.19 g, 0.72 mmol) was added, followed by Et$_3$N (0.10 ml, 0.72 mmol). The mixture was stirred at room temperature for 20 hours, concentrated under reduced pressure and purified by flash-chromatography (Hex:EtOAc 4:1). This afforded 0.21 g of a mixture of tert-butyl [4-((2R,3R)-1-(4-fluorophenyl)-4-oxo-3-{[2-oxo-2-(4-pentylphenyl)ethyl]thio}azetidin-2-yl)phenoxy]acetate and 2-[(3-nitropyridin-2-yl)thio]-1-(4-pentylphenyl)ethanone. This mixture was dissolved in HCOOH (10 ml) and stirred at room temperature for 18 hours. Concentration under reduced pressure and purification by flash-chromatography (hex: acetone: HCOOH 60:40:0.1) afforded 0.11 g (61%) of the desired compound as a pale yellow solid.

$^1$H-NMR (CD$_3$Cl, 300 MHz): δ 0.8-1.0 (m, 3H), 1.2-1.5 (m, 4H), 1.6-1.8 (m, 2H), 2.7 (t, 2H), 4.1 (d, 1H), 4.2 (s, 2H), 4.7 (s, 2H), 4.9 (d, 1H) 6.9-7.1 (m, 4H), 7.2-7.4 (m, 6H), 7.9 (d, 2H).

Method 47

Sodium (2R)-2-amino-4-cyclohexylbutanoate

Ethyl (2R)-2-amino-4-cyclohexylbutanoate hydrochloride (4.00 g, 18.75 mmol) was dissolved in MeOH/Water (10/5 ml). Sodium hydroxide (1.50 g, 37.50 mmol) was added. The reaction mixture was stirred for 1 h and concentrated to give the title compound as a colourless solid (containing 100 mol % of sodium chloride). $^1$H NMR [(CD$_3$)$_2$SO), 400 MHz] δ0.83-0.97 (m, 2H), 1.10-1.33 (m, 6H), 1.48-1.78 (m, 7H), 3.15 (dd, 1H).

Method 48

N-{[4-((2R,3R)-1-(4-chlorophenyl)-3-{[2-(4-chlorophenyl)-2-oxoethyl]thio}-4-oxoazetidin-2-yl)phenoxy]acetyl}glycine

[4-((2R,3R)-1-(4-Chlorophenyl)-3-{[2-(4-chlorophenyl)-2-oxoethyl]thio}-4-oxoazetidin-2-yl)phenoxy]acetic acid, 302.1 mg, 0.585 mmol) was dissolved in DCM (6 ml). N-Methylmorpholine (190 µl, 1.728 mmol) and tert-butyl glycinate hydrochloride (133.4 mg, 0.80 mmol) were added. After 10 minutes, TBTU (224.3 mg, 0.67 mmol) was added and the reaction mixture was stirred for 60 h. The intermediate tert-butylester of the title compound was confirmed. M/z: 626.88 (M−H). DCM (10 ml) and water (15 ml) were added and the mixture was acidified to pH of 3 using KHSO$_4$ (2M). The organic phase was washed with water (2×15 ml). The combined aqueous phases were extracted with DCM (10 ml), dried over Na$_2$SO$_4$, filtered and concentrated. A solution of the residue (500 mg) in DCM (10 ml) and TFA (4 ml) was stirred overnight. The solvent was removed under reduced pressure. Toluene was added and evaporated to assist the removal of TFA. The residue was purified with preparative HPLC on a C8 column. A gradient from 20 to 50% MeCN in 0.1M ammonium acetate buffer was used as eluent. After lyophilisation, the title compound was obtained as a white solid (166.9 mg, 50%). H-NMR (400 MHz, DMS-d$_6$): 3.51 (d, 2H), 4.33 (d, 1H), 4.34 (s, 1H), 4.36 (s, 1H), 4.47 (s, 2H), 5.17 (d, 1H), 6.96 (d, 2H), 7.16-7.21 (m, 2H), 7.35 (d, 4H), 7.54-7.59 (m, 2H), 7.83-7.90 (brs, 1H), 7.91-7.95 (m, 2H). M/z: 571.04 (M−H) and 572.88 (M+H).

Method 49

(2R)-cyclohexyl[(N-{[4-((2R,3R)-1-(4-fluorophenyl)-3-{[2-(4-fluorophenyl)-2-oxoethyl]thio}-4-oxoazetidin-2-yl)phenoxy]acetyl}glycyl)amino]acetic acid TBTU (0.0092 g, 0.029 mmol) was added to a mixture of 3-(R)-4-(R)-1-(4-Fluorophenyl)-3-[(4-fluorobenzoyl)methylthio]-4-{4-[N-(carboxymethyl) carbamoylmethoxy]phenyl}azetidin-2-one (0.016 g, 0.030 mmol) and N-methylmorpholin (0.101 ml, 0.98 mmol) in DMF (2 ml). The mixture was stirred overnight under N$_2$-atmosphere. Additional TBTU (0.0092 g, 0.029 mmol) was added and the mixture was stirred at 35° C. for 2 h. (2R)-amino(cyclohexyl)acetic acid hydrochloride (0.0068 g, 0.035mmol) was added. The mixture was stirred at 35° C. for 2 h and at room temperature overnight. The solvent was removed under reduced pressure and the residue was purified by preparative HPLC on a Kromasil C8-column using a gradient of 5-100% MeCN in 0.15% trifluoroacetic acid buffer as eluent. The solvent was removed under reduced pressure and 0.009 g (47%) of the title product was obtained.

M/z 680.01

Method 50 tert-butyl N$^2$-[(benzyloxy)carbonyl]-N$^5$-(tert-butoxycarbonyl)-D-ornithinate N$^2$-[(benzyloxy)carbonyl]-N$^5$-(tert-butoxycarbonyl)-D-ornithine (1 g, 2.73 mmole) was dissolved in toluene (5 mL) and kept at 100° C. N,N-dimethylformamide di-tert-butyl acetal (1.5 mL, 6.25 mmole) was added drop wise. After 40 minutes the mixture was allowed to cool down to room temperature and kept there for three days. The organic layer was washed with NaHCO$_3$-solution and brine, dried (Na$_2$SO$_4$), filtered and the solvent was removed under reduced pressure. 0.67 g (58%) of the desired product was obtained.

NMR (500 MHz, CD3COOD) 1.35-1.71 (m, 21H), 1.72-1.85 (m, 1H), 3.06 (t, 2H), 4.05 (dd, 1H), 5.11 (ABq, 2H), 7.29-7.40 (m, 5H)

Method 51 tert-butyl N$^5$-(tert-butoxycarbonyl)-D-ornithinate tert-butyl N$^2$-[(benzyloxy)carbonyl]-N$^5$-(tert-butoxycarbonyl)-D-ornithinate (0.67 g, 1.83 mmole) and Pd on charcoal (95%, 0.115 g) were mixed in EtOH (95%, 20 mL) and stirred under H$_2$-atmosphere for 5 hours and 15 minutes. The mixture was filtered through Celite 521 and the solvent was evaporated under reduced pressure to give 0.45 g (85%) of the desired product.

NMR (500 MHz, CD3COOD) 1.41-1.76 (m22H), 3.07 (t, 2H), 3.32-3.36 (m 1H)

Method 52

Glycyl-3-cyclohexyl-D-alanine

N-(tert-butoxycarbonyl)glycine (2.0 g, 11.4 mmol) and DIPEA (4.0 g, 31 mmol) were dissolved in methylene chloride (25 ml). TBTU (4.1 g, 12.8 mmol) was added and the mixture was stirred for 15 min at room temperature. 3-cyclohexyl-D-alanine (2.1 g, 12.2 mmol) was added and the reaction mixture was stirred over night at room temperature. The reaction mixture was transferred to a separation funnel and was then extracted with a water/acetic acid solution (100 ml 5% acetic acid). The organic layer was separated and evaporated under reduced pressure. The residue was dissolved in formic acid (20 ml) and the mixture was stirred over night at 40° C. The formic acid was removed under reduced pressure. The residue was washed with water (50 ml) and then stirred in aceton (25 ml) for 1 h at room temperature. The solid material was filtered off and washed with aceton (20 ml). 530 mg (20%) of the title compound was obtained.

$^1$H-NMR, 300 MHz, CD3COOD): 0.8-1.9 (m, 13H), 3.9-4.1 (m, 2H), 4.55-4.65 (m, 1H).

Method 53

β,βdimethyl-D-phenylalanine trifluoroacetate

N-(tert-butoxycarbonyl)-b,b-dimethyl-D-phenylalanine tert-butyl ammonium salt (51.2 mg, 0.14 mmol) was dissolved in DCM (15 ml). Water (10 ml) was added and the mixture was acidified to pH 1 with HCl (1M). The organic phase was washed with water (3×10 ml) and the water phase extracted with DCM (3×10 ml). The solvent was removed under reduced pressure. The residue was dissolved in DCM (4 ml) and TFA (2.5 ml) was added and the mixture was stirred for 2 hours. The solvent was removed under reduced pressure and the residue was dried under vacuum overnight. The title compound was obtained as a white solid (36.1 mg, 85%). M/z: 194.18 (M+1).

Method 54

Glycyl-3-methyl-D-valine trifluoroacetate

To a 30° C. solution of N-(tert-butoxycarbonyl)glycine (0.450 g, 2.569 mmol) and N-methylmorpholine (1.30 g, 12.84 mmol) in CH$_2$Cl$_2$ (50 ml) was added TBTU (0.99 g, 3.08 mmol). After 1.5 h, D-tert-leucine (0.303 g, 2.31 mmol) was added. After 30 minutes, the reaction was quenched by the addition of water (1 ml). The mixture was concentrated and the residue was purified through preparative HPLC using an eluent of 0-40% CH$_3$CN in 0.1M NH$_4$OAc buffer. Pure fractions were collected and concentrated. To the residue were added CH$_2$Cl$_2$ (10 ml) and TFA (3 ml). Full conversion to the corresponding aminoacid was obtained after 30 minutes. The reaction mixture was concentrated to give the desired compound (0.359 g, 46%) as a colourless solid. $^1$H N [(CD$_3$)$_2$SO], 400 MHz] 0.94 (s, 9H), 3.60-3.67 (m, 2H), 4.16 (d, 1H), 7.90-8.00 (m, 3H), 8.47 (d, 1H).

Method 55

{14-[(2R,3R)-3-{[2-(4-tert-Butylphenyl)-2-oxoethyl]thio}-1-(4-fluorophenyl)-4-oxoazetidin-2-yl]phenoxy}acetic acid tert-Butyl (4-{(2R,3R)-1-(4-fluorophenyl)-3-[(3-nitropyridin-2-yl)dithio]-4-oxoazetidin-2-yl}phenoxy)acetate (0.20 g, 0.36 mmol) was dissolved in acetone (10 ml) at room temperature, then water (2.5 ml) and triphenyl phosphine (0.094 g, 0.36 mmol) was added. The mixture was stirred at room temperature for 15 minutes and then concentrated under reduced pressure to afford the crude thiol as a brown oil. This crude thiol was immediately dissolved in CH$_2$Cl$_2$ (8 ml) and 2-bromo-1-(4'-tert-butyl-phenyl)-ethan-1-one (0.15 g, 0.72 mmol) was added, followed by Et$_3$N (0.10 ml, 0.72 mmol). The mixture was stirred at room temperature for 1.5 hours, concentrated under reduced pressure and purified by flash-chromatography (Hex:EtOAc 4.1). This afforded 0.26 g of a mixture of tert-butyl {4-[(2R,3R)-3-{[2-(4-tert-butylphenyl)-2-oxoethyl]thio}-1-(4-fluorophenyl)-4-oxoazetidin-2-yl]phenoxy}acetate and 1-(4-tert-butylphenyl)-2-[(3-nitropyridin-2-yl)thio]ethanone. This mixture was dissolved in formic acid (10 ml) and stirred at room temperature for 17 hours. Concentration under reduced pressure and purification by flash-chromatography (hex:acetone:formic acid 70:30:0.1) afforded 0.08 g (43%) of the desired product as a white solid.

$^1$H-NMR (CD$_3$Cl, 200 MHz): δ 1.30 (s, 9H), 4.10 (s, 1H), 4.15 (s, 2H), 4.60 (s, 2H), 4.85 (s, 1H), 6.80-7.00 (m, 4H), 7.15-7.30 (m, 4H), 7.60-7.70 (m, 2H), 7.80-7.90 (m, 2H).

Method 56

N-({4-[(2R,3R)-3-{[2-(4-tert-Butylphenyl)-2-hydroxyethyl]thio}-1-(4-fluorophenyl)-4-oxoazetidin-2-yl]phenoxy}acetyl)glycyl-3-cyclohexyl-D-alanine To a solution of {4-[(2R,3R)-3-{[2-(4-tert-butylphenyl)-2-oxoethyl]thio}-1-(4-fluorophenyl)-4-oxoazetidin-2-yl]phenoxy}acetic acid (0.020 g, 0.038 mmol) and NMM (0.013 ml, 0.118 mmol) in DMF (3 ml) at RT was added TBTU (0.019 g, 0.059 mmol). After 90 min glycyl-3-cyclohexyl-D-alanine (0.009 g, 0.039 mmol) was added and the mixture was stirred for 18 h before the reaction was quenched by the addition of water (1 ml). The mixture was diluted with MeOH (1 ml) and NaBH4 (0.025 g, 0.661 mmol) was added. After 10 min the reaction was quenched by the addition of a 0.1M ammonium acetate buffer (2 ml) and most of the methanol was removed under reduced pressure. The remaining solution was purified by preparative HPLC using a gradient of 20-60% MeCN in a 0.1M ammonium acetate buffer as eluent. Freeze-drying of the pure fractions gave the desired product as a white solid (0.010 g, 36% yield).

ES-m/z: 733.2 (M−1)⁻. 1H NMR (DMSO, 500 MHz) δ: 0.70-0.93 (m, 2H), 1.00-1.35 (m, 13H), 1.35-1.71 (m, 7H), 2.84-2.96 (m, 2H), 3.72-3.80 (m, 2H), 4.12-4.22 (m, 1H), 4.22-4.28 (m, 1H), 4.50 (s, 2H), 4.60-4.72 (m, 1H), 4.98-5.03 (m, 1H), 6.94-7.01 (m, 2H), 7.09-7.39 (m, 10H), 7.94-8.03 (m, 1H), 8.19-8.27 (m, 1H).

Method 57

{4-[(2R,3R)-3-{[2-(4-Ethoxyphenyl)-2-oxoethyl]thio}-1-(4-fluorophenyl)-4-oxoazetidin-2-yl]phenoxy}acetic acid tert-Butyl (4-{(2R,3R)-1-(4-fluorophenyl)-3-[(3-nitropyridin-2-yl)dithio]-4-oxoazetidin-2-yl}phenoxy)acetate (0.25 g, 0.45 mmol) was dissolved in acetone (10 ml) at room temperature. Water (2.5 ml) and triphenyl phosphine (0.12 g, 0.45 mmol) were added. The mixture was stirred at room temperature for 15 minutes and then concentrated under reduced pressure to afford the crude thiol as a brown oil. This crude thiol was immediately dissolved in CH$_2$Cl$_2$ (10 ml) and (2-bromo-3'-ethoxy acetophenone (0.22 g, 0.90 mmol) was added, followed by Et$_3$N (0.13 ml, 0.90 mmol). The mixture was stirred at room temperature for 19 hours, concentrated under reduced pressure and purified by flash-chromatography (Hex:EtOAc 3:1). This afforded a colourless oil that was dissolved in formic acid (10 ml) and stirred at ambient temperature for 18 hours. Concentration under reduced pressure and purification by flash-chromatography (hex:acetone:formic acid 60:40:0.1) afforded 0.13 g (57%) of the desired product as a pale yellow solid.

$^1$H-NMR (CD$_3$Cl, 200 MHz): δ 1.4 (t, 3H), 4.0-4.1 (m, 5H), 4.5 (s, 2H), 4.8 (d, 2H), 6.8-7.0 (m, 6H), 7.1-7.3 (m, 4H), 7.9 (d, 2H).

Method 58 tert-Butyl (4-{[(4-fluorophenyl)imino]methyl}phenoxy)acetate tert-Butyl (4-formylphenoxy)acetate (21.6 g, 0.09 mol) was dissolved in dry toluene (150 ml) and 4-fluoroaniline (8.8 ml, 0.091 mol) was added. The mixture was refluxed in a Dean-Stark apparatus for 23 hours, cooled and concentrated under reduced pressure. Addition of hexane and concentration under reduced pressure afforded 30.0 g (quant. yield) of the title compound as an off-white solid. NMR (200 MHz): 1.5 (s, 9H), 4.6 (s, 2H), 7.0-7.2 (m, 6H), 7.8 (d, 2H), 8.4 (s, 1H).

Method 59

(4S)-3-{[(4-Methoxybenzyl)thio]acetyl}-4-phenyl-1,3-oxazolidin-2-one (4-Methoxy-benzylsulfanyl)-acetic acid (1.3 g, 6.1 mmol) was dissolved in dry DCM (40 ml) and cooled to 0° C. N,N'-dicyclohexylcarbodiimide (6.1 g, 6.1 mmol) and DMAP (1.6 g, 12.9 mmol) were added and the mixture was stirred for 30 minutes. (S)-(+)-4-Phenyl-2-oxazolidinone (1.0 g, 6.1 mol) was added and the mixture was stirred at room temperature for 24 hours. The mixture was filtrated, concentrated under reduced pressure and purified by flash-chromatography (Hex:EtOAc 8:2 then 1:1). This afforded 1.7 g (77%) of the title compound as a white solid. NMR (200 MHz): 3.46-3.59 (m, 3H), 3.74-3.76 (m, 4H), 4.23-4.28 (m, 1H), 4.68 (t, 1H), 5.38-5-42 (m, 1H), 6.78 (d, 2H), 7.14 (d, 2H), 7.32-7.40 (m, 5H).

Method 60 tert-Butyl (4-{(1R)-1-(4-fluoroanilino)-2-[(4-methoxybenzyl)thio]-3-oxo-3-[(4S)-2-oxo-4-phenyl-1,3-oxazolidin-3-yl]propyl}phenoxy)acetate TiCl$_4$ (1M in DCM, 7.2 ml, 7.2 mmol) was added to a solution of tetraisopropyl orthotitanate (0.71 ml 2.4 mmol) in DCM (40 ml) held at 0° C. under inert atmosphere. The mixture was stirred for 15 minutes, then (4S)-3-{[(4-methoxybenzyl)thio]acetyl}-4-phenyl-1,3-oxazolidin-2-one (3.4 g, 9.6 mmol) in dry DCM (20 ml) was added and the mixture was stirred for five minutes. Then tert-butyl (4-{[(4-fluorophenyl)imino]methyl}phenoxy)acetate (6.3 g, 19.0 mmol) in dry DCM (30 ml) was added and the mixture was given −40° C. and stirred for 20 minutes. Ethyl diisopropyl amine (3.3 ml, 19.0 mmol) was added and the mixture was stirred at −40° C. for 19 hours. The mixture was then given −78° C., added isopropanol (50 ml) and slowly given room temperature over night. Water (100 ml) was added and the mixture was stirred for 35 minutes at room temperature and then extracted twice with diethyl ether. The combined organic layer was washed with water, dried (MgSO$_4$) and concentrated under reduced pressure. The crude product was dissolved in methanol and an off-white precipitate formed. Filtration and drying afforded 1.7 g (26%) of the title compound as an off-white solid. NMR (200 MHz): 1.5 (s, 9H), 3.65 (s, 1H), 3.8 (s, 3H), 4.1 (m, 1H), 4.4-4.6 (m, 4H), 5.0-5.2 (m, 2H), 5.4 (m, 1H), 6.4-6.6 (m, 2H), 6.7-7-4 (m, 15H).

Method 61

3-(R)-4-(R)-1-(4-Fluorophenyl)-3-(4-methoxybenzylsulphanyl)-4-[4-(t-butoxycarbonyl methoxy)phenyl]azetidin-2-one tert-Butyl (4-{(1R)-1-(4-fluoroanilino)-2-[(4-methoxybenzyl)thio]-3-oxo-3-[(4S)-2-oxo-4-phenyl-1,3-oxazolidin-3-yl]propyl}phenoxy)acetate (1.3 g, 1.9 mmol) was dissolved in dry toluene (140 ml) and heated to 90° C. under inert atmosphere. BSA (1.4 ml, 5.7 mmol) was added and the mixture was stirred at 90° C. for one hour. The mixture was then cooled to 45° C. and TBAF (dried, 0.1 g) was added. After 18 hours, additional BSA was added (0.5 ml, 2.0 mmol) and the temperature was kept at 45° C. for another six hours. After cooling, the mixture was concentrated under reduced pressure and purified by flash-chromatography (Hex:EtOAc 5:1). This afforded 0.55 g (55%) of the title compound as a white solid. MR (200 MHz): 1.5 (s, 9H), 3.7 (s, 3H), 3.9 (m, 3H), 4.5 (m, 3H), 6.7 (d, 2H), 6.8-7.0 (m, 4H), 7.0-7.2 (m, 6H).

Method 62

3-(R)-4-(R)-1-(4-Fluorophenyl)-3-[(3-nitropyridin-2-yl)dithio]-4-[4-(t-butoxycarbonyl methoxy)phenyl]azetidin-2-one 3-(R)-4-(R)-1-(4-Fluorophenyl)-3-(4-methoxybenzylsulphanyl)-4-[4-(t-butoxycarbonyl methoxy)phenyl]azetidin-2-one (0.65 g, 1.24 mmol) was dissolved in DCM (50 ml) and given 0° C. under inert atmosphere. 3-Nitro-2-pyridinesulfenyl chloride (0.28 g, 1.49 mmol) was added and the mixture was stirred for 75 minutes at 0° C. Then additional 3-nitro-2-pyridinesulfenyl chloride (0.05 g, 0.27 mmol) was added and the mixture was stirred for an additional 45 minutes at 0° C. Concentration under reduced pressure and purification by flash-chromatography (Hex:EtOAc 4:1 then 2:1) afforded 0.67 g (97%) of the desired product as a yellow oil. NMR (200 MHz): 1.6 (s. 9H), 4.3 (d, 1H), 4.5 (s, 2H), 5.2 (d, 1H), 6.8-7.0 (m, 4H), 7.1-7.3 (m, 4H), 7.4 (m, 1H) 8.5 (d, 1H), 8.9 (d, 1H).

Method 63

3-(R)-4-(R)-1-(4-Fluorophenyl)-3-[(4-fluorobenzoyl) methylthio]-4-[4-(t-butoxycarbonyl methoxy)phenyl] azetidin-2-one 3-(R)-4-(R)-1-(4-Fluorophenyl)-3-[(3-nitropyridin-2-yl) dithio]-4-[4-(t-butoxycarbonyl methoxy)phenyl]azetidin-2-one (0.67 g, 1.2 mmol) was dissolved in acetone (50 ml) at room temperature, then water (10 ml) and tributyl phosphine (0.30 ml, 1.2 mmol) was added. The mixture was stirred at room temperature for 30 minutes and then concentrated under reduced pressure to afford the crude thiol as a brown oil. This crude thiol was immediately dissolved in DCM (40 ml) and 2-bromo-4'-fluoroacetophenone (0.29 g, 1.3 mmol) was added, followed by Et$_3$N (0.20 ml, 1.4 mmol). The mixture was stirred at room temperature for 90 minutes, concentrated under reduced pressure and purified by flash-chromatography (Hex:EtOAc 4:1). This afforded 0.42 g (65% total over two steps) of the title compound as a white solid.

NMR (200 M 1.44 (s, 9H), 4.06 (d, J=2.4 Hz, 1H), 4.13 (d, J=3.8 Hz, 2H), 4.48 (s, 2H), 4.81 (d, J=2.2 Hz, 1H), 6.83-6.93 (m, 4H), 7.05-7.21 (m, 6H), 7.90-7.97 (m, 2H).

Method 64

3-(R)-4-(R)-1-(4-Fluorophenyl)-3-[(4-fluorobenzoyl) methylthio]-4-[4-(carboxymethoxy)phenyl]azetidin-2-one 3-(R)-4-(R)-1-(4-fluorophenyl)-3-[(4-fluorobenzoyl)methylthio]-4-[4-(t-butoxycarbonylmethoxy)phenyl]azetidin-2-one (0.42 g, 0.78 mmol) was dissolved in DCM (30 ml) at 0° C. and TFA (7.5 ml) was added dropwise. The mixture was slowly given room temperature over several hours and then stirred at room temperature over night. Concentration under reduced pressure and purification by flash-chromatography (EtOAc, then 5% MeOH in EtOAc) afforded 0.32 g (85%) of the title compound as a white solid. NMR (CD$_3$OD, 300 MHz):4.1 (d, 1H), 4.2 (s, 2H), 4.5 (s, 2H), 5.0 (d, 1H), 6.9-7.0 (m, 4H), 7.1-7.3 (m, 6H), 8.0 (m, 2H).

Method 65 tert-Butyl N-[(2R)-2-amino-2-phenylacetyl]-O-(tert-butyl)-L-serinate tert-Butyl N-((2R)-2-{[(benzyloxy)carbonyl]amino}-2-phenylethanoyl)-O-(tert-butyl)-L-serinate (Method 15; 3.3 g, 6.8 mmol) was dissolved in EtOH (95%, 30 ml) and a cat amount of Pd/C (5%)(50% in water) was added and hydrogenation was performed at atmospheric pressure for 3 hours. at room temperature. The reaction mixture was filtered through diatomaceous earth and the solvent was evaporated to give the title compound (2.35 g, 98%). NMR (500 MHz, CD$_3$OD): 1.1 (s, 9H), 1.45 (s, 9H), 3.45-3.8 (m, 2H), 4.5 (t, 1H), 4.55 (s, 1H), 4.85 (s, 2H), 7.3-7.5 (m, 5H).

Method 66

1-(4-Fluorophenyl)-3-(R)-[(4-fluorobenzoyl)methylthio]-4-(R)-{4-[N-(α-(R)-{N-[2-(t-butoxy)-1-(S)-(t-butoxycarbonyl)ethyl]carbamoyl}benzyl)carbamoylmethoxy]phenyl}azetidin-2-one A solution of 3-(R)-4-(R)-1-(4-fluorophenyl)-3-[(4-fluorobenzoyl)methylthio]-4-[4-(carboxymethoxy)phenyl]azetidin-2-one (0.090 g, 0.186 mmol), tert-Butyl N-[(2R)-2-amino-2-phenylacetyl]-O-(tert-butyl)-L-serinate (Method 8; 0.098 g, 0.280 mmol) and N-methylmorpholine (0.062 ml, 0.563 mmol) in DMF (6 ml) was stirred at room temperature for 10 minutes, after which TBTU (0.096 g, 0.299 mmol) was added. After 22 hours, the reaction mixture was added water (15 ml) and extracted three times with ether (3×10 ml). The combined organic layers where washed with brine (10 ml), dried over MgSO$_4$ and concentrated. The residue was purified by flash chromatography on silica gel, using Hept:EtOAc (6:4) as eluent. The desired product was obtained in 0.053 g (35%) as a white solid. NMR (400 MHz): 0.90 (s, 9H), 1.45 (s, 9H), 3.35 (dd, 1H), 3.65 (dd, 1H), 4.10 (d, 1H), 4.15 (ABq, 2H), 4.50 (ABq, 2H), 4.50-4.60 (m, 1H), 4.85 (d, 1H), 5.55 (d, 1H), 6.40 (d, 1H), 6.90-7.00 (m, 4H), 7.10-7.40 (m, 1H), 7.90-8.00 (m, 3H); m/z: 816.7.

Method 67

1-(4-Fluorophenyl)-3-(R)-[(4-fluorobenzoyl)methylthio]-4-(R)-{4-[N-(α-(R)-{N-[2-(hydroxy)-1-(S)-(carboxy)ethyl]carbamoyl}benzyl)carbamoylmethoxy]phenyl}azetidin-2-one and Method 68

1-(4-Fluorophenyl)-3-(R)-[(4-fluorobenzoyl)methylthio]-4-(R)-{4-[N-(α-(R)-{N-[2-(t-butoxy)-1-(S)-(carboxy)ethyl]carbamoyl}benzyl)carbamoylmethoxy]phenyl}azetidin-2-one TFA (2 ml) was added to a solution of 1-(4-fluorophenyl)-3-(R)-[(4-fluorobenzoyl)methylthio]-4-(R)-{4-[N-(α-(R)-{N-[2-(t-butoxy)-1-(S)-(t-butoxycarbonyl)ethyl]carbamoyl}benzyl)carbamoylmethoxy]phenyl}azetidin-2-one (0.050 g, 0.061 mmol) in DCM (5 ml) at room temperature. After 2.5 hours the solvent was removed under reduced pressure and the residue was purified by preparative HPLC using a gradient of 20-60% MeCN in 0.1M ammonium acetate buffer as eluent. After freeze-drying, 1-(4-fluorophenyl)-3-(R)-[(4-fluorobenzoyl)methylthio]-4-(R)-{4-[N-(α-(R)-{N-[2-(hydroxy)-1-(S)-(carboxy)ethyl]carbamoyl}benzyl)carbamoylmethoxy]phenyl}azetidin-2-one was obtained in 0.039 g (90%).

NMR (DMSO, 400 MHz): 3.35 (dd, 1H), 3.50 (dd, 1H), 3,95-4.05 (m, 1H), 4.30 (d, 1H), 4.35 (ABq, 2H), 4.60 (ABq, 2H), 5.15 (d, 1H), 5.65 (d, 1H), 6.90-7.00 (m, 2H), 7.10-7.40 (m, 13H), 7.95-8.05 (m, 2H), 8.25 (d, 1H), 8.55 (d, 1H); m/z: 704.5. 1-(4-fluorophenyl)-3-(R)-[(4-fluorobenzoyl)methylthio]-4-(R)-{4-[N-(α-(R)-{N-[2-(t-butoxy)-1-(S)-(carboxy)ethyl]carbamoyl}benzyl)carbamoylmethoxy] phenyl}azetidin-2-one was obtained in 0.002 g (4%). NMR (CD$_3$COOD, 400 MHz): 1.00 (s, 9H), 3.50 (dd, 1H), 3.80 (dd, 1H), 4.20-4.30 (m, 3H), 4.70 (s, 2H), 4.80-4.85 (m, 1H), 5.00-5.05 (m, 1H), 5.90-6.00 (m, 1H), 6.95-7.05 (m, 4H), 7.15-7.50 (m, 1H), 8.00-8.10 (m, 2H); m/z: 760.5. Both were white solids.

Method 69

3-(R)-4-(R)-1-(4-Fluorophenyl)-3-[(4-fluorobenzoyl) methylthio]-4-{4-[N-(carboxymethyl) carbamoyl-methoxy]phenyl}azetidin-2-one A solution of 3-(R)-4-(R)-1-(4-fluorophenyl)-3-[(4-fluorobenzoyl)methylthio]-4-[4-(carboxymethoxy)phenyl]azetidin-2-one (0.200 g, 0.414 mmol), glycine tert-butyl ester hydrochloride (0.113 g, 0.674 mmol) and N-methylmorpholine (0.180 ml, 1.63 mmol) in DCM (5 ml) was stirred at room temperature for 10 minutes, after which TBTU (0.193 g, 0.601 mmol) was added. After 25 hours, the conversion to the ester (m/z: 597.43 $(M+1)^+$) was completed and TFA (2 ml) was added to the solution. After 1 hour, the solvent was removed under reduced pressure and the residue was purified by preparative HPLC using a gradient of 20-50% MeCN in 0.1M ammonium acetate buffer as eluent. After freeze-drying, the desired product was obtained in 0.093 g (41%) as a white solid. NMR (DMSO, 500 MHz): 3.65 (d, 2H), 4.35 (d, 1H), 4.40 (ABq, 2H), 4.50 (s, 2H), 5.20 (d, 1H), 6.95-7.05 (m, 2H), 7.15-7.40 (m, 8H), 8.00-8.15 (m, 3H); m/z: 541.3.

Method 70

1-(4-Fluorophenyl)-3-(R)-[(4-fluorobenzoyl)methylthio]-4-(R)-{4-[N-{N-[2-(hydroxy)-1-(R)-(carboxy)ethyl]carbamoylmethyl}carbamoylmethoxy] phenyl}azetidin-2-one A solution of 3-(R)-4-(R)-1-(4-fluorophenyl)-3-[(4-fluorobenzoyl)methylthio]-4-{4-[N-(carboxymethyl) carbamoylmethoxy]phenyl}azetidin-2-one (0.030 g, 0.056 mmol), D-serine tert-butyl ester hydrochloride (0.017 g, 0.067 mmol) and N-methylmorpholine (0.019 ml, 0.172 mmol) in DCM (4 ml) was stirred at room temperature for 10 minutes, after which TBTU (0.023 g, 0.072 mmol) was added. After 22 hours, the conversion to the ester (m/z: 740.58 $(M+1)^+$) was complete. TFA (1.5 ml) was added to the solution and after 2 hours, the solvent was removed under reduced pressure and the residue was purified by preparative HPLC using a gradient of 20-50% MeCN in 0.1M ammonium acetate buffer as eluent. After freeze-drying, the desired product was obtained in 0.035 g (~quantitative) as a white solid.

NMR (CD$_3$COOD, 400 MHz): 3.95 (dd, 1H), 4.10 (dd, 1H), 4.20-4.30 (m, 5H), 4.65 (s, 2H), 4.70-4.80 (m, 1H), 5.00 (d, 11, 6.95-7.10 (m, 4H), 7.15-7.45 (m, 6H), 8.00-8.10 (m, 2H); m/z: 628.4.

Method 71

1-(4-Fluorophenyl)-3-(R)-[(4-fluorobenzoyl)methylthio]-4-(R)-{4-[N-{N-[2-(phenyl)-1-(R)-(carboxy) ethyl]carbamoylmethyl}carbamoylmethoxy] phenyl}azetidin-2-one 3-(R)-4-(R)-1-(4-Fluorophenyl)-3-[(4-fluorobenzoyl)methylthio]-4-{4-[N-(carboxymethyl)carbamoylmethoxy] phenyl}azetidin-2-one (21 mg, 0.039 mmol), tert-butyl D-phenylalaninate HCl (12 mg, 0.047 mmol) and 4-methylmorpholine (12 mg, 0.12 mmol) were mixed in DCM (1 ml). TBTU (15 mg, 0.046 mmol) was added after 5 minutes and the mixture was stirred for 20 hours. The solvent was removed under reduced pressure and the residue purified by chromatography on silica with hexane:EtOAc 1:1 as the eluent. The product was dissolved in formic acid and stirred for 20 hours. The formic acid was removed under reduced pressure where after toluene was added and evaporated giving (21 mg 64%). M/z 686.3 $(M-H)^-$.

Method 72

{4-[(2R,3R)-1-(4-Fluorophenyl)-3-({2-hydroxy-2-[4-(methylthio)phenyl]ethyl}thio)-4-oxoazetidin-2-yl]phenoxy}acetic acid tert-Butyl (4-{(2R,3R)-1-(4-fluorophenyl)-3-[(3-nitropyridin-2-yl)dithio]-4-oxoazetidin-2-yl}phenoxy)acetate (0.25 g, 0.45 mmol) was dissolved in acetone (10 ml) at room temperature, then water (2.5 ml) and triphenyl phosphine (0.12 g, 0.45 mmol) was added. The mixture was stirred at room temperature for 15 minutes and then concentrated under reduced pressure to afford the crude thiol as a brown oil. This crude thiol was immediately dissolved in CH$_2$Cl$_2$ (10 ml) and (2-bromo-3'-thiomethyl acetophenone (0.22 g, 0.90 mmol) was added, followed by Et$_3$N (0.13 ml, 0.90 mmol). The mixture was stirred at room temperature for 19 hours, concentrated under reduced pressure and purified by flash-chromatography (Hex:EtOAc 4:1 then 3:1). This afforded 0.4 g of a mixture of tert-butyl {4-[(2R,3R)-1-(4-fluorophenyl)-3-({2-[4-(methylthio)phenyl]-2-oxoethyl}thio)-4-oxoazetidin-2-yl]phenoxy}acetate and 1-[4-(methylthio)phenyl]-2-[(3-nitropyridin-2-yl)thio]ethanone. This mixture was dissolved in HCOOH (15 ml) and stirred at room temperature for 19 hours. Concentration under reduced pressure and purification by flash-chromatography (hex:acetone:HCOOH 60:40:0.1) afforded 0.16 g (70%) of the desired compound as a pale yellow solid.

$^1$H-NMR (CD$_3$Cl, 200 M&): δ 2.5 (s, 3H), 4.0 (d, 1H), 4.1 (s, 2H), 4.6 (s, 2H), 4.8 (d, 1H), 6.8-7.0 (m, 4H), 7.1-7.3 (m, 6H), 7.8 (d, 2H).

Method 73

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-D-ornithine A mixture of 3-(R)-4-(R)-1-(4-Fluorophenyl)-3-[(4-fluorobenzoyl)methylthio]-4-(4-[N-(carboxymethyl) carbamoylmethoxy]phenyl)azetidin-2-one (0.020 g, 0.037 mmole) tert-butyl N$^5$-(tert-butoxycarbonyl)-D-ornithinate (0.012 g, 0.042 mmole), and N-methylmorpholine (0.012 mL, 0.111 mmole) in DCM (3 mL) was stirred at room temperature. TBTU (0.018 g, 0.056 mmole) was added and the mixture was stirred over night. Trifluoroacetic acid (1.0 mL) was added and after 6 hours the solvent was removed under reduced pressure. The residue was purified by preparative HPLC on a Kromasil C8-column using a gradient of 5-100% MeCN in 0.1M ammonium acetate-buffer as eluent. After removing the solvent under reduced pressure, 0.021 g (87%) of the desired product was obtained. M/z 655.21

Method 74

N-{[4-((2R,3R)-1-(4-fluorophenyl)-3-{[2-(4-fluorophenyl)-2-oxoethyl]thio}-4-oxoazetidin-2-yl)phenoxy]acetyl}glycyl-N$^6$,N$^6$-dimethyl-L-lysine 3-(R)-4-(R)-1-(4-Fluorophenyl)-3-[(4-fluorobenzoyl)methylthio]-4-{4-[N-(carboxymethyl) carbamoylmethoxy]

phenyl}azetidin-2-one (0.010 g, 0.018 mmole) and N-methylmorpholin (0.006 mL, 0.055 mmole) were dissolved in DMF (0.5 mL). TBTU (0.0099 g, 0.031 mmole) was added. The mixture was stirred at 30-40° C. for 30 minutes under $N_2$-atmosphere. $N^6,N^6$-dimethyl-L-lysine hydrochloride (0.0045 g, 0.021 mmole) was added and the mixture was stirred at 30-40° C. for some hours then at room temperature over night. A few drops of water were added and the solvent was removed under reduced pressure. The residue was purified by preparative HPLC on a Kromasil C8-column using a gradient of 5-100% MeCN in 0.1M ammonium acetate buffer as eluent. After removing the solvent under reduced pressure, 0.005 g (39%) of the desired product was obtained.

M/z 697.31

Method 75

N-{[4-((2R,3R)-1-(4-Fluorophenyl)-3-{[2-(4-fluorophenyl)-2-oxoethyl]thio}-4-oxoazetidin-2-yl)phenoxy]acetyl}glycine A mixture of [4-((2R,3R)-1-(4-fluorophenyl)-3-{[2-(4-methoxyphenyl)-2-oxoethyl]thio}-4-oxoazetidin-2-yl)phenoxy]acetic acid (0.0153 g, 0.031 mmol), tert-butyl glycyl-D-valinate hydrochloride (0.0099 g, 0.037 mmol) and N-methylmorpholine (0.010 ml, 0.091 mmol) in DCM (2 ml) was stirred at room temperature. TBTU (0.016 g, 0.050 mmol) was added and the mixture was stirred for 3.5 h. Trifluoroacetic acid (0.5 ml) was added and after 3.5 h the solvent was removed under reduced pressure. The residue was purified by preparative HPLC on a Kromasil C8-column using a gradient of 5-100% MeCN in 0.15% trifluoroacetic acid buffer as eluent. The solvent was removed under reduced pressure and 0.015 g (74%) of the title product was obtained. M/z 652.20.

Method 76

[4-((2R,3R)-1-(4-Chlorophenyl)-3-{[2-(4-chlorophenyl)-2-oxoethyl]thio}-4-oxoazetidin-2-yl)phenoxy] acetic acid tert-Butyl {4-[(2R,3R)-1-(4-chlorophenyl)-3-({[2-(4-chlorophenyl)-5,5-dimethyl-1,3-dioxan-2-yl]methyl}thio)-4-oxoazetidin-2-yl]phenoxy}acetate (1.69 g, 2.57 mmol) was dissolved in formic acid (25 ml) and stirred for two hours. The mixture was concentrated under reduced pressure (temperature <30° C.) and the crude oil was purified by flash-chromatography (hexane:acetone:formic acid 60:40:0.1) to afford 1.08 g (81%) of the title compound as a pale yellow solid. $^1$H-NMR (CDCl$_3$, 200 MHz): δ 4.0-4.2 (m, 3H), 4.7 (s, 2H), 4.9 (d, 1H), 6.9 (d, 2H), 7.2-7.4 (m, 6H), 7.5 (d, 2H), 7.9 (d, 2H). MS (CI) M/z: 514.2 (NT), 515.2 (30), 516.1 (70), 517.2 (20).

Examples of Intermediates of Formula (VI) and XV

Method 77

N-{[4-((2R,3R)-1-(4-fluorophenyl)-3-{[2-(4-fluorophenyl)-2-hydroxyethy]thio}-4-oxoazetidin-2-yl)phenoxy]acetyl}-D-alanine N-{[4-((2R,3R)-1-(4-fluorophenyl)-3-{[2-(4-fluorophenyl)-2-oxoethyl]thio}-4-oxoazetidin-2-yl)phenoxy]acetyl}-D-alanine was dissolved in methanol (1.5 ml). Sodium borohydride was added and the mixture was stirred for 30 minutes. An ammonium acetate/H2O solution (2 ml) was added and the methanol was evaporated. The product was purified by preparative HPLC (CH3CN/0.1% ammoniumacetate buffer 20:80-100:0). The fractions containing product were lyophilized and 27 mg (48%) of the title product was obtained. M/z: 555.0 (M−1).

Method 78

N-{[4-((2R,3R)-1-(4-fluorophenyl)-3-{[2-(4-fluorophenyl)-2-hydroxyethyl]thio}-4-oxoazetidin-2-yl)phenoxy]acetyl}-L-tryptophan

[4-((2R,3R)-1-(4-Fluorophenyl)-3-{[2-(4-fluorophenyl)-2-oxoethyl]thio}-4-oxoazetidin-2-yl)phenoxy]acetic acid (0.050 g, 0.103 mmol) was dissolved in CH$_2$Cl$_2$ (5 ml). Tryphtophane tert-butyl ester hydrochloride (0.037 g, 0.12 mmol) and N-methylmorpholine (31 mg, 0.31 mmol) were added. After 10 minutes, TBTU (43 mg, 0.13 mmol) was added and the mixture was stirred for 4 h. The crude ester was purified on silica gel and eluted with EtOAc/CH$_2$Cl$_2$, 25/75. The fractions containing pure ester were concentrated. CH$_2$Cl$_2$ (5 ml) and TFA (1 ml) were added and the reaction was stirred for 4 h. The mixture was concentrated and the remaining trace of TFA was azeotropically removed by co-evaporation with toluene (2×5 ml). The residue was dissolved in 5 ml of MeOH and sodium borohydride (0.016 g, 0.414 mmol) was added. The reaction was quenched by the addition of 0.1M NH$_4$OAc buffer (1 ml) after 5 minutes. The mixture was concentrated and purified by preparative HPLC (gradient 20-50% CH$_3$CN in 0.1M ammonium acetate buffer). Freeze-drying of the pure fractions gave the title compound as a colourless solid (0.040 g, 58%). MHz: 670.3 (M−1). $^1$H NMR [(CD$_3$)$_2$SO), 400 MHz] δ 2.85-2.95 (m, 2H), 3.07-3.12 (m, 1H), 3.22-3.27 (m, 1H), 4.24-4.27 (m, 1H), 4.34-4.38 (m, 1H), 4.41 (s, 2H), 4.70-4.76 (m, 1H), 5.01-5.04 (m, 1H), 6.80-7.35 (m, 16H), 7.50-7.53 (m, 1H), 7.85-7.92 (m, 1H), 10.76 (s, 1H).

Method 79

$N^2$-{[4-((2R,3R)-1-(4-fluorophenyl)-3-{[2-(4-fluorophenyl)-2-hydroxyethyl]thio}-4-oxoazetidin-2-yl)phenoxy]acetyl}-L-glutamine

[4-((2R,3R)-1-(4-Fluorophenyl)-3-{[2-(4-fluorophenyl)-2-oxoethyl]thio}-4-oxoazetidin-2-yl)phenoxy]acetic acid (50 mg, 0.103 mmol), tert-butyl L-glutaminate hydrochloride (30 mg, 0.124 mmol) and N-methylmorpholine (40 mg, 0.396 mmol) were dissolved in methylene chloride (1 ml). TBTU (40 mg, 0.125 mmol) was added and the mixture was stirred for 90 min. The solvent was evaporated and the residue was dissolved in formic acid (1 ml). The mixture was heated to 45-50° C. for 4 h. The reaction mixture was evaporated under reduced pressure. Toluene (5 ml) was added and evaporated. The residue was dissolved in methanol (1 ml). NaBH4 (30 mg, 0.793 mmol) was added and the mixture was stirred for 15 min. Acetic acid (50 mg, 0.83 mmol) was added and the reaction mixture was evaporated under reduced pressure. The residue was purified by preparative HPLC using acetonitrile/ammonium acetate buffer (35:65) as eluent. After freeze-drying 47 mg (74%) of the title compound was obtained. ¹H-NMR, 300 MHz, DMSO): 1.72-2.16 (m, 4H), 2.81-2.95 (m, 2H), 4.08-4.20 (m, 1H), 4.26-4.31 (m, 1H), 4.50 (s, 2H), 4.65-4.78 (m, 1H), 5.03-5.08 (m, 1H), 6.68 (s, 1H), 6.89-7.44 (m, 14H), 8.29 (d, 1H).

Method 80

N-{[4-((2R,3R)-1-(4-Fluorophenyl)-3-{[2-(4-fluorophenyl)-2-hydroxyethyl]thio}-4-oxoazetidin-2-yl)phenoxy]acetyl}-D-serine A solution of [4-((2R,3R)-1-(4-fluorophenyl)-3-{[2-(4-fluorophenyl)-2-oxoethyl]thio}-4-oxoazetidin-2-yl)phenoxy]acetic acid (0.050 g, 0.103 mmol), O-(tert-butyl)-D-serine tert-butyl ester hydrochloride (0.032 g, 0.147 mmol) and N-methylmorpholine (0.035 ml, 0.318 mmol) in DCM (4 ml) was stirred for 5 min. TBTU (0.044 g, 0.137 mmol) was added. The formation of the ester was confirmed after 3 h. M/z: 683.1. TFA (2 ml) was added and the mixture was stirred for 22 h. The solvent was removed under reduced pressure. The residue was dissolved in MeOH (4 ml) and NaBH4 (totally 0.130 g, 3.44 mmol) was added in small portions. The reaction was quenched by the addition of 0.1M ammonium acetate buffer (3 ml). The methanol was removed under reduced pressure. The remaining solution was purified by preparative HPLC using a gradient of 20-60% MeCN in 0.1M ammonium acetate buffer as eluent. After freeze-drying, 0.021 g (36% yield) of the title product was obtained as a white solid. M/z: 573.1. 1H NMR (DMSO, 400 MHz): δ 2.84-2.96 (m, 2H), 3.47 (dd, 1H), 3.69 (dd, 1H), 3.97-4.06 (m, 1H), 4.27-4.32 (m, 1H), 4.52 (ABq, 2H), 4.68-4.77 (m, 1H), 5.04-5.09 (m, 1H), 5.65 (bs, 1H), 6.99 (d, 2H), 7.07-7.41 (m, 10H), 7.89 (d, 1H).

It will be appreciated by those skilled in the art that the examples may be modified within the realms of the invention, why the invention is not limited to particular embodiments.

Absorption

Absorption of the compounds of formula (I) was tested in a Caco-2 cells model (Gastroenterology 1989, 96, 736):

| Compound (I) | Caco value (10⁻⁶ cm/sec) |
|---|---|
| N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-valine | 0.06 |
| N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-tyrosine | 0.07 |
| N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-lysine | 0.2 |
| 1-(4-Fluorophenyl)-3-(R)-[2-(4-fluorophenyl)-2-hydroxyethylthio]-4-(R)-{4-[N-{[2-(phenyl)-1-(R)-(carboxy)ethyl]carbamoylmethyl}carbamoylmethoxy]phenyl}azetidin-2-one | 0.09 |

The invention claimed is:
1. A compound of formula (I2):

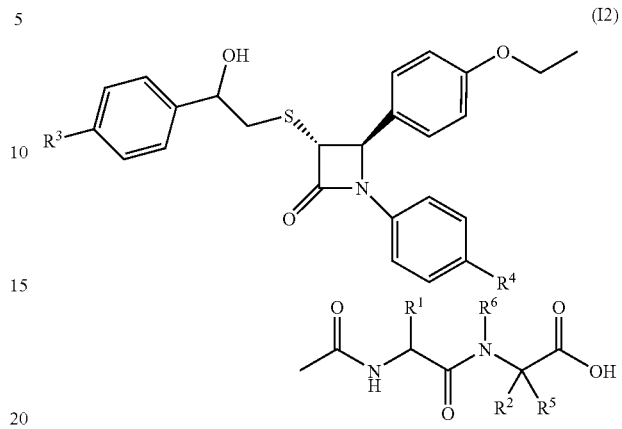

wherein:
$R^1$ is hydrogen, $C_{1-6}$alkyl, or $C_{3-6}$cycloalkyl; wherein said $C_{1-6}$alkyl may be optionally substituted by one or more hydroxy, amino, guanidino, carbamoyl, carboxy, $C_{1-6}$alkoxy, N-($C_{1-6}$alkyl)amino, N,N-($C_{1-6}$alkyl)$_2$amino, $C_1$-$C_6$ alkylcarbonylamino, $C_{1-6}$alkylS(O)$_a$ wherein a is 0-2, or $C_{3-6}$cycloalkyl;
$R^2$ and $R^5$ are independently hydrogen, a branched or unbranched $C_{1-6}$alkyl, or $C_{3-6}$cycloalkyl; wherein said $C_{1-6}$alkyl may be optionally substituted by one or more hydroxy, amino, guanidino, cyano, carbamoyl, carboxy, $C_{1-6}$alkoxy, ($C_1$-$C_4$alkyl)$_3$Si, N-($C_{1-6}$alkyl)amino, N,N-($C_{1-6}$alkyl)$_2$amino, $C_{1-6}$alkylS(O)$_a$, or $C_{3-6}$cycloalkyl, wherein a is 0-2;
$R^3$ is hydrogen, $C_{1-6}$alkyl, halo, $C_{1-6}$alkoxy or $C_{1-6}$ alkylS-;
$R^4$ is chlorine or fluorine;
$R^6$ is hydrogen or $C_{1-6}$ alkyl;
wherein $R^5$ and $R^2$ may form a ring with 2-7 carbon atoms and wherein $R^6$ and $R^2$ may form a ring with 3-6 carbon atoms;
or a pharmaceutically acceptable salt thereof.
2. A compound according to claim 1, wherein:
$R^1$ is hydrogen or phenyl.
3. A compound according to claim 1, wherein:
$R^2$ is hydrogen, a branched or unbranched $C_{1-6}$alkyl, or $C_{3-6}$cycloalkyl; wherein said $C_{1-6}$alkyl may be optionally substituted by one or more hydroxy, amino, acylamino, $C_{1-6}$alkylS(O)$_a$ wherein a is 0-2, or $C_{3-6}$cycloalkyl.
4. A compound according to claim 1, wherein:
$R^3$ is hydrogen, $C_1$-$C_2$alkyl, halo or methoxy.
5. A compound according to claim 1, wherein:
$R^3$ is hydrogen, methyl, chlorine, fluorine, $C_{1-6}$ alkylS-, or methoxy.
6. A compound according to claim 1, wherein:
$R^6$ is hydrogen, or $C_{1-6}$ alkyl, or $R^6$ and $R^2$ form a ring with 3-6 carbon atoms.
7. A compound according to claim 1, wherein:
$R^1$ is hydrogen;
$R^2$ is a branched or unbranched $C_{1-4}$alkyl, optionally substituted by a $C_{3-6}$cycloalkyl, or $C_{1-6}$alkyl-S-, amino, N-($C_{1-6}$alkyl)amino, or N,N-($C_{1-6}$alkyl)$_2$amino;
$R^3$ is halo;
$R^5$ is hydrogen or $C_{1-6}$ alkyl; and
$R^6$ is hydrogen.

8. One or more compounds chosen from:
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-$N^6$-acetyl-D-lysine;
1-(4-Fluorophenyl)-3-(R)-[2-(4-fluorophenyl)-2-hydroxyethylthio]-4-(R)-{4-[N-{N-[2-(phenyl)-1-(R)-(carboxy)ethyl]carbamoylmethyl}carbamoylmethoxy]phenyl}azetidin-2-one;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-valine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-tyrosine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-proline;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-D-lysine;
N-{[4-((2R,3R)-1-(4-fluorophenyl)-3-{[2-hydroxy-2-(4-methoxyphenyl)ethyl]thio}-4-oxoazetidin-2-yl)phenoxy]acetyl}glycyl-D-valine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-2-butylnorleucine;
N-{[4-((2R,3R)-1-(4-Fluorophenyl)-3-{[2-(4-fluorophenyl)-2-hydroxyethyl]thio}-4-oxoazetidin-2-yl)phenoxy]acetyl}glycyl-5-methyl-L-cysteine;
N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-3-cyclohexyl-D-alanine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-cyclohexyl-D-alanine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-4-methylleucine;
N-{[4-((2R,3R)-1-(4-Fluorophenyl)-3-{[2-(4-fluorophenyl)-2-hydroxyethyl]thio}-4-oxoazetidin-2-yl)phenoxy]acetyl}-L-alanyl-D-valine;
N-{[4-((2R,3R)-1-(4-fluorophenyl)-3-{[2-hydroxy-2-(4-methylphenyl)ethyl]thio}-4-oxoazetidin-2-yl)phenoxy]acetyl}glycyl-D-valine;
N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-D-valine;
N-{[4-((2R,3R)-1-(4-chlorophenyl)-3-{[2-(4-chlorophenyl)-2-hydroxyethyl]thio}-4-oxoazetidin-2-yl)phenoxy]acetyl}glycyl-3-methyl-D-valine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-(2-naphthyl)-D-alanine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-3-methyl-D-valine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-(3R,4S,5R)-3,4,5,6-tetrahydroxy-D-norleucine;
N-{[4-((2R,3R)-1-(4-Fluorophenyl)-3-{[2-(4-fluorophenyl)-2-hydroxyethyl]thio}-4-oxoazetidin-2-yl)phenoxy]acetyl glycyl-N,2 dimethylalanine;
N-({4-[(2R,3R)-1-(4-Fluorophenyl)-3-({2-hydroxy-2-[4-(methylthio)phenyl]ethyl}thio)-4-oxoazetidin-2-yl]phenoxy}acetyl)glycyl-3-methyl-D-valine valine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(4-methylbenzyl)-D-cysteine;
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-S-(tert-butyl)-D-cysteine; and
N-{[4-((2R,3R)-1-(4-fluorophenyl)-3-{[2-(4-fluorophenyl)-2-hydroxyethyl]thio}-4-oxoazetidin-2-yl)phenoxy]acetyl}glycyl-b,b-dimethyl-D-phenylalanine.

9. A method of treating a hyperlipidemic condition comprising the administration of an effective amount of a compound according to claim 1 to a mammal in need thereof 10. A method of treating atherosclerosis comprising the administration of an effective amount of a compound according to claim 1 to a mammal in need thereof 11. A pharmaceutical formulation comprising a compound according to claim 1 in admixture with a pharmaceutically acceptable adjuvant, diluent and/or carrier.

12. A combination of a compound according to formula (I)

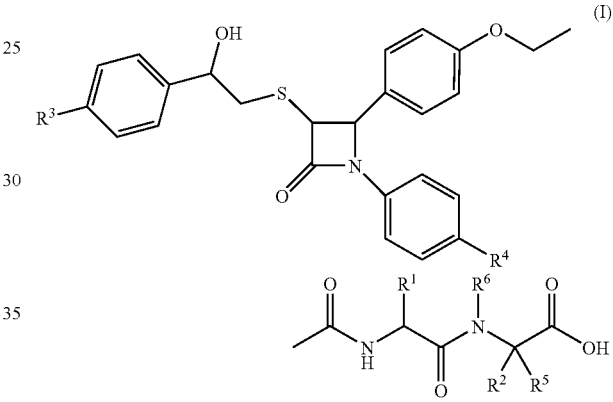

wherein:
$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N-($C_{1-6}$alkyl)amino, N,N-($C_{1-6}$alkyl)$_2$amino, $C_1$-$C_6$ alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;

$R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, ($C_1$-$C_4$alkyl)$_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl or $C_{1-6}$alkoxy;

$R^3$ is hydrogen, alkyl, halo, $C_{1-6}$alkoxy or $C_{1-6}$ alkylS-;

$R^4$ is hydrogen, $C_{1-6}$ alkyl, halo or $C_{1-6}$alkoxy;

$R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

or according to formula (I2)

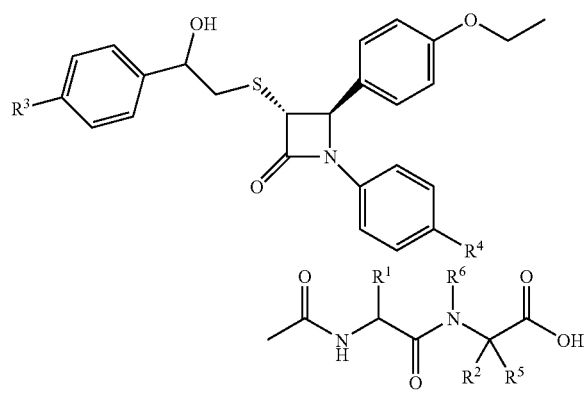

(I2)

wherein:
- $R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$ alkoxy, N-($C_{1-6}$ alkyl)amino, N,N-($C_{1-6}$ alkyl)$_2$ amino, $C_1$-$C_6$ alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;
- $R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, ($C_1$-$C_4$alkyl)$_3$Si, N-($C_{1-6}$ alkyl)amino, N,N-($C_{1-6}$ alkyl )$_2$amino, $C_{1-6}$alkylS(O)$_a$, $C_{3-6}$ cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl or $C_{1-6}$alkoxy;
- $R^3$ is hydrogen, alkyl, halo, $C_{1-6}$alkoxy or $C_{1-6}$ alkylS-;
- $R^4$ is hydrogen, $C_{1-6}$ alkyl, halo or $C_{1-6}$alkoxy;
- $R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

with a PPAR alpha and/or gamma agonist.

13. A combination of a compound according to formula (I)

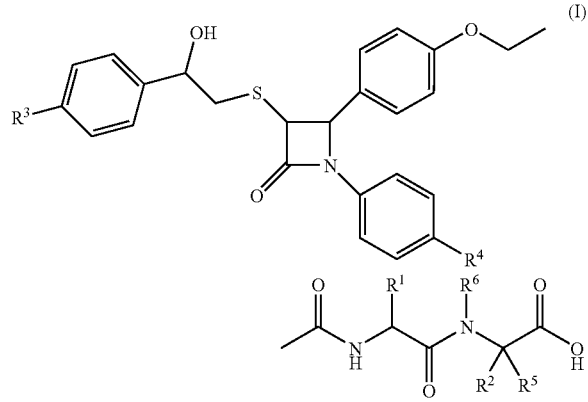

(I)

wherein:
- $R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N-($C_{1-6}$alkyl)amino, N,N-($C_{1-6}$alkyl)$_2$ amino, $C_1$-$C_6$ alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;
- $R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, ($C_1$-$C_4$alkyl)$_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl or $C_{1-6}$alkoxy;
- $R^3$ is hydrogen, alkyl, halo, $C_{1-6}$alkoxy or $C_{1-6}$ alkylS-;
- $R^4$ is hydrogen, $C_{1-6}$ alkyl, halo or $C_{1-6}$alkoxy;
- $R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms; or according to formula (I2)

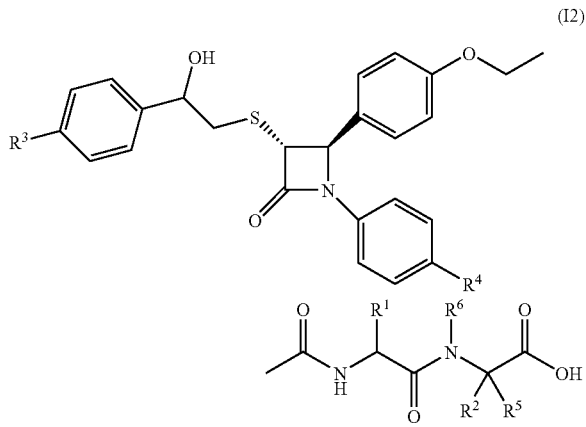

(I2)

wherein:
- $R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N-($C_{1-6}$alkyl)amino, N,N-($C_{1-6}$alkyl)$_2$ amino, $C_1$-$C_6$ alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl or $C_{1-6}$alkoxy;
- $R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, ($C_1$-$C_4$alkyl)$_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl or $C_{1-6}$alkoxy;
- $R^3$ is hydrogen, alkyl, halo, $C_{1-6}$alkoxy or $C_{1-6}$ alkylS-;

$R^4$ is hydrogen, $C_{1-6}$ alkyl, halo or $C_{1-6}$ alkoxy;
$R^6$ is hydrogen, $C_{1-6}$ alkyl, or aryl$C_{1-6}$ alkyl;
wherein $R^5$ and $R^2$ may form a ring with 2-7 carbon atoms and wherein $R^6$ and $R^2$ may form a ring with 3-6 carbon atoms;
with an HMG Co-A reductase inhibitor.

14. A combination of a compound according to claim 1 with a PPAR alpha and/or gamma agonist.

15. A combination of a compound according to claim 1 with an HMG Co-A reductase inhibitor.

* * * * *

UNITED STATES PATENT AND TRADEMARK OFFICE
CERTIFICATE OF CORRECTION

| | | |
|---|---|---|
| PATENT NO. | : 7,871,998 B2 | |
| APPLICATION NO. | : 10/596731 | |
| DATED | : January 18, 2011 | |
| INVENTOR(S) | : Susanne Alenfalk et al. | |

It is certified that error appears in the above-identified patent and that said Letters Patent is hereby corrected as shown below:

Col. 126, claim 5, please replace lines 54-55 with the following:

--A compound according to claim 1, wherein:
R3 is hydrogen, methyl, chlorine, fluorine, C1 6 alkylS-, or methoxy--

Col. 127, claim 8, please replace lines 65-67 with the following:

--N-({4-[(2R,3R)-1-(4-Fluorophenyl)-3-({2-hydroxy-2-[4-(methylthio)phenyl]ethyl}thio)-4-oxoazetidin-2-yl]phenoxy}acetyl)glycyl-3-methyl-D-valine;--

Signed and Sealed this
First Day of May, 2012

David J. Kappos
*Director of the United States Patent and Trademark Office*